United States Patent
Ishikawa et al.

[11] Patent Number: 5,714,479
[45] Date of Patent: *Feb. 3, 1998

[54] ENDOTHELIN ANTAGONISTIC HETEROAROMATIC RING-FUSED CYCLOPENTENE DERIVATIVES

[75] Inventors: Kiyofumi Ishikawa, Menuma-machi; Toshio Nagase, Tsukuba; Toshiaki Mase, Tsukuba; Takashi Hayama, Tsukuba; Masaki Ihara, Tsukuba; Masaru Nishikibe, Tsukuba; Mitsuo Yano, Tokyo, all of Japan

[73] Assignee: Banyu Pharmaceutical Co., Ltd., Tokyo, Japan

[*] Notice: The term of this patent shall not extend beyond the expiration date of Pat. No. 5,389,620.

[21] Appl. No.: 596,143
[22] PCT Filed: Aug. 16, 1994
[86] PCT No.: PCT/JP94/01357
 § 371 Date: Feb. 20, 1996
 § 102(e) Date: Feb. 20, 1996
[87] PCT Pub. No.: WO95/05374
 PCT Pub. Date: Feb. 23, 1995

Related U.S. Application Data

[63] Continuation-in-part of Ser. No. 296,410, Aug. 26, 1994, abandoned, which is a continuation of Ser. No. 165,880, Dec. 14, 1993, Pat. No. 5,389,620.

[30] Foreign Application Priority Data

| Aug. 18, 1993 | [JP] | Japan | 5-225100 |
| Oct. 15, 1993 | [JP] | Japan | 5-281613 |
| Oct. 21, 1993 | [JP] | Japan | 5-285677 |
| Mar. 30, 1994 | [JP] | Japan | 6-085914 |

[51] Int. Cl.$^6$ ............ A61K 31/435; C07D 471/04
[52] U.S. Cl. ............ 514/80; 514/248; 514/249; 514/258; 514/299; 544/232; 544/235; 544/244; 544/253; 544/337; 544/349; 546/112; 546/183; 546/23; 548/152; 548/180
[58] Field of Search ............ 546/112, 183; 544/232, 235, 244, 253, 337, 349; 548/152, 180; 514/299, 80, 248, 249, 258

[56] References Cited

U.S. PATENT DOCUMENTS 5,389,620  2/1995  Ishikawa et al. .

FOREIGN PATENT DOCUMENTS

WO 93/08799  5/1993  WIPO .

Primary Examiner—Bernard Dentz
Attorney, Agent, or Firm—Oblon, Spivak, McClelland, Maier & Neustadt, P.C.

[57] ABSTRACT

A heteroaromatic ring-fused cyclopentene derivative of the formula:

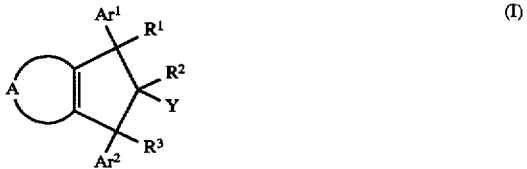

wherein the variables are as defined in the specification; or a pharmaceutically acceptable salt thereof.

22 Claims, No Drawings

ENDOTHELIN ANTAGONISTIC HETEROAROMATIC RING-FUSED CYCLOPENTENE DERIVATIVES

This application is a 371 of PCT/JP94/01357 filed Aug. 16, 1994, published as WO95/05374 Feb. 23, 1995, and a CIP of 08/296410 filed Aug. 26, 1994 now abandoned which was a continuation of 08/165,880 filed Dec. 14, 1993 now U.S. Pat. No. 5,389,620.

TECHNOLOGICAL FIELD

The present invention relates to novel compounds having antagonism against three endothelin isopeptides (endothelin-1, endothelin-2 and endothelin-3), which are physiologically highly active endogenous peptides, processes for their preparation and their use as a drug.

Two endothelin receptor subtypes $ET_A$ and $ET_B$ are known so far. The compounds of the present invention possess high affinity to at least one of two receptor subtypes, so that they show the dilative actions of smooth muscles, such as vessel and trachea. The compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

BACKGROUND TECHNOLOGY

Endothelin is a polypeptide composed of 21 amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad. Sci. USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan. J. Hypertension, 12, 79, (1989), J. Vascular Medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin. Invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys. Res. Commun., 157, 1164–1168 (1988); Biochem. Biophys. Res. Commun., 155, 167–172 (1989); Proc. Natl. Acad. Sci. USA, 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia(J. Cardiovasc. Pharmacol. , 22, 355–359 & 371–373(1993)). These data support a role of endothelin in the phathogenesis of vascular restenosis. Recently, it has been reported that both $ET_A$ and $ET_B$receptors exist in the human prostate and endothelin produces a potent contraction of it. These results suggest the possibility that endothelin is involved in the pathophysiology of benign prostatic hyperplasia(J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)).

Further, it was reported that cyclosporin remarkably increased endothelin secretion in the renal cell culture (LLC-PK1 cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J.

Cardiovasc. Pharmacol., 17(Suppl. 7), S119–S121 (1991)). One of endothelin receptors is $ET_A$ receptor selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since, the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

DISCLOSURE OF THE INVENTION

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. In the field of anti-endothelin agents, some non-peptidic compounds possessing antagonistic activity against endothelin receptors were already disclosed in patents (for example, EP 0526708 A1, WO 93/08799 A1). Accordingly, it is an object of the present invention to provide a novel therapeutics for the treatment of the above-mentioned various diseases by an invention of a novel and potent non-peptidic antagonist against either $ET_A$ or $ET_B$ receptor.

In order to accomplish the above object, the present inventors have synthesized various non-peptidic derivatives and have investigated their endothelin antagonistic activities, and as a result have found that novel heteroaromatic ring-fused cyclopentene derivatives represented by the following formula (I) and their pharmaceutically acceptable salts have potent affinity to at least one of these $ET_A$ and $ET_B$ receptor subtypes. The present invention has been accomplished on the basis of this discovery.

Thus, the present invention provides a non-peptidic derivative of the formula:

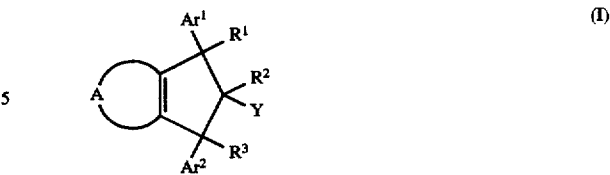

wherein each of $Ar^1$ and $Ar^2$ is independently a phenyl group, a thienyl group, a pyridyl group, an indolyl group, a benzofuranyl group or a dihydrobenzofuranyl group wherein an optional hydrogen atom(s) on the aromatic ring may be replaced with 1 to 4 groups selected from the group consisting of a halogen atom, a hydroxyl group, an amino group, a carboxyl group, a $C_1$–$C_6$ alkoxycarbonyl group, a mono- or di- $C_1$–$C_6$ alkylaminocarbonyl group, a carbamoyl group, a tetrazol-5-yl group, a methylenedioxy group, a $C_1$–$C_6$ alkoxy group, a $C_2$–$C_6$ alkenyloxy group, a mono- or di-$C_1$–$C_6$ alkylamino group, a $C_1$–$C_6$ alkyl group, a $C_2$–$C_6$ alkenyl group and a $C_2$–$C_6$ alkynyl group (provided that the $C_1$–$C_6$ alkoxy group, $C_2$–$C_6$ alkenyloxy group, mono- or di-$C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di- $C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di- $C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, $SO_3H$, $PO_3H_2$, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as substituents, they may together form a lactone ring)); each of $R^1$, $R^2$ and $R^3$ is independently a hydrogen atom, a hydroxyl group or a $C_1$–$C_6$ alkyl group, or $R^1$ and $R^2$, or $R^2$ and $R^3$ together form a single bond; Y is a group of —CO—$R^4$ (wherein $R^4$ is a hydroxyl group, an amino group, a $C_1$–$C_6$ alkoxy group, a mono- or di- $C_1$–$C_6$ alkylamino group, a $C_1$–$C_6$ alkylsulfonylamino group, or an arylsulfonylamino group or aryl $C_1$–$C_6$ alkylsulfonylamino group wherein an optional hydrogen atom(s) on the aryl ring may be replaced with a $C_1$–$C_6$ alkyl group), $SO_3H$, $PO_3H_2$, a tetrazol-5-yl group, a 2-oxo-3H-1,2,3,5-oxathiadiazol-4-yl group or a 5-oxo-4H-1,2,4-oxadiazol-3-yl group; and A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom (provided that optional 1 or 2 hydrogen atoms on the heteroaromatic ring may be replaced with a hydroxyl group, an amino group, a $C_1$–$C_6$ alkoxy group, a $C_1$–$C_6$ alkylthio group, a halogen atom, a cyano group, a nitro group, a mono- or di- $C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N-($C_1$–$C_6$ alkyl)-N-($C_3$–$C_8$ cycloalkyl) amino group which may be substituted by a hydroxyl group at the alkyl or alkylene moiety, an N-($C_1$–$C_6$ alkyl)-N-(aroyl)amino group which may be substituted by a hydroxyl group at the alkyl moiety, a $C_4$–$C_7$ cyclic imino group which may be substituted by a hydroxyl group at the alkylene moiety, a carboxyl group, a $C_1$–$C_6$ alkoxycarbonyl group, a formyl group, a $C_2$–$C_6$ alkanoyl group, an aroyl group, or a $C_1$–$C_6$ alkyl group, $C_3$–$C_8$ cycloalkyl group, $C_3$–$C_8$ cycloalkyl $C_1$–$C_6$ alkyl group, $C_2$–$C_6$ alkenyl group or $C_2$–$C_6$ alkynyl group which may be substituted by 1 to 3 substituents selected from the group consisting of a hydroxyl group, an amino group, a $C_1$–$C_6$ alkoxy group and a mono- or di- $C_1$–$C_6$ alkylamino group, and when the heteroaromatic ring includes one or more nitrogen atoms, the nitrogen atom(s) may be oxidized to form an N-oxide group); or a pharmaceutically acceptable salt thereof.

Now, the present invention will be described in further detail with reference to the preferred embodiments.

Now, the meanings of various abbreviations used in this specification will be given.

| Abbreviation | Meaning of Abbreviation |
| --- | --- |
| Et | ethyl |
| Me | methyl |
| ⁿPr | n-propyl |
| ⁱPr | isopropyl |
| ⁿBu | n-butyl |
| ᵗBu | tert-butyl |
| Ph | phenyl |
| Bzl | benzyl |
| c-Pent | cyclopentyl |
| CDI | 1,1'-carbonyldiimidazole |
| DCC | N,N'-dicyclohexylcarbodiimide |
| DMAP | 4-(dimethylamino)pyridine |
| DMF | N,N-dimethylformamide |
| DMSO | dimethylsulfoxide |
| HMPA | hexamethylphosphoric triamide |
| mCPBA | m-chloroperbenzoic acid |
| NMP | N-methylpyrrolidone |
| NMM | N-methylmorpholine |
| EDCl.HCl | 1-ethyl-3-(3-dimethylaminopropyl)-carbodiimide.hydrochloride |
| HOBT.H₂O | 1-hydroxy-1H-benzotriazole monohydrate |
| HOSu | N-hydroxysuccinimide |
| TEA | triethylamine |
| TFA | trifluoro acetic acid |
| THF | tetrahydrofuran |
| TsOH | p-toluene sulfonic acid |
| Ts | p-toluenesulfonyl |
| Z | benzyloxycarbonyl |
| MOPS | 3-morpholinopropane sulfonic acid |
| HEPES | 2-[4-(2-hydroxyethyl)-1-piperazinyl]-ethane sulfonic acid |
| Tris | tris(hydroxymethyl)aminomethane |
| PMSF | phenylmethanesulfonyl fluoride |

Now, the definitions of the various terms mentioned in this specification will be explained.

In this specification, the halogen atom means a fluorine, chlorine, bromine or iodine atom.

The $C_1$–$C_6$ alkoxycarbonyl group means an alkoxycarbonyl group having a linear or branched $C_1$–$C_6$ alkoxy group such as a methoxycarbonyl, ethoxycarbonyl, propoxycarbonyl, isopropoxycarbonyl, butyloxycarbonyl, isobutyloxycarbonyl, tert-butyloxycarbonyl, pentyloxycarbonyl, isopentyloxycarbonyl or hexyloxycarbonyl group.

The mono- or di- $C_1$–$C_6$ alkylaminocarbonyl group means an alkylaminocarbonyl group having 1 or 2 linear or branched $C_1$–$C_6$ alkyl groups at the nitrogen atom such as a methylaminocarbonyl, ethylaminocarbonyl, propylaminocarbonyl, isopropylaminocarbonyl, buylaminocarbonyl, isobutylaminocarbonyl, tert-buylaminocarbonyl, pentylaminocarbonyl, isopentylaminocarbonyl group, hexylaminocarbonyl, dimethylaminocarbonyl group, ethylmethylaminocarbonyl group, diethylaminocarbonyl, isopropylmethylaminocarbonyl, dipropylaminocarbonyl, ethylisopropylaminocarbonyl, diisopropylaminocarbonyl, dibutylaminocarbonyl, diisobutylaminocarbonyl, di-tert-butylaminocarbonyl, dipentylaminocarbonyl, ethylpentylaminocarbonyl, diisopentylaminocarbonyl or ethylhexylaminocarbonyl group.

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The $C_2$–$C_6$ alkenyloxy group means an alkenyloxy group having a linear or branched $C_2$–$C_6$ alkenyl group such as a vinyloxy, allyloxy, 1-propenyloxy, isopropenyloxy, 2-butenyloxy, 3-butenyloxy, 2-pentenyloxy, 3-methyl-3-butenyloxy or 2-hexenyloxy group.

The mono- or di- $C_1$–$C_6$ alkylamino group means an alkylamino group having 1 or 2 linear or branched $C_1$–$C_6$ alkyl groups at the nitrogen atom such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, diisopentylamino, isopentylmethylamino or dihexylamino group.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_2$–$C_6$ alkenyl group means a linear or branched alkenyl group having 2 to 6 carbon atoms such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The $C_2$–$C_6$ alkynyl group means a linear or branched alkynyl group having 2 to 6 carbon atoms such as a ethynyl, 1-propynyl, 2-propynyl, 1-butynyl, 2-butynyl, 3-butynyl, 1-methyl-2-propynyl or 1-pentynyl group.

The hydroxy $C_1$–$C_6$ alkylcarbonyl group means a linear or branched hydroxyalkylcarbonyl group having 2 to 7 carbon atoms such as a hydroxymethylcarbonyl, 1-hydroxyethylcarbonyl, 1-hydroxypropylcarbonyl, 1-hydroxybutylcarbonyl, 1-hydroxypentylcarbonyl, 1-hydroxyhexylcarbonyl, 2-hydroxyethylcarbonyl, 3-hydroxypropylcarbonyl, 2-hydroxybutylcarbonyl, 4-hydroxypentylcarbonyl, 3-hydroxyhexylcarbonyl or 2-hydroxy-2-methylpropylcarbonyl group.

The $C_1$–$C_6$ acyloxy $C_1$–$C_6$ alkylcarbonyl group means an acyloxy $C_1$–$C_6$ alkylcarbonyl group having a aliphatic or aromatic acyloxy group such as an acetyloxymethylcarbonyl, 1-acetyloxyethylcarbonyl, 2-acetyloxyethylcarbonyl, 1-acetyloxypropylcarbonyl, 1-acetyloxybutylcarbonyl, 1-acetyloxypentylcarbonyl, 1-acetyloxyhexylcarbonyl, 2-acetyloxypropylcarbonyl, propionyloxymethylcarbonyl, 1-propionyloxyethylcarbonyl, butylyloxymethylcarbonyl, pentanoyloxymethylcarbonyl, hexanoyloxymethylcarbonyl, benzoyloxymethylcarbonyl, 1-benzoyloxyethylcarbonyl, 2-benzoyloxyethylcarbonyl, thienylcarbonyloxymethylcarbonyl, furfuryloxymethylcarbonyl, pyridylcarbonyloxymethylcarbonyl or imidazolylcarbonyloxymethylcarbonyl group.

The carboxy $C_1$–$C_6$ alkoxycarbonyl group means a linear or branched carboxy $C_1$–$C_6$ alkoxycarbonyl group having 3 to 10 carbon atoms such as a carboxymethoxycarbonyl, 1-carboxyethoxycarbonyl, 1-carboxypropoxycarbonyl, 1-carboxybutoxycarbonyl, 2-carboxyethoxycarbonyl, 2-carboxybutoxycarbonyl, 2-carboxypentoxycarbonyl, 3-carboxyproxycarbonyl, 3-carboxybutoxycarbonyl, 4-carboxypentoxycarbonyl, 3-carboxyhexyloxycarbonyl or 2-carboxy-2-methylpropyloxycarbonyl group.

The carboxy $C_1$–$C_6$ alkoxycarbonyl $C_1$–$C_6$ alkoxycarbonyl group means a linear or branched carboxy $C_1$–$C_6$ alkoxycarbonyl $C_1$–$C_6$ alkoxycarbonyl group such as a carboxymethoxycarbonylmethoxycarbonyl, 1-carboxyethoxycarbonylmethoxycarbonyl, 1-carboxypropoxycarbonylmethoxycarbonyl, 1-carboxybuoxycarbonylmethoxycarbonyl, 2-carboxyethoxycarbonylmethoxycarbonyl, 2-carboxybutoxycarbonylethoxycarbonyl, 2-carboxypentoxycarbonylethoxycarbonyl, 3-carboxypropoxycarbonylethoxycarbonyl, 3-carboxybutoxycarbonylethoxycarbonyl, 4-carboxypentoxycarbonylethoxycarbonyl, 3-carboxyhexyloxycarbonylmethoxycarbonyl or 2-carboxy-2-methylpropyloxycarbonylmethoxycarbonyl group.

The $C_1$–$C_6$ alkylsulfonylaminocarbonyl group means an alkylsulfonylaminocarbonyl group having a linear or branched $C_1$–$C_6$ alkyl group such as a methylsulfonylaminocarbonyl, ethylsulfonylaminocarbonyl, propylsulfonylaminocarbonyl, isopropylsulfonylaminocarbonyl, butylsulfonylaminocarbonyl, isobutylsulfonylaminocarbonyl, tert-butylsulfonylaminocarbonyl, pentylsulfonylaminocarbonyl, isopentylsulfonylaminocarbonyl or hexylsulfonylaminocarbonyl group.

The $C_1$–$C_6$ alkylsulfonylamino group means an alkylsulfonylamino group having a linear or branched $C_1$–$C_6$ alkyl group such as a methylsulfonylamino, ethylsulfonylamino, propylsulfonylamino, isopropylsulfonylamino, butylsulfonylamino, isobutylsulfonylamino, tert-butylsulfonylamino, pentylsulfonylamino, isopentylsulfonylamino or hexylsulfonylamino group.

The arylsulfonylamino group means an arylsulfonylamino group having a $C_6$–$C_{14}$ aromatic hydrocarbon ring or heteroaromatic ring including 1 to 4 hetero atoms selected from the group consisting of an oxygen atom, a nitrogen atom and a sulfur atom such as a phenylsulfonylamino, naphthylsulfonylamino, thienylsulfonylamino, pyridylsulfonylamino or furylsulfonylamino group.

The aryl $C_1$–$C_6$ alkylsulfonylamino group means an aryl $C_1$–$C_6$ alkylsulfonylamino group having a $C_6$–$C_{14}$ aromatic hydrocarbon ring or heteroaromatic ring including 1 to 4 hetero atoms selected from the group consisting of an oxygen atom, a nitrogen atom and a sulfur atom at the alkyl moiety of the above-defined $C_1$–$C_6$ alkylsulfonylamino group such as a benzylsulfonylamino, phenylethylsulfonylamino, phenylpropylsulfonylamino, 1-methyl-2-phenylethylsulfonylamino, phenylbutylsulfonylamino, phenylpentylsulfonylamino, phenylhexylsulfonylamino, naphthylmethylsulfonylamino, naphthylethylsulfonylamino, naphthylpropylsulfonylamino, thienylmethylsulfonylamino, pyridylmethylsulfonylamino, furylmethylsulfonylamino, thienylethylsulfonylamino, pyridylethylsulfonylamino, furylethylsulfonylamino, thienylpropylsulfonylamino, pyridylbutylsulfonylamino, furylpentylsulfonylamino or thienylhexylsulfonylamino group.

The $C_1$–$C_6$ alkylthio group means a linear or branched alkylthio group having 1 to 6 carbon atoms such as a methylthio, ethylthio, propylthio, isopropylthio, butylthio, isobutylthio, sec-isobutylthio, tert-butylthio, pentylthio or hexylthio group.

The $C_3$–$C_8$ cycloalkylamino group means a cycloalkylamino group having 3 to 8 carbon atoms such as a cyclopropylamino, cyclobutylamino, cyclopentylamino, cyclohexylamino, cyclooctylamino, 2-methylcyclopropylamino, 1-methylcyclobutylamino, 2-methylcyclopentylamino or 2,2-dimethylcyclohexylamino group.

The $C_3$–$C_8$ cycloalkyl $C_1$–$C_6$ alkylamino group means a cycloalkylalkylamino group having a $C_3$–$C_8$ cycloalkyl at the alkyl moiety of the above-defined $C_1$–$C_6$ alkylamino group such as a cyclopropylmethylamino, cyclobutylmethylamino, cyclopentylmethylamino, cyclohexylmethylamino, cyclooctylmethylamino, 1-cyclopropylethylamino, 2-cyclopropylethylamino or 3-cyclopropylpropylamino group.

The N-($C_1$–$C_6$ alkyl)-N-($C_3$–$C_8$ cycloalkyl)amino group means an N-($C_1$–$C_6$ alkyl)-N-($C_3$–$C_8$ cycloalkyl)amino group having 4 to 15 carbon atoms such as an N-methyl-N-cyclopropylamino, N-methyl-N-cyclobutylamino, N-methyl-N-cyclopentylamino, N-methyl-N-cyclohexylamino, N-methyl-N-cyclooctylamino, N-ethyl-N-cyclopropylamino, N-butyl-N-cyclopropylamino, N-pentyl-N-cyclopropylamino, N-hexyl-N-cyclopropylamino, N-ethyl-N-cyclobutylamino, N-ethyl-N-cyclopentylamino, N-propyl-N-cyclobutylamino, N-pentyl-N-cyclopentylamino group.

The N-($C_1$–$C_6$ alkyl)-N-(aroyl)amino group means an N-($C_1$–$C_6$ alkyl)-N-(aroyl)amino group having 6 to 12 carbon atoms such as an N-methyl-N-benzoylamino, N-(1-ethyl)-N-benzoylamino, N-(1-propyl)-N-benzoylamino, N-(1-butyl)-N-benzoylamino, N-(1-pentyl)-N-benzoylamino, N-(2-ethyl-N-benzoylamino, N-(2-propyl)-N-benzoylamino, N-(3-butyl)-N-benzoylamino, N-(4-pentyl)-N-benzoylamino, N-methyl-N-naphthoylamino, N-methyl-N-thienylcarbonylamino, N-methyl-N-furylcarbonylamino, N-methyl-N-pyridylcarbonylamino or N-methyl-N-imidazoylcarbonylamino group.

The $C_4$–$C_7$ cyclic imino group means a cyclic imino group having 4 to 7 carbon atoms such as a 1-pyrrolidinyl, 2-methylpyrrolidino, 2,5-dimethylpyrrolidino, piperidino, 2-methylpiperidino, 2,6-dimethylpiperidino, morpholino, thiomorpholino, piperazino, 4-methylpiperazino or hexamethyleneimino group.

The $C_2$–$C_6$ alkanoyl group means a linear or branched alkanoyl group having 2 to 6 carbon atoms such as an acetyl, propanoyl, butylyl, isobutylyl, isopropanoyl, isobutylyl, pentanoyl or hexanoyl group.

The aroyl group means an aroyl group including mono-, bi- or tri-cyclic aromatic hydrocarbon ring or heteroaromatic ring including 1 to 4 hetero atoms selected from the group consisting of an oxygen atom, a nitrogen atom and a sulfur atom, such as a benzoyl, naphthoyl, pyridylcarbonyl, thienylcarbonyl, furylcarbonyl, thiazolylcarbonyl, oxazolylcarbonyl, imidazolylcarbonyl or quinolylcarbonyl group.

The $C_3$–$C_8$ cycloalkyl group means a cycloalkyl group having 3 to 8 carbon atoms such as a cyclopropyl, cyclobutyl, cyclopentyl, cyclohexyl, cycloheptyl or cyclooctyl group.

The $C_3$–$C_8$ cycloalkyl $C_1$–$C_6$ alkyl group means a $C_1$–$C_6$ alkyl group substituted by a $C_3$–$C_8$ cycloalkyl group such as a cyclopropylmethyl, 1-cyclopropylethyl, 2-cyclopropylethyl, 2-cyclopropylpropyl, 3-cyclopropylpropyl, 4-cyclopropylbutyl, 5-cyclopropylpentyl, 6-cyclopropylhexyl, cyclobutylmethyl, 1-cyclobutylethyl, 2-cyclobutylethyl, cyclopentylmethyl, cyclohexylmethyl, cycloheptylmethyl or cyclooctylmethyl group.

Now, this invention will be described in more detail with reference to specific examples for the various symbols used in the formula (I).

Each of $Ar^1$ and $Ar^2$ is independently a phenyl group, a thienyl group, a pyridyl group, an indolyl group, a benzofuranyl group or a dihydrobenzofuranyl group wherein an optional hydrogen atom(s) on the aromatic ring may be replaced with 1 to 4 groups selected from the group consisting of a halogen atom, a hydroxyl group, an amino group, a carboxyl group, a $C_1$–$C_6$ alkoxycarbonyl group, a mono- or di- $C_1$–$C_6$ alkylaminocarbonyl group, a carbamoyl group, a tetrazol-5-yl group, a methylenedioxy group, a $C_1$–$C_6$ alkoxy group, a $C_2$–$C_6$ alkenyloxy group, a mono- or di- $C_1$–$C_6$ alkylamino group, a $C_1$–$C_6$ alkyl group, a $C_2$–$C_6$ alkenyl group and a $C_2$–$C_6$ alkynyl group (provided that the $C_1$–$C_6$ alkoxy group, $C_2$–$C_6$ alkenyloxy group, mono- or di- $C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di- $C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di- $C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, $SO_3H$, $PO_3H_2$, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as substituents, they may together form a lactone ring)).

The halogen atom means a fluorine, chlorine, bromine or iodine atom.

The $C_1$–$C_6$ alkoxycarbonyl group means an alkoxycarbonyl group having a linear or branched $C_1$–$C_6$ alkoxy group such as a methoxycarbonyl, ethoxycarbonyl, propoxycarbonyl, isopropoxycarbonyl, butyloxycarbonyl, isobutyloxycarbonyl, tert-butyloxycarbonyl, pentyloxycarbonyl, isopentyloxycarbonyl or hexyloxycarbonyl group.

The mono- or di- $C_1$–$C_6$ alkylaminocarbonyl group means an alkylaminocarbonyl group having 1 or 2 linear or branched $C_1$–$C_6$ alkyl groups at the nitrogen atom such as a methylaminocarbonyl, ethylaminocarbonyl, propylaminocarbonyl, isopropylaminocarbonyl, buylaminocarbonyl, isobutylaminocarbonyl, tert-buylaminocarbonyl, pentylaminocarbonyl, isopentylaminocarbonyl group, hexylaminocarbonyl, dimethylaminocarbonyl group, ethylmethylaminocarbonyl group, diethylaminocarbonyl, isopropylmethylaminocarbonyl, dipropylaminocarbonyl, ethylisopropylaminocarbonyl, diisopropylaminocarbonyl, dibutylaminocarbonyl, diisobutylaminocarbonyl, di-tert-butylaminocarbonyl, dipentylaminocarbonyl, ethylpentylaminocarbonyl, diisopentylaminocarbonyl or ethylhexylaminocarbonyl group.

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The $C_2$–$C_6$ alkenyloxy group means an alkenyloxy group having a linear or branched $C_2$–$C_6$ alkenyl group such as a vinyloxy, allyloxy, 1-propenyloxy, isopropenyloxy, 2-butenyloxy, 3-butenyloxy, 2-pentenyloxy, 3-methyl-3-butenyloxy or 2-hexenyloxy group.

The mono- or di- $C_1$–$C_6$ alkylamino group means an alkylamino group having 1 or 2 linear or branched $C_1$–$C_6$ alkyl groups at the nitrogen atom such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, diisopentylamino, isopentylmethylamino or dihexylamino group.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_2$–$C_6$ alkenyl group means a linear or branched alkenyl group having 2 to 6 carbon atoms such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The $C_2$–$C_6$ alkynyl group means a linear or branched alkynyl group having 2 to 6 carbon atoms such as an ethynyl, 1-propynyl, 2-propynyl, 1-butynyl, 2-butynyl, 3-butynyl, 1-methyl-2-propynyl or 1-pentynyl group.

The hydroxy $C_1$–$C_6$ alkylcarbonyl group means a linear or branched hydroxyalkylcarbonyl group having 2 to 7 carbon atoms such as a hydroxymethylcarbonyl, 1-hydroxyethylcarbonyl, 1-hydroxypropylcarbonyl, 1-hydroxybutylcarbonyl, 1-hydroxypentylcarbonyl, 1-hydroxyhexylcarbonyl, 2-hydroxyethylcarbonyl, 3hydroxypropylcarbonyl, 2-hydroxybutylcarbonyl, 4-hydroxypentylcarbonyl, 3-hydroxyhexylcarbonyl or 2-hydroxy-2-methylpropylcarbonyl group.

The $C_1$–$C_6$ acyloxy $C_1$–$C_6$ alkylcarbonyl group means an acyloxy $C_1$–$C_6$ alkylcarbonyl group having a aliphatic or aromatic acyloxy group such as an acetyloxymethylcarbonyl, 1-acetyloxyethylcarbonyl, 2-acetyloxyethylcarbonyl, 1-acetyloxypropylcarbonyl, 1-acetyloxybutylcarbonyl, 1-acetyloxypentylcarbonyl, 1-acetyloxyhexylcarbonyl, 2-acetyloxypropylcarbonyl, propionyloxymethylcarbonyl, 1-propionyloxyethylcarbonyl, butylyloxymethylcarbonyl, pentanoyloxymethylcarbonyl, hexanoyloxymethylcarbonyl, benzoyloxymethylcarbonyl, 1-benzoyloxyethylcarbonyl, 2-benzoyloxyethylcarbonyl, thienylcarbonyloxymethylcarbonyl, furfuryloxymethylcarbonyl, pyridylcarbonyloxymethylcarbonyl or imidazolylcarbonyloxymethylcarbonyl group.

The carboxy $C_1$–$C_6$ alkoxycarbonyl group means a linear or branched carboxy $C_1$–$C_6$ alkoxycarbonyl group having 3 to 10 carbon atoms such as a carboxymethoxycarbonyl, 1-carboxyethoxycarbonyl, 1-carboxypropoxycarbonyl, 1-carboxybutoxycarbonyl, 2-carboxyethoxycarbonyl, 2-carboxybutoxycarbonyl, 2-carboxypentoxycarbonyl, 3-carboxypropoxycarbonyl, 3-carboxybutoxycarbonyl, 4-carboxypentoxycarbonyl, 3-carboxyhexyloxycarbonyl or 2-carboxy-2-methylpropyloxycarbonyl group.

The carboxy $C_1$–$C_6$ alkoxycarbonyl $C_1$–$C_6$ alkoxycarbonyl group means a linear or branched carboxy $C_1$–$C_6$ alkoxycarbonyl $C_1$–$C_6$ alkoxycarbonyl group having 3 to 16 carbon atoms such as a carboxymethoxycarbonylmethoxycarbonyl, 1-carboxyethoxycarbonylmethoxycarbonyl, 1-carboxypropoxycarbonylmethoxycarbonyl, 1-carboxybuoxycarbonylmethoxycarbonyl, 2-carboxyethoxycarbonylmethoxycarbonyl, 2-carboxybutoxycarbonylethoxycarbonyl, 2-carboxypentoxycarbonylethoxycarbonyl, 3-carboxypropoxycarbonylethoxycarbonyl, 3-carboxybutoxycarbonylethoxycarbonyl, 4-carboxypentoxycarbonylethoxycarbonyl, 3-carboxyhexyloxycarbonylmethoxycarbonyl or 2-carboxy-2-methylpropyloxycarbonylmethoxycarbonyl group.

The $C_1$–$C_6$ alkylsulfonylaminocarbonyl group means an alkylsulfonylaminocarbonyl group having a linear or branched $C_1$–$C_6$ alkyl group such as a methylsulfonylaminocarbonyl, ethylsulfonylaminocarbonyl, propylsulfonylaminocarbonyl, isopropylsulfonylaminocarbonyl, butylsulfonylaminocarbonyl, isobutylsulfonylaminocarbonyl, tert-butylsulfonylaminocarbonyl, pentylsulfonylaminocarbonyl, isopentylsulfonylaminocarbonyl or hexylsulfonylaminocarbonyl group.

Preferred compounds are those wherein $Ar^1$ and $Ar^2$ are independently a phenyl group, a thienyl group or a dihydrobenzofuranyl group wherein an optional hydrogen atom(s) on the aromatic ring may be replaced with 1 to 4 groups selected from the group consisting of a halogen atom, a hydroxyl group, an amino group, a methylenedioxy group, a $C_1$–$C_6$ alkoxy group, a $C_2$–$C_6$ alkenyloxy group, a mono- or di- $C_1$–$C_6$ alkylamino group, a $C_1$–$C_6$ alkyl group, a $C_2$–$C_6$ alkenyl group and a $C_2$–$C_6$ alkynyl group (provided that the said $C_1$–$C_6$ alkoxy group, $C_2$–$C_6$ alkenyloxy group, mono- or di- $C_1$–$C_6$ alkylamino group, $C_1$–$C_6$ alkyl group, $C_2$–$C_6$ alkenyl group and $C_2$–$C_6$ alkynyl group may be substituted by 1 to 3 groups selected from the group consisting of a phenyl group, a pyridyl group, an imidazolyl group, a hydroxyl group, a $C_1$–$C_6$ alkoxy group, an amino group, a mono- or di- $C_1$–$C_6$ alkylamino group, a hydroxy $C_1$–$C_6$ alkylcarbonyl group, a $C_1$–$C_6$ acyloxy $C_1$–$C_6$ alkylcarbonyl group, a carboxy $C_1$–$C_6$ alkoxycarbonyl group, a carboxy $C_1$–$C_6$ alkoxycarbonyl $C_1$–$C_6$ alkoxycarbonyl group, a $C_1$–$C_6$ alkoxycarbonyl group, a mono- or di- $C_1$–$C_6$ alkylaminocarbonyl group, a carbamoyl group, a $C_1$–$C_6$ alkylsulfonylaminocarbonyl group, a tetrazol-5-ylaminocarbonyl group, a carboxyl group, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as the substituents, they may together form a lactone ring)).

Each of $R^1$, $R^2$ and $R^3$ is independently a hydrogen atom, a hydroxyl group or a $C_1$–$C_6$ alkyl group, or $R^1$ and $R^2$, or $R^2$ and $R^3$ together form a single bond.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

When $R^1$ and $R^2$, or $R^2$ and $R^3$ together form a single bond, compounds of the general formula(I) are compounds of the general formula ($I^a$) or ($I^b$).

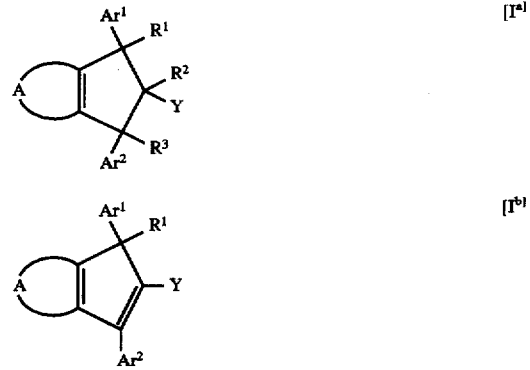

$Ar^2$, $Ar^2$, A, $R^1$ and $R^3$ are as defined above.

Y is a group of —CO—$R^4$ (wherein $R^4$ is a hydroxyl group, an amino group, a $C_1$–$C_6$ alkoxy group, a mono- or di- $C_1$–$C_6$ alkylamino group, a $C_1$–$C_6$ alkylsulfonylamino group, or an arylsulfonylamino group or aryl $C_1$–$C_6$ alkylsulfonylamino group wherein an optional hydrogen atom(s) on the aryl ring may be replaced with a $C_1$–$C_6$ alkyl group), $SO_3H$, $PO_3H_2$, a tetrazol-5-yl group, a 2-oxo-3H-1,2,3,5-oxathiadiazol-4-yl group or a 5-oxo-4H-1,2,4-oxadiazol-3-yl group.

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The mono- or di- $C_1$–$C_6$ alkylamino group means an alkylamino group having 1 or 2 linear or branched $C_1$–$C_6$ alkyl groups at the nitrogen atom such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, diisopentylamino, isopentylmethylamino or dihexylamino group, The $C_1$–$C_6$ alkylsulfonylamino group means an alkylsulfonylamino group having a linear or branched $C_1$–$C_6$ alkyl group such as a methylsulfonylamino, ethylsulfonylamino, propylsulfonylamino, isopropylsulfonylamino, butylsulfonylamino, isobutylsulfonylamino, tert-butylsulfonylamino, pentylsulfonylamino, isopentylsulfonylamino or hexylsulfonylamino group.

The arylsulfonylamino group wherein an optional hydrogen atom(s) on the aryl ring may be replaced with a $C_1$–$C_6$ alkyl group means an arylsulfonylamino group having a $C_6$–$C_{14}$ aromatic hydrocarbon ring or heteroaromatic ring including 1 to 4 hetero atoms selected from the group consisting of an oxygen atom, a nitrogen atom and a sulfur atom, wherein an optional hydrogen atom(s) on the aryl ring may be replaced with a $C_1$–$C_6$ alkyl group, such as a phenylsulfonylamino, naphthylsulfonylamino, thienylsulfonylamino, pyridylsulfonylamino or furylsulfonylamino group, or said groups having a $C_1$–$C_6$ alkyl group on the aromatic ring.

The aryl $C_1$–$C_6$ alkylsulfonylamino group wherein an optional hydrogen atom(s) on the aryl ring may be replaced with a $C_1$–$C_6$ alkyl group means an arylalkylsulfonylamino group having, at the alkyl moiety of the above-defined $C_1$–$C_6$ alkylsulfonylamino group, a $C_6$–$C_{14}$ aromatic hydrocarbon ring or heteroaromatic ring including 1 to 4 hetero atoms selected from the group consisting of an oxygen atom, a nitrogen atom and a sulfur atom, wherein an optional hydrogen atom(s) on the aryl ring may be replaced with a $C_1$–$C_6$ alkyl group, such as a benzylsulfonylamino, phenylethylsulfonylamino, phenylpropylsulfonylamino, 1-methyl-2-phenylethylsulfonylamino, phenylbutylsulfonylamino, phenylpentylsulfonylamino, phenylhexylsulfonylamino, naphthylmethylsulfonylamino, naphthylethylsulfonylamino, naphthylpropylsulfonylamino, thienylmethylsulfonylamino, pyridylmethylsulfonylamino, furylmethylsulfonylamino, thienylethylsulfonylamino, pyridylethylsulfonylamino, furylethylsulfonylamino, thienylpropylsulfonylamino, pyridylbutylsulfonylamino, furylpentylsulfonylamino or thienylhexylsulfonylamino group, or said groups having a $C_1$–$C_6$ alkyl group on the aromatic ring.

A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom (provided that optional 1 or 2 hydrogen atoms on the heteroaromatic ring may be replaced with a hydroxyl group, an amino group, a $C_1$–$C_6$ alkoxy group, a $C_1$–$C_6$ alkylthio group, a halogen atom, a cyano group, a nitro group, a mono- or di- $C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N-($C_1$–$C_6$ alkyl)-N-($C_3$–$C_8$ cycloalkyl)amino group which may be substituted by a hydroxyl group at the alkyl or alkylene moiety, an N-($C_1$–$C_6$ alkyl)-N-(aroyl)amino group which may be substituted by a hydroxyl group at the alkyl moiety, a $C_4$–$C_7$ cyclic imino group which may be substituted by a hydroxyl group at the alkylene moiety, a carboxyl group, a $C_1$–$C_6$ alkoxycarbonyl group, a formyl group, a $C_2$–$C_6$ alkanoyl group, an aroyl group, or a $C_1$–$C_6$ alkyl group, $C_3$–$C_8$ cycloalkyl group, $C_3$–$C_8$ cycloalkyl $C_1$–$C_6$ alkyl group, $C_2$–$C_6$ alkenyl group or $C_2$–$C_6$ alkynyl group which may be substituted by 1 to 3 substituents selected from the group consisting of a hydroxyl group, an amino group, a $C_1$–$C_6$ alkoxy group and a mono- or di- $C_1$–$C_6$ alkylamino group, and when the heteroaromatic ring includes one or more nitrogen atoms, the nitrogen atom(s) may be oxidized to form an N-oxide group).

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The $C_1$–$C_6$ alkylthio group means a linear or branched alkylthio group having 1 to 6 carbon atoms such as a methylthio, ethylthio, propylthio, isopropylthio, butylthio, isobutylthio, sec-isobutylthio, tert-butylthio, pentylthio or hexylthio group.

The halogen atom means a fluorine, chlorine, bromine or iodine atom.

The mono- or di- alkylamino group wherein an optional hydrogen atom(s) at the alkyl moiety may be replaced with a hydroxyl group means a linear or branched alkylamino group having, at the nitrogen atom, 1 or 2 linear or branched alkyl groups which may be substituted by a hydroxyl group, such as a methylamino, ethylamino, propylamino, isopropylamino, butylamino, isobutylamino, tert-butylamino, pentylamino, isopentylamino, hexylamino, dimethylamino, ethylmethylamino, diethylamino, dipropylamino, propylmethylamino, ethylpropylamino, diisopropylamino, diisobutylamino, ethylisobutylamino, di-tert-butylamino, dipentylamino, diisopentylamino, isopentylmethylamino or dihexylamino group.

The $C_3$–$C_8$ cycloalkylamino group wherein an optional hydrogen atom(s) at the alkyl or alkylene moiety may be replaced with a hydroxyl group means a $C_3$–$C_8$ cycloalkylamino group which may be substituted by a hydroxyl group at the alkyl or alkylene moiety, such as a cyclopropylamino, cyclobutylamino, cyclopentylamino, cyclohexylamino, cyclooctylamino, 2-methylcyclopropylamino, 1-methylcyclobutylamino, 2-methylcyclopentylamino or 2,2-dimethylcyclohexylamino.

The $C_3$–$C_8$ cycloalkyl $C_1$–$C_6$ alkylamino group wherein an optional hydrogen atom(s) at the alkyl or alkylene moiety may be replaced with a hydroxyl group means a $C_3$–$C_8$ cycloalkyl $C_1$–$C_6$ alkylamino group which has 4 to 14 carbon atoms and may be substituted by a hydroxyl group at the alkyl or alkylene moiety, such as a cyclopropylmethylamino, cyclobutylmethylamino, cyclopentylmethylamino, cyclohexylmethylamino, cycloheptylmethylamino, cyclooctylmethylamino, 1-cyclopropylethylamino, 2-cyclopropylethylamino, 3-cyclopropylpropylamino, 2-cyclobutylethylamino or 2-cyclopentylethylamino group.

The N-($C_1$–$C_6$ alkyl)-N-($C_3$–$C_8$ cycloalkyl)amino group wherein an optional hydrogen atom(s) at the alkyl or alkylene moiety may be replaced with a hydroxyl group means an N-($C_1$–$C_6$ alkyl)-N-($C_3$–$C_8$cycloalkyl)amino group which has 4 to 15 carbon atoms and may be substituted by a hydroxyl group at the alkyl or alkylene moiety, such as an N-methyl-N-cyclopropylamino, N-methyl-N-cyclobutylamino, N-methyl-N-cyclopentylamino, N-methyl-N-cyclohexylamino, N-methyl-N-cyclooctylamino, N-ethyl-N-cyclopropylamino, N-butyl-N-cyclopropylamino, N-pentyl-N-cyclopropylamino, N-hexyl-N-cyclopropylamino, N-ethyl-N-cyclobutylamino, N-ethyl-N-cyclopentylamino, N-propyl-N-cyclobutylamino, N-pentyl-N-cyclopentylamino group.

The N-($C_1$–$C_6$ alkyl)-N-(aroyl)amino group wherein an optional hydrogen atom(s) at the alkyl moiety may be replaced with a hydroxyl group means an N-($C_1$–$C_6$ alkyl)-N-(aroyl)amino group which has 6 to 12 carbon atoms and may be substituted by a hydroxyl group at the alkyl moiety, such as an N-methyl-N-benzoylamino, N-(1-ethyl)-N-benzoylamino, N-(1-propyl)-N-benzoylamino, N-(1-butyl)-N-benzoylamino, N-(1-pentyl-N-benzoylamino, N-(2-ethyl)-N-benzoylamino, N-(2-propyl)-N-benzoylamino, N-(3-butyl-N-benzoylamino, N-(4-pentyl)-N-benzoylamino, N-methyl-N-naphthoylamino, N-methyl-N-thienylcarbonylamino, N-methyl-N-furylamino, N-methyl-N-pyridylamino or N-methyl-N-imidazoylamino group.

The $C_4$–$C_7$ cyclic imino group wherein an optional hydrogen atom(s) may be replaced with a hydroxyl group means a cyclic imino group which has 4 to 7 carbon atoms and may be substituted by a hydroxyl group at the alkylene moiety, such as a 1-pyrrolidinyl, 2-methylpyrrolidino, 2,5-dimethylpyrrolidino, piperidino, 2-methylpiperidino, 2,6-dimethylpiperidino, morpholino, thiomorpholino, piperazino, 4-methylpiperazino or hexamethyleneimino group.

The $C_1$–$C_6$ alkoxycarbonyl group means an alkoxycarbonyl group having a linear or branched $C_1$–$C_6$ alkoxy group such as a methoxycarbonyl, ethoxycarbonyl, propoxycarbonyl, isopropoxycarbonyl, butyloxycarbonyl, isobutyloxycarbonyl, tert-butyloxycarbonyl, pentyloxycarbonyl, isopentyloxycarbonyl or hexyloxycarbonyl group.

The $C_2$–$C_6$ alkanoyl group means a linear or branched alkanoyl group having 2 to 6 carbon atoms such as an acetyl, propanoyl, butylyl, isobutylyl, isopropanoyl, isobutylyl, pentanoyl or hexanoyl group.

The aroyl group means an aroyl group having mono-, bi- or tri-cyclic aromatic hydrocarbon ring or heteroaromatic ring including 1 to 4 hetero atoms selected from the group consisting of an oxygen atom, a nitrogen atom and a sulfur atom, such as a benzoyl, naphthoyl, pyridylcarbonyl, thienylcarbonyl, furylcarbonyl, thiazolylcarbonyl, oxazolylcarbonyl, imidazolylcarbonyl or quinolylcarbonyl group.

The $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_3$–$C_8$ cycloalkyl group means a cycloalkyl group having 3 to 8 carbon atoms such as a cyclopropyl, cyclobutyl, cyclopentyl, cyclohexyl, cycloheptyl or cyclooctyl group.

The $C_2$–$C_6$ alkenyl group means a linear or branched alkenyl group having 2 to 6 carbon atoms such as a vinyl, allyl, 2-propenyl, isopropenyl, 3-butenyl, 2-butenyl, 1-butenyl, 1-methyl-2-propenyl, 1-meth-yl-1-propenyl, 1-ethyl-1-ethenyl, 2-methyl-2-propenyl, 2-methyl-1-propenyl or 4-pentenyl group.

The $C_3$–$C_8$ cycloalkyl $C_1$–$C_6$ alkyl group means a $C_1$–$C_6$ alkyl group substituted by a $C_3$–$C_8$ cycloalkyl group such as a cyclopropylmethyl, 1-cyclopropylethyl, 2-cyclopropylethyl, 2-cyclopropylpropyl, 3-cyclopropylpropyl, 4-cyclopropylbutyl, 5-cyclopropylpentyl, 6-cyclopropylhexyl, cyclobutylmethyl, 1-cyclobutylethyl, 2-cyclobutylethyl, cyclopentylmethyl, cyclohexylmethyl, cycloheptylmethyl or cyclooctylmethyl group.

The $C_2$–$C_6$ alkynyl group means a linear or branched alkynyl group having 2 to 6 carbon atoms such as a ethynyl, 1-propynyl, 2-propynyl, 1-butynyl, 2-butynyl, 3-butynyl, 1-methyl-2-propynyl or 1-pentynyl group.

A is a group which forms together with the adjacent carbon-carbon double bond a 5- or 6-membered heteroaromatic ring including 1 to 4 hetero atoms selected from the group consisting of a nitrogen atom, an oxygen atom and a sulfur atom, and examples of the 5- or 6-membered heteroaromatic ring are a furan ring, a pyrrole ring, a thiophene ring, a diazole ring a thiazole ring, an oxazole ring, a pyridine ring, a diazine ring, a triazine ring, etc.

Preferred compounds are those wherein A is a group which forms together with the adjacent carbon-carbon double bond a 5- or 6-membered nitrogen-containing aromatic ring or the corresponding N-oxide ring (provided that optional 1 or 2 hydrogen atoms on the heteroaromatic ring may be replaced with a hydroxyl group, an amino group, a $C_1$–$C_6$ alkoxy group, a $C_1$–$C_6$ alkylthio group, a mono- or di- $C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N-($C_1$–$C_6$ alkyl)-N-($C_3$–$C_8$ cycloalkyl)amino group which may be substituted by a hydroxyl group at the alkyl or alkylene moiety, an N-($C_1$–$C_6$ alkyl)-N-(aroyl)amino group which may be substituted by a hydroxyl group at the alkyl moiety, a $C_4$–$C_7$ cyclic imino group which may be substituted by a hydroxyl group at the alkylene moiety, or a $C_1$–$C_6$ alkyl group, $C_3$–$C_8$ cycloalkyl group, $C_3$–$C_8$cycloalkyl $C_1$–$C_6$ alkyl group, $C_2$–$C_6$ alkenyl group or $C_2$–$C_6$ alkynyl group which may be substituted by 1 to 3 groups selected from the group consisting of a hydroxyl group, an amino group, a $C_1$–$C_6$ alkoxy group and a mono- or di- $C_1$–$C_6$ alkylamino group).

The present invention provides novel heteroaromatic ring-fused cyclopentene derivatives of Formula (I) above

which can be prepared by a process which comprises:

1) reacting a β-keto ester derivative of Formula (II):

wherein R is a $C_1$–$C_6$ alkyl group, and $A^1$ is A or its synthetic equivalents, with an aldehyde of Formula (III):

wherein $Ar^{21}$ is $Ar^2$ or its synthetic equivalents, in a suitable solvent such as benzene or toluene with a catalyst such as piperidinium acetate at −20° C. to reflux temperature of a solvent to provide a 2-propenate derivative of Formula (IV):

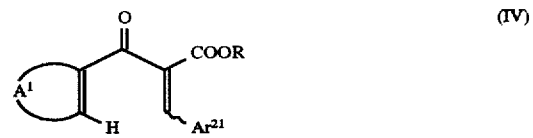

wherein $Ar^{21}$, $A^1$ and R are as defined before.

Cyclization of Compound (IV) in the presence of a suitable Lewis acid such as titanium tetrachloride, tin tetrachloride or aluminum chloride, or alternatively a protic acid such as trifluoroacetic acid, conc. $H_2SO_4$, perchloric acid or polyphosphoric acid in a suitable solvent such as benzene or toluene at −20° C. to reflux temperature of a solvent, provides a cyclopentene derivative of Formula (V):

wherein $Ar^{21}$, $A^1$ and R are as defined before.

Dehydrogenation of Compound (V) with 2,3-dichloro-5,6-dicyano-1,4-benzoquinone(DDQ) or alternative bromination of Compound (V) followed by dehydrobromination provides a cyclopentadienone derivative of Formula (VI):

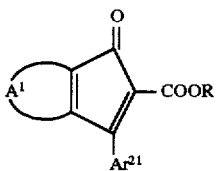
(VI)

wherein $Ar^{21}$, $A^1$ and R are as defined before.

2) Alternatively, a compound of Formula (VI) can be prepared as follows:

a compound of Formula (VII):

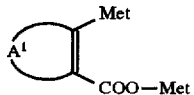
(VII)

wherein Met is metal and $A^1$ is as defined before, which was prepared by halogen-metal exchange reaction of the corresponding β-halocarboxylic acid with 2 equivalents of a metal reagent such as butyllithium, or by direct metallation of a β-hydrogen of the corresponding carboxylic acid with 2 equivalents of a strong base such as n-butyllithium, sec-butyllithium, tert-butyllithium, sodium or lithium, was treated with aroyl halide or arylnitrile in an aprotic solvent such as THF, $Et_2O$ or dimethoxyethane at $-100°$ C. to room temperature to provide a carboxylic acid derivative of Formula (VIII):

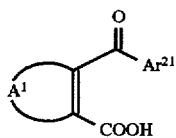
(VIII)

wherein $Ar^{21}$ and $A^1$ are as defined before.

To activate the carboxyl group, Compound (VIII) can be treated with a halogenated agent such as thionyl chloride or oxalyl chloride at $-40°$ C. to $100°$ C. or with CDI in an aprotic solvent such as $CHCl_3$, THF or DMF at $-20°$ C. to room temperature. The resulting activated carboxylic acid derivative, that is, acid chloride or imidazolide or activated ester, can then be treated with 1 to 5 equivalents of diethyl magnesium malonate, magnesium salt of malonic acid half ester or lithium enolate of acetic acid ester in a suitable solvent such as ether or THF at $-100°$ C. to $50°$ C. to give a compound of Formula (IX):

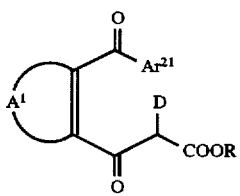
(IX)

wherein D is H, —COOR, —COOMet or —COOH, and $Ar^{21}$, $A^1$, R and Met are as defined before.

Treatment of Compound (IX) with an aqueous inorganic base such as sodium carbonate under heating, or with an acid such as 1N HCl, acetic acid or $SiO_2$ at $0°$ C. to room temperature gives a compound of Formula (VI).

Alternatively, Compound (VIII) can be prepared by reaction of a dicarboxylic acid anhydride of Formula (X):

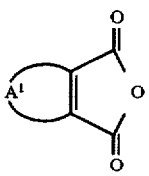
(X)

wherein $A^1$ is as defined before, or a dicarboxylic acid mono ester of Formula (XI):

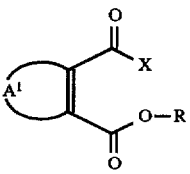
(XI)

wherein X is a leaving group, and $A^1$ and R are as defined before, with an organometallic reagent of Formula (XII):

$Ar^{21}$—Met (XII)

wherein $Ar^{21}$ and Met are as defined before, in an aprotic solvent such as THF or ether at $-100°$ C. to room temperature. Preferred organometallic reagents are organomagnesium reagents such as Grignard reagents, organolithium reagents or organozinc reagents.

3) Treatment of Compound (VI) with an organometallic reagent such as Grignard reagent of Formula (XIII):

$Ar^{11}$—Met (XIII)

wherein $Ar^{11}$ is $Ar^1$ or its synthetic equivalents and Met is as defined before, in a suitable solvent such as THF, $Et_2O$ or dimethoxyethane at $-100°$ C. to room temperature provides compounds of Formula (XIV):

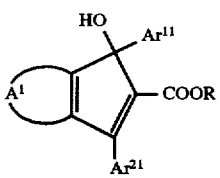
(XIV)

wherein $Ar^{11}$, $Ar^{21}$, $A^1$ and R are as defined before.

Hydrolysis of an ester group(s) of Compound (XIV) using an inorganic base such as NaOH or KOH or an acid such as HCl or TFA in an aqueous solvent such as methanol, ethanol, dioxane or acetonitrile, as the case is required, combined with the following procedures: i) appropriate conversion(s) of a synthetic equivalent(s) to a desired group(s), ii) deprotection of a protective group(s), affords compounds of the present invention which have a hydroxy group as $R^1$ in Formula (I).

Reduction of Compound (XIV) with a reductant such as triethylsilane in the presence of a Leuis acid such as boron trifluoride etherate or metal powder such as zinc and iron in the presence of acetic acid or HCl etc.; or hydrolysis of an ester group(s) of Compound (XIV) followed by reduction of a hydroxyl group and re-esterification of a carboxyl group affords an α,β-unsaturated ester of Formula (XV):

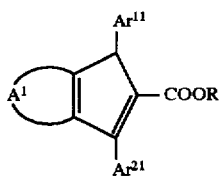

(XV)

wherein Ar¹¹, Ar²¹, A¹ and R are as defined before. Conjugate addition of an organometallic reagent of Formula (XVI):

$$R^{31}—Met \quad (XVI)$$

wherein $R^{31}$ is a $C_1-C_6$ alkyl group, and Met is as defined before, to Compound (XV), followed by appropriate conversion(s) of a synthetic equivalent(s) to a desired group (s) and/or deprotection of a protective group(s), hydrolysis of an ester group(s), as the case is required, affords compounds of the present invention which are shown in Formula (XVII):

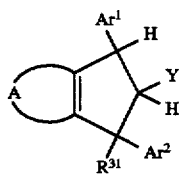

(XVII)

wherein Ar¹, Ar², A, $R^{31}$ and Y are as defined before.

Re-introduction of a double bond into an ester, which was obtained by reacting Compounds (XV) with Compounds (XVI), by appropriate methods such as DDQ oxidation or bromination-dehydrobromination followed by conjugate addition of another organometallic reagent of Formula (XVIII):

$$R^{11}—Met \quad (XVIII)$$

wherein $R^{11}$ is a $C_1-C_6$ alkyl group, and Met is as defined before, and subsequent appropriate conversion affords compounds of the present invention of Formula (XIX):

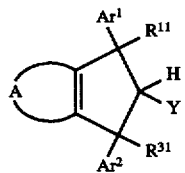

(XIX)

wherein Ar¹, Ar², A, $R^{11}$, $R^{31}$ and Y are as defined before.

Hydrogenation of Compound (XIV) with hydrogen gas under pressure at approximately 1–5 kg/cm² at room temperature to 50° C in the presence of a suitable acid such as acetic acid, conc-$H_2SO_4$ or perchloric acid using a suitable catalyst such as palladium on charcoal, or reduction of Compound(XIV) with metal such as zinc powder and iron powder and acid such as acetic acid and HCl at –78° C to room temperature in a mixture of etheric solvent of etheric solvent such as THF, ether, dioxane and alcoholic solvent such as methanol, ethanol, tert-butanol affords compounds of Formula (XX):

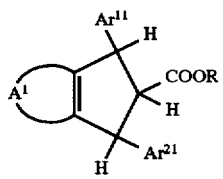

(XX)

wherein Ar¹¹, Ar²¹, A¹ and R are as defined before, which are converted to compounds of the present invention of Formula (XXI):

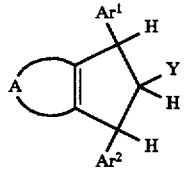

(XXI)

wherein Ar¹, Ar² A and Y are as defined before by appropriate reaction(s) such as hydrolysis of an ester group(s), conversion of a synthetic equivalent(s) to a desired functional group(s), or deprotection of a protective group(s).

Treatment of Compounds (XVII), (XIX) and their synthetic precursors, or Compound (XX) with a compound of Formula (XXII):

$$R^{21}—X \quad (XXII)$$

wherein $R^{21}$ is a $C_1-C_6$ alkyl group and X is a leaving group, in the presence of a base such as BuLi, LDA or NaH in a suitable solvent such as THF, $Et_2O$, DMF or DMSO at –100° C. to 100° C. followed by appropriate conversion(s) affords compounds of the present invention of Formula (XXIII):

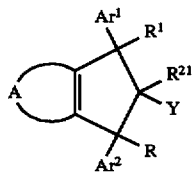

(XXIII)

wherein Ar¹, Ar², A, R¹, $R^{21}$, $R^3$ and Y are as defined before.

4) Treatment of Compound (V) with a sulfonic acid anhydride such as trifluoromethanesulfonic acid anhydride in the presence of a strong base such as BuLi or LDA, an organic base such as TEA, or a metal hydride such as NaH, in a suitable solvent such as THF, $Et_2O$, dimethoxyethane, DMF or DMSO at –78° C. to room temperature affords the corresponding sulfonyloxycyclopentadiene derivatives, which was allowed to react with an organometallic reagent of Formula (XXIV):

$$Ar^{11}—Met \quad (XXIV)$$

wherein Ar¹¹ and Met are as defined before, followed by an appropriate conversion(s) to give compounds of the present invention of Formula (XXI).

5) Among the compounds of the present invention the compounds, which have an above-defined substituent(s) on the heteroaromatic ring formed by combination of A and the adjacent carbon-carbon double bond, are prepared by the above-described methods 1) to 4) using a raw material(s) of Formula(II), (VII) or (X) having corresponding substituent (s) on the heteroaromatic ring.

They are also prepared by the following methods.
Treatment of the compounds of Formula(XXV):

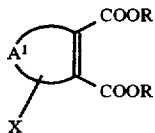
(XXV)

wherein X is a leaving group and $A^1$ and R are as defined before, with an arylmercaptide such as an alkylmercaptide or a phenylmercaptide under an inert gas such as nitrogen or argon in an inert solvent such as methanol, THF, ether, benzene, toluene to give the sulfide compounds of Formula (XXVI):

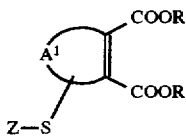
(XXVI)

wherein Z is a $C_1$–$C_6$ alkyl group or an aryl group and $A^1$ and R are as defined before.

The diester compounds(XXVI) are converted to the anhydride compounds(X), followed by conversion by the above-described methods to give the alcohol compounds of Formula(XXVII):

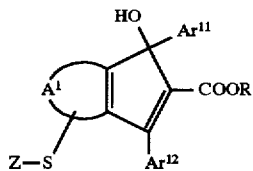
(XXVII)

wherein $A^1$, $Ar^{11}$, $Ar^{12}$, R and Z are as defined before.

A hydroxyl group of the alcohol compounds(XXVII) is protected by an appropriate protective group such as trimethylsilylethoxymethyl group, followed by oxidation of a sulfur atom bonded to the heteroaromatic ring with an appropriate oxidant such mCPBA as to give the sulfonyl compounds of Formula(XXVIII):

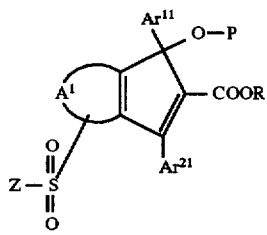
(XXVIII)

wherein P is a protective group, and $A^1$, $Ar^{11}$, $Ar^{21}$, R and Z as defined before.

Treatment of the compounds(XXVIII) with a nucleophlic reagent such as an organolithium reagent, lithium amide, a mercaptide or an alkoxide at −110° C. to room temperature in an inert solvent such as THF or ether to replace the hydrosulfonyl group on the heteroaromatic ring with a nucleophilic group, followed by the above-mentioned method(s) to give the compounds of the present invention.

6) Among the compounds of the present invention presented by Formula(I) the compounds, which have an amino group, a mono- or di- $C_1$–$C_6$ alkylamino group which may be substituted by a hydroxyl group at the alkyl moiety, a $C_3$–$C_8$ cycloalkylamino group which may be substituted by a hydroxyl group at the alkyl or alkylene moiety, a $C_3$–$C_8$ cycloalkyl $C_1$–$C_6$ alkylamino group which may be substituted by a hydroxyl group at the alkyl or alkylene moiety, an N-($C_1$–$C_6$ alkyl)-N-($C_3$–$C_8$ cycloalkyl)amino group which may be substituted by a hydroxyl group at the alkyl or alkylene moiety, an N-($C_1$–$C_6$ alkyl)-N-(aroyl)amino group which may be substituted by a hydroxyl group at the alkylene moiety or a $C_4$–$C_7$ cyclic imino group which may be substituted by a hydroxyl group at the alkylene moiety on the heteroaromatic ring formed by combination of A and the adjacent double bond containing at least one nitrogen atom, can be prepared by the above-described methods 1) to 5).

They can also be prepared by the following method.
The compounds of Formula:

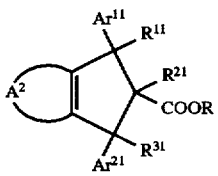
(XXIX)

wherein $A^2$ is A or its synthetic equivalents, the heteroaromatic ring which is formed by combination of $A^2$ and the adjacent double bond has at least one nitrogen atom and $Ar^{11}$, $Ar^{21}$, $R^{11}$, $R^{21}$, $R^{31}$ and R are as defined before, are treated with an oxidizing agent such as m-chloroperbenzoic acid or sodium periodate at −40° C. to room temperature in a solvent such as dichloromethane or chloroform to give the corresponding heteroaromatic ring N-oxide and the N-oxides were reacted at room temperature to boiling point of the solvent in a solvent such as methylene chloride, chloroform, 1,2-dichloroethane, DMF with an imidoyl halide prepared by treating an N-benzoyl derivative of a primary amine with thionyl chloride or phosphorus pentachloride without solvent or in an inert solvent such as benzene or toluene to give the compounds of Formula (XXX):

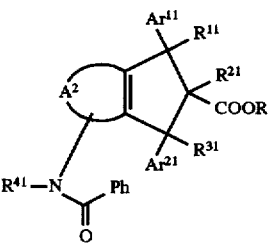
(XXX)

wherein $R^{41}$ is a $C^1$–$C^6$ alkyl group which may be substituted by a protected hydroxyl group, $A^2$, $Ar^{11}$, $Ar^{21}$, $R^{11}$, $R^{21}$, $R^{31}$ and R are as defined before, when primary amines, raw materials of the imidoyl halide, have a hydroxyl group as a substituent, it is preferable to protect the hydroxyl group with an appropriate protective group such as an acetyl group, a benzyl group or a benzoyl group. The imdoyl halide can be preferably reacted with the N-oxide in 5 to 30 equimolecular amounts to the N-oxide in the presence of 10 to 50 equimolecular amounts of inorganic base such as sodium hydrogencarbonate or cesium fluoride. Treatment of the compounds(XXX) with a base such as sodium hydroxide in a solvent such as methanol, 1,4-dioxane to remove the N-benzoyl group, followed by deprotection of the hydroxyl group at $R^{41}$, intramolecular or intermolecular nucleophlic substitution reaction, intramolecular or intermolecular reductive alkylation of the NH group, aroylation of the NH group or above-described reactions give the compounds of the present invention represented by Formula(I). The nucleophilic substitution reaction can be preferably carried out by reacting with an alkyl halide such as an alkylbromide or an alkyl iodide using a balky strong base such as lithium hexamethylene disilazide, LDA at −78° C. to room temperature in a solvent such as THF or ether. The intramolecular substitution reaction can be carried out by converting a desired hydroxyl group to the leaving group such as a halide, followed by the above-described nucleophilic substitution reaction. The reductive alkylation can be carried out by reacting with formalin or acetoaldehyde etc. in the presence of reducing agent such as formic acid or sodium cyanoborohydride, preferably at −20° C. to boiling point of the solvent. The intramolecular reductive alkylation can be carried out by oxidizing a desired hydroxyl group to the aldehyde, followed by subjecting to the same reaction as the above-described intermolecular reaction.

With appropriate manipulation and protection of any chemical functionalities, synthesis of the remaining compounds of the Formula (I) is accomplished by methods analogous to those above and to those described in the Experimental section.

All reaction intermediates and products so far described can be purified by well-known methods such as recrystallization, reprecipitation, partition procedures, normal- or reverse-phase chromatography and ion-exchange chromatography.

Now, the endothelin antagonistic properties of the heteroaromatic ring-fused cyclopentene derivatives of the present invention will be described.

Endothelin binding inhibition test to $ET_A$ receptor

The smooth muscle tissue of porcine aorta was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 25 mg/ml.

Then, 16 µl of this membrane suspension was added to 340 µl of 50 mM tris/HCl buffer, pH 7.4, containing 10 µl calcium chloride, 10 µM magnesium chloride, 0.1 mM PMSF, 1 µM pepstatin A, 2 µM leupeptin, 1 mM 1,10-phenanthroline and 0.1% bovine serum albumin. To this suspension, 4 µl of (A) endothelin-1 (for nonspecific binding; 0.2 µM as the final concentration), (B) buffer solution A (for total control binding), or (C) a test compound (1.1 µM as the final concentration), was added. Further, to each suspension, 40 µl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 µM of the test compound was determined by the following equation.

$$D(\%) = 100 - \frac{(C) - (A)}{(B) - (A)} \times 100$$

Each test was performed in triplicate.

Compound 2-enantiomer A, a representative compound of the present invention, was found to be very potent inhibitor of endothelin binding to $ET_A$ (99% inhibition at 1.1 µM).

Endothelin binding inhibition test to $ET_B$ receptor

The cerebellum of porcine was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 3.3 mg/ml.

Then, 16 µl of this membrane suspension was added to 340 µl of 50 mM tris/HCl buffer, pH 7.4, containing 10 µl calcium chloride, 10 µM magnesium chloride, 0.1 mM PMSF, 1 µM pepstatin A, 2 µM leupeptin, 1 mM 1,10-phenanthroline and 0.1% bovine serum albumin. To this suspension, 4 µl of (A) endothelin-1 (for nonspecific binding; 0.2 µM as the final concentration), (B) buffer solution A (for total control binding), or (C) a test compound (1.1 µM as the final concentration), was added. Further, to each suspension, 40 µl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 µM of the test compound was determined by the following equation.

$$D(\%) = 100 - \frac{(C) - (A)}{(B) - (A)} \times 100$$

Each test was performed in triplicate.

Compound 2-enantiomer A, a representative compound of the present invention, was found to be very potent inhibitor of endothelin binding to $ET_B$ (80% inhibition at 1.1 µM).

Activities against endothelin-induced contraction of isolated porcine coronary arteries The coronary artery of pig was extracted, and a spiral preparation having a width of 1 mm and a length of 10 mm was prepared therefrom. The preparation having the endothelial cells denuded, was hanged in a 5 ml organ bath filled with a Krebs.Heneseleit solution saturated with a gas mixture of 95% $O_2$ and 5% $CO_2$, and a change in the tension was isometrically measured and recorded.

Endothelin-1 was added into the organ bath in a cumulatively increasing manner, whereby the influence of a compound of the present invention to the concentration-response curve for endothelin-1 was examined. The compound was added into the organ bath 20 minutes prior to the addition of endothelin-1.

Compound 2 (10 µM), a representative compound of the present invention, remarkably shifted the concentration-response curves of endothelin-1 to the right and did not affect the maximum response. Further, the compound showed no effects to the isolated coronary artery when applied alone. As is evident from the above, the compound showed remarkable antagonistic activities against endothelin-induced concentration of isolated porcine coronary artery.

Endothelin binding inhibition test to human ET receptor

The human neuroblastoma SK-N-MC cells or the human Girardi heart cells purchased from Dainippon Seiyaku (Japan) were cultured in minimal essential medium supplemented with fetal calf serum. The cells were collected and homogenized in 10 mM MOPS buffer (pH 7.4) containing 154 mM NaCl, 10 mM KCl, 0.8 mM $CaCl_2$ and 20% sucrose at 4° C. using a polytron homogenizer. The homogenate was then centrifuged at 1,000×g for 15 minutes. The supernatant was centrifuged at 100,000×g for 1 hour at 4° C. Then the pellet was washed with 5 mM Hepes/Tris buffer (pH 7.4).

The resulting membranes were incubated with [$^{125}$I] endothelin-1 in the presence of each test compound or vehicle (1% dimethyl sulfoxide) in 50 mM Tris/HCl buffer (pH 7.4) containing 0.1 mM phenylmethanesulfonyl fluoride, 1 µM pepstatin, 2 µM leupeptin, 1 mM 1,10-phenanthroline, 1 mM EDTA, 10 µM CaCl$_2$, 10 µM MgCl$_2$ and 0.1% BSA in a total volume of 0.4 ml. After 4 hours incubation, cold 5 mM Hepes/Tris buffer (pH 7.4) containing 0.3% BSA (Buffer A) was added to the mixture. Free and bound [$^{125}$I]endothelin-1 were separated by filtration using Whatman GF/C glass fiber filters. After the filtration, the filters were washed with buffer A, and the radioactivity on the filters was measured in a γ counter. Nonspecific binding was determined in the presence of 200 nM endothelin-1. Percent (%) inhibition of [$^{125}$I]ET-1 specific binding by 1.1 µM of the test compound was determined.

Compound 2-enantiomer A, a representative compound of the present invention, was found to be very potent inhibitor of endothelin binding to ET$_A$ (99% inhibition) and ET$_B$ (80% inhibition) receptors, respectively.

Activities against endothelin-induced contraction of isolated rabbit iliac arteries The iliac artery of rabbit was isolated, and a spiral preparation having a width of 1 mm and a length of 10 mm was prepared therefrom. The preparation having the endothelial cells denuded, was placed in a 5 ml organ bath filled with a Krebs.Henseleit solution saturated with a gas mixture of 95% O$_2$ and 5% CO$_2$, and a change in the tension was isometrically measured and recorded.

Endothelin-1 was added into the organ bath in a cumulatively increasing manner, whereby the influence of a compound of the present invention to the concentration-response curve for endothelin-1 was examined. The compound was added into the organ bath 20 minutes prior to the addition of endothelin-1.

Compound 2 (0.1 to 10 µM) remarkably shifted the concentration-response curves of endothelin-1 to the right and did not affect the maximum response. Further, the compound showed no effects to the isolated iliac artery when applied alone. As is evident from the above, the compound showed remarkable antagonistic activities against endothelin-induced concentration of isolated rabbit iliac artery.

Plasma concentrations after oral dosing in rats

Male SD strain rats (8 weeks, n=3) with a cervical artery cannula were used in this experiment under a fasted condition. Compound 2, which is a representative of the invention, was suspended in 0.5% methylcellulose and administered orally in the stomach with a gavage at a dose of 10 mg/kg. The blood (120 µl) was drained from the cannula just before dosing, and 1 and 8 h after dosing. The plasma was separated by centrifugation (6000 rpm, 10 min, at 4° C.), and a portion (10 µl) was mixed with 40 µl of ethanol and the mixture was centrifugated (10000 rpm, 10 min, at 4° C.) to obtain supernatant. The supernatant (40 µl) was mixed with an equivalent volume of 0.2% trifluoroacetic acid (TFA), and the mixture was subjected to an HPLC assay to determine concentration of Compound 2-enantiomer A which is the active species.

Analytical conditions analytical column: Chiralcel OD-R (Daicel Chemical, φ4.6 mm×250 mm)

mobile phase: 0.1% TFA-water/0.1% TFA-acetonitrile= 75:25 flow rate: 1.0 ml/min oven temperature: 40° C.

injection volume: 50 µl detection: absorbance at 276 nm

Plasma concentrations of enantiomer A, the active species, were 8.77±3.52 µg/ml and 2.11±0.37 µg/ml at 1 and 8 h, respectively, after oral dosing of Compound 2.

Consequently, the compounds of the present invention were found to be highly orally absorbable and long lasting in the plasma.

Thus, the compounds of the present invention have excellent endothelin antagonistic activities and are useful as vasodilators or bronchodilators in the field of medicines, and they can be drugs for treating hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock endotoxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples illustrate the present invention more specifically. It should be understood that the present invention is not limited to these examples alone.

EXAMPLE 1

6-Ethoxycarbonyl-5-(3,4-methylenedioxyphenyl)-7-(4-methoxyphenyl)cyclopenteno[1,2-b]pyridine (Compound 1)

(1) 2-(4-Methoxyphenylcarbonyl)-3-pyridine carboxylic acid

To a THF (15 ml) solution of pyridine-2,3-dicarboxylic acid anhydride (1.0 g, 6.7 mmol) was added dropwise a THF solution of 4-methoxyphenylmagnesium bromide (0.89M, 8.0 ml, 7.1 mmol) at −78° C. The reaction mixture was stirred at the same temperature for 1 h and then a saturated aqueous solution of NH$_4$Cl (20 ml) was added to quench the reaction. The reaction mixture was diluted with 1N HCl and extracted with AcOEt. The organic layer was dried over MgSO$_4$, filtered, and concentrated under reduced pressure. The residue was purified by silica gel column chromatography (E. Merck, Kieselgel 60/chloroform:methanol=10:1) to give 2-(4-methoxyphenylcarbonyl)-3-pyridine carboxylic acid (479 mg) as a colorless solid.

(2) 2-(4-Methoxyphenylcarbonyl)-3-pyridylcarbonylmalonic acid diethyl ester

A mixture of 2-(4-methoxyphenylcarbonyl)-3-pyridine carboxylic acid (475 mg, 1.85 mmol) and thionyl chloride (11.0 ml) was stirred at 90° C. for 2 h. The reaction mixture was concentrated under reduced pressure and the residue was dissolved in anhydrous THF. This solution was concentrated under reduced pressure and the residue was dried in vacuo. The resulting residue was dissolved in a mixed solvent of anhydrous THF (6.0 ml) and anhydrous Et$_2$O (1.0 ml). To the solution was added diethyl magnesiummalonate (2.0M ether solution, 1.0 ml) which was prepared according to a method described in a literature (J. Am. Chem. Soc., 1946, 68, 1386–1388) and the mixture was stirred at 45° C. for 1.5 h. 1N HCl (10 ml) was added to quench the reaction. The mixture was diluted with water and extracted with AcOEt. The organic layer was dried over MgSO$_4$, filtered, and concentrated to give 2-(4-methoxyphenylcarbonyl)-3-pyridylcarbonylmalonic acid diethyl ester which was used in the next step without further purification.

(3) 6-Ethoxycarbonyl-5-oxo-7-(4-methoxyphenyl)cyclopent-1,3-dieno[2,1-b]pyridine To 2-(4-methoxyphenylcarbonyl)-3-pyridylcarbonylmalonic acid diethyl ester which is prepared in (2) was added a 5% aqueous solution of Na$_2$CO$_3$ (10 ml) and the mixture was refluxed for 10 min. After cooling, the supernatant solution was removed by decantation. The aqueous solution was diluted with water and extracted with AcOEt. The residue was suspended in water and the suspension was refluxed. After cooling, the suspension was diluted with brine and extracted with AcOEt. Combined AcOEt layer was dried over MgSO$_4$, filtered, and concentrated under reduced pressure. The residue was purified by silica gel column chromatography (E. Merck, Kieselgel 60/hexane:AcOEt=3:1 to 2:1 to 1:1) to give 6-ethoxycarbonyl-5-oxo-7-(4-methoxyphenyl)cyclopent-1,3-dieno-[2,1-b]pyridine (215 mg) as an orange oil.

(4) 6-Ethoxycarbonyl-5-hydroxy-5-3,4-methylenedioxyphenyl)-7-4-methoxyphenyl)cyclopent-1,3-dieno-[2,1-b]pyridine To a THF (5.0 ml) solution of 6-ethoxycarbonyl-5-oxo-7-(4-methoxyphenyl)cyclopent-1,3-dieno-[2,1-b]pyridine (208 mg, 0.67 mmol) was added dropwise 3,4-methylenedioxyphenylmagnesium bromide (1.08M THF solution, 0.8 ml, 0.86 mmol) under ice-cooling and the mixture was stirred at the same temperature for 30 min. To the mixture was added 1N HCl (10 ml) to quench the reaction. The mixture was extracted AcOEt and the organic layer was washed with brine, dried over MgSO$_4$, filtered, and concentrated under reduced pressure. The residue was purified by silica gel column chromatography (E. Merck, Kieselgel 60/hexane:AcOEt=2:1) to give 6-ethoxycarbonyl-5-hydroxy-5-(3,4-methylenedioxyphenyl)-7-(4-methoxyphenyl)cyclopent-1,3-dieno[2,1-b]pyridine (160 mg) as a yellow foam.

(5) 6-Ethoxycarbonyl-5-(3,4-methyl-enedioxyphenyl)-7-(4-methoxyphenyl)cyclopenteno[1,2-b]pyridine To a ethanol (4.0 ml) solution of 6-ethoxycarbonyl-5-hydroxy-5-(3,4-methylenedioxyphenyl)-7-(4-methoxyphenyl)cyclopent-1,3-dieno[2,1-b]pyridine (130 mg) were added conc. H$_2$SO$_4$ (2 drops) and 10% Pd-C (60 mg). The mixture was vigorously stirred at room temperature under an atmospheric pressure of hydrogen. After the reaction completed, the catalyst was removed by Celite-filtration. Combined filtrate and washings were washed with a saturated aqueous solution of NaHCO$_3$ and brine, dried over Na$_2$SO$_4$, filtered and concentrated under reduced pressure. The residue was purified by preparative TLC (E. Merck, Kieselgel 60 F$_{254}$/hexane:AcOEt=1:1) to give 6-ethoxycarbonyl-5-(3,4-methylenedioxyphenyl)-7-(4-methoxyphenyl)cyclopenteno[1,2-b]-pyridine (23 mg) as a pale yellow oil.

FAB-MS(m/e): 418(M+H)$^+$ $^1$H-NMR(300 MHz,CDCl$_3$,δ ppm): 0.69(3H,t,J=7.2 Hz), 3.46(2H,q,J=7.2 Hz),3.78(3H,s), 3.88(1H,t,J=7.6 Hz),4.70 (1H,d,J=7.6 Hz), 4.79(1H,d,J=7.6 Hz),5.94(1H,d,J=1.5 Hz), 5.95(1H,d,J=1.5 Hz),6.76–6.88(5H,m), 7.17(1H,dd,J=4.8 Hz,7.6 Hz),7.34(2H,d,J=8.9 Hz), 7.52(1H,d,J=7.6 Hz),8.51 (1H,d,J=4.8 Hz)

Rf Value: 0.45 (E. Merck, Kieselgel 60 F$_{254}$/hexane:AcOEt=1:1)

EXAMPLE 2

(5RS,6SR,7SR)-6-Carboxy-5-(3,4-methylenedioxyphenyl)-7-(4-methoxyphenyl)cyclopenteno[1,2-b]pyridine (Compound 2)

To a methanol (1.0 ml) solution of 6-ethoxycarbonyl-5-(3,4-methylenedioxyphenyl)-7-(4-methoxyphenyl)cyclopenteno[1,2-b]pyridine (20 mg, 0.048 mmol) which was prepared in Example 1-(5) was added a 4N aqueous solution of NaOH (0.2 ml) and the mixture was stirred at room temperature for 18 h. The reaction mixture was diluted with water, washed with Et$_2$O and AcOEt, and acidified with 1N HCl. The acidic solution was extracted with AcOEt. The organic layer was washed with brine, dried over Na$_2$SO$_4$, filtered, and concentrated under reduced pressure to give (5RS,6SR,7SR)-6-carboxy-5-(3,4-methylenedioxyphenyl)-7-(4-methoxyphenyl)cyclopenteno[1,2-b]pyridine (16 mg) as a pale yellow solid.

mp: 230°–233° C.(dec.)

FAB-MS(m/e): 390(M+H)$^+$ $^1$H-NMR(300 MHz,DMSO-d$_6$,δ ppm): 3.15(1H,t,J=10.1 Hz),3.73(3H,s), 4.52(1H,d,J=10.1 Hz),4.53(1H,d,J=10.1 Hz),6.01(2H,s), 6.77(1H,dd,J=1.7 Hz,7.7 Hz),6.84–6.91 (4H,m), 7.15–7.26(4H,m),8.33(1H,d,J=4.1 Hz)

Rf Value: 0.22 (E. Merck, Kieselgel 60 F$_{254}$/chloroform:methanol=10:1)

Compound 2 is a 1:1 mixture of each enantiomer (racemate). These enantiomers can be separated by reverse phase HPLC using a chiral column (Daicel Chemical Chiralcel OD-R, φ4.6 mm×250 mm, flow rate: 1.0 ml/min, 0.1% TFA-water/0.1% TFA-acetonitrile=75/25, column temperature: 40° C.).

Retention Time

Compound 2-enantiomer A: 9.8 min

Compound 2-enantiomer B: 12.1 min

Each Compound in the following Examples 3–18 was prepared in the same manner as in Examples 1 and 2.

EXAMPLE 3

6-Ethoxycarbonyl-5,7-diphenylcyclopenteno[1,2-b]-pyridine

EXAMPLE 4

(5RS,6SR,7SR)-6-Carboxy-5,7-diphenylcyclopenteno-[1,2-b]pyridine

EXAMPLE 5

6-Ethoxycarbonyl-5,7-di(4-methoxyphenyl)cyclopenteno[1,2-b]pyridine

EXAMPLE 6

(5RS,6SR,7SR)-6-Carboxy-5,7-di(4-methoxyphenyl)-cyclopenteno[1,2-b]pyridine

High Resolution FAB-MS(m/e,$(C_{23}H_{21}O_4N+H)^+$): Calcd: 376.1549 Found: 376.1536

$^1$H-NMR(300 MHz,CDCl$_3$,δ ppm): 3.33(1H,dd,J=9.6 Hz,10.0 Hz),3.79(3H,s),3.82(3H,s), 4.63(1H,d,J=9.6 Hz), 4.71(1H,d,J=9.6 Hz), 6.89(2H,d,J=8.8 Hz),6.90(2H,d,J=8.8 Hz), 7.12(1H,dd,J=4.6 Hz,8.6 Hz),7.19(2H,d,J=8.8 Hz), 7.20(2H,d,J=8.8 Hz),7.21–7.30(1H,m), 8.46(1H,dd,J=1.4 Hz,4.6 Hz)

Rf Value: 0.29 (E. Merck, Kieselgel 60 F$_{254}$/chloroform:methanol=10:1)

EXAMPLE 7

6-Ethoxycarbonyl-5,7-di(3,4-methylenedioxyphenyl)cyclopenteno[1,2-b]pyridine

EXAMPLE 8

(5RS,6SR,7SR)-6-Carboxy-5,7-di(3,4-methylenedioxyphenyl)cyclopenteno[1,2-b]pyridine

EXAMPLE 9

6-Ethoxycarbonyl-7-(3,4-methylenedioxyphenyl)-5-4-methoxyphenyl)-7-(3,4-methylenedioxyphenyl)cyclopenteno[1,2-b]pyridine

EXAMPLE 10

(5RS,6SR,7SR)-6-Carboxy-7-(3,4-methylenedioxyphenyl)-5-(4-methoxyphenyl)cyclopenteno[1,2-b]pyridine mp: 195°–205° C.

High Resolution FAB-MS(m/e,$(C_{23}H_{19}NO_5+H)^+$): Calcd: 390.1341 Found: 390.1338

$^1$H-NMR(300 MHz,CDCl$_3$,δ ppm): 3.30(1H,dd,J=9.8 Hz,10.1 Hz),3.82(3H,s), 4.61(1H,d,J=9.7 Hz),4.68(1H,d,J=10.1 Hz),5.92(2H,s), 6.68(1H,d,J=1.3 Hz),6.74(1H,dd,J=1.3 Hz,7.9 Hz), 6.79(1H,d,J=7.9 Hz),6.90(2H,d,J=8.8 Hz), 7.13 (1H,dd,J=4.9 Hz,7.7 Hz),7.19(2H,d,J=8.8 Hz), 7.28(1H,dd, J=1.6 Hz,7.7 Hz),8.48(1H,dd,J=1.6 Hz,4.9 Hz)

Rf Value: 0.25 (E. Merck, Kieselgel 60 F$_{254}$/chloroform:methanol=20:1)

EXAMPLE 11

6-Ethoxycarbonyl-5-phenyl-7-(4-methoxyphenyl)cyclopenteno[1,2-b]pyridine

EXAMPLE 12

(5RS,6SR,7SR)-6-Carboxy-5-phenyl-7-(4-methoxyphenyl)cyclopenteno[1,2-b]pyridine

High Resolution FAB-MS(m/e,$(C_{22}H_{19}NO_3+H)^+$): Calcd: 346.1443 Found: 346.1444

$^1$H-NMR(300 MHz,CDCl$_3$,δ ppm): 3.38(1H,t,J=9.8 Hz), 3.78(3H,s),4.68(1H,d,J=9.8 Hz), 4.73(1H,d,J=9.8 Hz),6.89 (2H,d,J=8.8 Hz), 7.12(1H,dd,J=4.9 Hz,8.6 Hz),7.19(2H,d, J=8.8 Hz), 7.20–7.40(6H,m),8.47(1H,dd,J=1.5 Hz,4.9 Hz)

Rf Value: 0.36 (E. Merck, Kieselgel 60 F$_{254}$/chloroform:methanol=10:1)

EXAMPLE 13

6-Ethoxycarbonyl-7-phenyl-5-(4-methoxyphenyl)cyclopenteno[1,2-b]pyridine

EXAMPLE 14

(5RS,6SR,7SR)-6-Carboxy-7-phenyl-5-(4-methoxyphenyl)cyclopenteno[1,2-b]pyridine

EXAMPLE 15

6-Ethoxycarbonyl-5-phenyl-7-(3,4-methylenedioxyphenyl)cyclopenteno[1,2-b]pyridine

EXAMPLE 16

(5RS,6SR,7SR)-6-Carboxy-5-phenyl-7-(3,4-methylenedioxyphenyl)cyclopenteno[1,2-b]pyridine

EXAMPLE 17

6-Ethoxycarbonyl-7-phenyl-5-(3,4-methylenedioxyphenyl)cyclopenteno[1,2-b]pyridine

EXAMPLE 18

(5RS,6SR,7SR)-6-Carboxy-7-phenyl-5-(3,4-methylenedioxyphenyl)cyclopenteno[1,2-b]pyridine High Resolution FAB-MS(m/e,$(C_{22}H_{17}NO_4+H)^+$): Calcd: 360.1236 Found: 360.1225

$^1$H-NMR(300 MHz,CDCl$_3$,δ ppm): 3.35(1H,t,J=9.7 Hz), 4.63(1H,d,J=9.7 Hz), 4.75(1H,d,J=9.7 Hz),5.97(2H,s),6.72 (1H,d,J=1.7 Hz), 6.77(1H,dd,J=1.7 Hz,8.0 Hz),6.81(1H,d, J=8.0 Hz), 7.14(1H,dd,J=5.5 Hz,8.3 Hz),7.20–7.40(6H,m), 8.48(1H,dd,J=1.7 Hz,5.5 Hz)

Rf Value: 0.47 (E. Merck, Kieselgel 60 F$_{254}$/chloroform:methanol=10:1)

Each Compound in the following Examples 19 and 20 was prepared using pyridine-3,4-dicarboxylic acid anhydride instead of pyridine-2,3-dicarboxylic acid anhydride as a starting material in the same manner as in Examples 1 and 2.

EXAMPLE 19

(5RS,6SR,7SR)-6-Carboxy-7-(3,4-methylenedioxyphenyl)-5-(4-methoxyphenyl)cyclopenteno[1,2-c]pyridine mp: 190°–192° C.

High Resolution FAB-MS(m/e,$(C_{23}H_{19}NO_5+H)^+$): Calcd: 390.1341 Found: 390.1354

$^1$H-NMR(300 MHz,DMSO-d$_6$,δ ppm): 3.18(1H,t,J=10.2 Hz),3.75(3H,s), 4.54(1H,d,J=10.2 Hz),4.60(1H,d,J=10.2 Hz), 6.02(2H,s),6.79–6.82(2H,m),6.89(1H,s), 6.89–6.94 (1H,m),6.93(2H,d,J=8.4 Hz), 7.23(2H,d,J=8.4 Hz),8.00(1H, s),8.38(1H,d,J=4.8 Hz), 12.41(1H,s)

Rf Value: 0.49 (E. Merck, Kieselgel 60 F$_{254}$/methylene chloride:methanol=8:1)

EXAMPLE 20

(5RS,6SR,7SR)-6-Carboxy-5-(3,4-methylenedioxyphenyl)-7-(4-methoxyphenyl)cyclopenteno[1,2-c]pyridine mp: 187° C. (dec)

High Resolution FAB-MS(m/e,$(C_{23}H_{19}NO_5+H)^+$): Calcd: 390.1341 Found: 390.1347

$^1$H-NMR(300 MHz,DMSO-$d_6$,δ ppm): 3.18(1H,t,J=10.6 Hz),3.76(3H,s), 4.55(1H,d,J=10.6 Hz),4.59(1H,d,J=10.6 Hz), 6.01(2H,s),6.79(1H,dd,J=1.7 Hz,8.1 Hz), 6.82–6.90 (3H,m),6.93(2H,d,J=8.5 Hz), 7.26(2H,d,J=8.5 Hz),7.96(1H,s),8.38(1H,d,J=4.6 Hz)

Each Compound in the following Examples 21–24 was prepared using the corresponding 6-substituted pyridine-2,3-dicarboxylic acid anhydride as a starting material in the same manner as in Examples 1 and 2.

EXAMPLE 21

(5RS,6SR,7SR)-6-Carboxy-2-propoxy-5-(3,4-methylenedioxyphenyl)-7-(4-methoxyphenyl)cyclopenteno[1,2-b]-pyridine High Resolution FAB-MS(m/e,$(C_{26}H_{25}NO_6+H)^+$): Calcd: 448.1760 Found: 448.1778

$^1$H-NMR(300 MHz,CDCl$_3$,δ ppm): 0.94(3H,t,J=7.2 Hz), 1.68(2H,sext,J=7.2 Hz), 3.21(1H,t,J=9.3 Hz),3.81(3H,s), 4.00–4.18(2H,m), 4.51(1H,d,J=9.3 Hz),4.64(1H,d,J=9.3 Hz),5.94(2H,s), 6.56(1H,d,J=8.0 Hz),6.70(1H,s),6.71–6.80 (2H,m), 6.87(2H,d,J=8.7 Hz),7.17(1H,d,J=8.0 Hz), 7.19(2H,d,J=8.7 Hz)

Rf Value: 0.44 (E. Merck, Kieselgel 60 F$_{254}$/chloroform:methanol=20:1)

EXAMPLE 22

(5RS,6SR,7SR)-6-Carboxy-2-methyl-5-(3,4-methylenedioxyphenyl)-7-(4-methoxyphenyl)cyclpenteno[1,2-b]-pyridine mp: 192°–194° C.

FAB-MS(m/e,$(C_{24}H_{21}NO_5+H)^+$): 404

$^1$H-NMR(300 MHz,DMSO-$d_6$,δ ppm): 2.35(3H,S),3.08 (1H,t,J=10.0 Hz),3.74(3H,s), 4.46(2H,t,J=10.0 Hz),6.00(2H,s), 6.75(1H,dd,J=1.6 Hz,8.0 Hz),6.81(1H,d,J=1.6 Hz), 6.87–6.91(3H,m),7.04(1H,d,J=7.8 Hz),7.11–7.17(3H,m)

Rf Value: 0.29 (E. Merck, Kieselgel 60 F$_{254}$/chloroform:methanol=20:1)

EXAMPLE 23

(5RS,6SR,7SR)-6-Carboxy-2-butyl-5-(3,4-methylenedioxyphenyl)-7-(4-methoxyphenyl)cyclopenteno[1,2-b]pyridine

EXAMPLE 24

(5RS,6SR,7SR)-6-Carboxy-2-ethylaminomethyl-5-(3,4-methylenedioxyphenyl)-7-(4-methoxyphenyl)cyclopenteno[1,2-b]pyridine

EXAMPLE 25

(5RS,6SR,7SR)-6-Carboxy-5-(3,4-methylenedioxyphenyl)-7-(4-methoxyphenyl)cyclopenteno[1,2-b]pyridine N-oxide To a chloroform-methanol (10:1) solution (2.8 ml) of (5RS,6SR,7SR)-6-carboxy-5-(3,4-methylenedioxyphenyl)-7-(4-methoxyphenyl)cyclopenteno[1,2-b]pyridine (27.3 mg, 0.0701 mmol) which was prepared in Example 2 was added mCPBA (24.1 mg, 0.14 mmol) at room temperature and the mixture was stirred at the same temperature for 9 h. The reaction mixture was concentrated under reduced pressure and the residue was purified by preparative TLC (E. Merck Kieselgel 60 F$_{254}$/chloroform:methanol:acetic acid=30:1:1) to give a solid, which was partitioned between dichloromethane (20 ml) and water (2 ml). The organic layer was dried over Na$_2$SO$_4$, filtered, and concentrated under reduced pressure to give (5RS,6SR,7SR)-6-carboxy-5-(3,4-methylenedioxyphenyl)-7-(4-methoxyphenyl)cyclopenteno[1,2-b]pyridine N-oxide (21.9 mg) as a pale purple powder.

mp: 130°–134° C.

FAB-MS(m/e,$(C_{23}H_{19}NO_6+H)^+$): 406

$^1$H-NMR(300 MHz,CDCl$_3$,δ ppm): 3.24(1H,t,J=5.1 Hz), 3.77(3H,s),4.87(1H,d,J=5.1 Hz), 5.01(1H,d,J=5.1 Hz),5.91 (2H,s),6.65–6.61(2H,m), 6.67–6.73(1H,m),6.82–6.88(2H, m),7.10–7.16(2H,m), 7.23(1H,d,J=7.8 Hz),7.31(1H,dd,J= 6.4 Hz,7.8 Hz), 8.20(1H,d,J=6.4 Hz)

Rf Value: 0.28 (E. Merck, Kieselgel 60 F$_{254}$/chloroform:methanol:acetic acid=30:1:1)

EXAMPLE 26

(5RS,6SR,7SR)-6-Carbamoyl-5-(3,4-methylenedioxyphenyl)-7-(4-methoxyphenyl)cyclopenteno[1,2-b]pyridine (5RS,6SR,7SR)-6-carboxy-5-(3,4-methylenedioxyphenyl)-7-(4-methoxyphenyl)cyclopenteno[1,2-b]pyridine (27.3 mg, 0.0701 mmol) which was prepared in Example 2, HOBT.H$_2$O (10.7 mg, 0.0700 mmol) and ammonium chloride (7.5 mg, 0.14 mmol) were suspended in DMF (0.70 ml). To the suspension were added EDCI.HCl (16.1 mg, 0.084 mmol) and TEA (20 μl, 0.14 mmol) under ice-cooling. The resulting mixture was stirred at room temperature for 3.5 h. Dichloromethane (0.70 ml) was added to the suspension and the mixture was additionally stirred at room temperature for 1.5 h. The reaction mixture was concentrated under reduced pressure and the residue was dissolved in AcOEt. The solution was washed with water (2 ml) and brine (2 ml), dried over Na$_2$SO$_4$, filtered, and concentrated under reduced pressure. The residue was purified by preparative TLC (E. Merck Kieselgel 60 F$_{254}$/chloroform:methanol=10:1) to give (5RS,6SR,7SR)-6-carbamoyl-5-(3,4-methylenedioxyphenyl)-7-(4-methoxyphenyl)cyclopenteno[1,2-b]pyridine (25.5 mg) as a colorless powder.

mp: 200°–203° C.

FAB-MS(m/e,$(C_{23}H_{20}N_2O_4+H)^+$): 389

$^1$H-NMR(300 MHz,CDCl$_3$,δ ppm): 3.01(1H,t,J=10.1 Hz),3.80(3H,s), 4.67(1H,d,J=10.1 Hz),4.69(1H,d,J=10.1 Hz), 4.91(1H,brs),5.23(1H,brs),5.94–6.00(2H,m), 6.72–6.74(1H,m),6.79–6.82(2H,m),6.88–6.94(2H,m), 7.09–7.15(1H,m),7.18–7.23(2H,m),7.28–7.34(1H,m), 8.44–8.48(1H,m)

Rf Value: 0.66 (E. Merck, Kieselgel 60 F$_{254}$/chloroform:methanol=10:1)

EXAMPLE 27

(5RS,6SR,7SR)-6-Methanesulfonylaminocarbonyl-5-(3,4-methylenedioxyphenyl)-7-(4-methoxyphenyl)cyclopenteno[1,2-b]pyridine (5RS,6SR,7SR)-6-carboxy-5-(3,4-methylenedioxyphenyl)-7-(4-methoxyphenyl)cyclopenteno

[1,2-b]pyridine (23.4 mg, 0.0601 mmol) which was prepared in Example 2, methanesulfonic amide (14.4 mg, 0.151 mmol), and DMAP (8.8 mg, 0.72 mmol) were dissolved in DMF (0.60 ml). To the solution was added EDCI.HCl (40.4 mg, 0.21 mmol) under ice-cooling. The resulting mixture was stirred at room temperature for 78 h. The solvent was removed in vacuo and the residue was partitioned between AcOEt and water. The aqueous layer was extracted with AcOEt. The combined organic layer was dried over $Na_2SO_4$, filtered, and concentrated under reduced pressure. The residue was purified by preparative TLC (E. Merck Kieselgel 60 $F_{254}$/chloroform:methanol=10:1) to give (5RS,6SR,7SR)-6-methanesulfonylaminocarbonyl-5-(3,4-methylenedioxyphenyl)-7-(4-methoxyphenyl)cyclopenteno [1,2-b]pyridine (17.0 mg) as a colorless powder.

mp: 113°–118° C.

FAB-MS(m/e $(C_{24}H_{22}N_2O_6S+H)^+$): 467

$^1$H-NMR(300 MHz,CDCl$_3$,δ ppm): 3.06(1H,t,J=10.1 Hz),3.21(3H,s),3.81(3H,s), 4.69(2H,d,J=10.0 Hz),5.95–6.05 (2H,m), 6.68–6.86(3H,m),6.90–6.98(2H,m),7.12–7.16(1H, m), 7.16–7.22(2H,m),7.28–7.34(1H,m),8.44–8.50(1H,m)

Rf Value: 0.58 (E. Merck, Kieselgel 60 $F_{254}$/chloroform:methanol=10:1)

EXAMPLE 28

(5RS,6SR,7SR)-6-(4-Isopropylbenzenesulfonylaminocarbonyl)-5-(3,4-methylenedioxyphenyl)-7-(4-methoxyphenyl) cyclopenteno[1,2-b]pyridine This compound was prepared using 4-isopropylbenzenesulfonamide in the same manner as in Example 27.

mp: 104°–110° C.

FAB-MS(m/e,$(C_{32}H_{30}N_2O_6S+H)^+$): 571

$^1$H-NMR(300 MHz,CDCl$_3$,δ ppm): 1.31(6H,d,J=6.9 Hz), 2.94(1H,t,J=10.2 Hz), 3.04(1H,sept,J=6.9 Hz),3.82(3H,s), 4.51(1H,d,J=10.2 Hz),4.54(1H,d,J=10.2 Hz), 5.95–6.02(2H, m),6.57(1H,d,J=1.7 Hz), 6.62(1H,dd,J=1.7 Hz,8.0 Hz),6.77 (1H,d,J=8.0 Hz), 6.84–6.92(2H,m),6.96–7.04(2H,m), 7.08–7.14(1H,m), 7.24–7.30(1H,m),7.40–7.46(2H,m), 7.87–7.93(2H,m), 8.42–8.46(1H,m)

Rf Value: 0.69 (E. Merck, Kieselgel 60 $F_{254}$/chloroform:methanol=10:1)

EXAMPLE 29

6-Carboxy-5-hydroxy-5-(3,4-methylenedioxyphenyl)-7-(4-methoxyphenyl) cyclopent-1,4-dieno[1,2-b]pyridine The title compound was prepared using 6-ethoxycarbonyl-5-hydroxy-5-(3,4-methylenedioxyphenyl)-7-(4-methoxyphenyl)cyclopent-1,3-dieno[2,1-b]pyridine which was prepared in Example 1-(4) in the same manner as in Example 2.

$^1$H-NMR(300 MHz,CDCl$_3$,δ ppm): 3.88(3H,s),5.90–5.95 (2H,m),6.74(1H,d,J=8.1 Hz), 6.97(1H,d,J=2.2 Hz), 7.00–7.05(3H,m), 7.16(1H,dd,J=4.9 Hz,7.6 Hz), 7.57(1H, dd,J=1.5 Hz,7.6 Hz), 8.55(1H,dd,J=1.5 Hz,4.9 Hz)

EXAMPLE 30

(5RS,6SR,7SR)-6-Carboxy-7-(2-carboxymethoxy-4-methoxyphenyl)-5-(3,4-methylenedioxyphenyl) cyclopeneno-[1,2-b]pyridine (1) 2-(2-Benzyloxy-4-methoxyphenylcarbonyl)-3-pyridine carboxylic acid To a THF (20 ml) solution of pyridine-2,3-dicarboxylic acid anhydride (1.92 g, 12.9 mmol) was added a THF solution of 2-benzyloxy-4-methoxyphenyllithium (10 ml), which was prepared from 2-benzyloxy-4-methoxyphenyl bromide (3.77 g, 12.9 mmol) and BuLi (1.6M hexane solution, 8.85 ml, 14.2 mmol) at –78° C., at –78° C. over a period of 5 min. The temperature of the mixture was raised to room temperature and the mixture was additionally stirred at the same temperature for 2 h. The reaction mixture was concentrated under reduced pressure and the residue was partitioned between 1N HCl and AcOEt. The organic layer was washed with 1N HCl, dried over $Na_2SO_4$, filtered, and concentrated under reduced pressure. The residue was dissolved in 1N NaOH and the solution was washed with AcOEt and chloroform. The aqueous layer was acidified with conc. HCl and extracted with AcOEt. The AcOEt layer was washed with 1N HCl and brine, dried over $Na_2SO_4$, filtered, and concentrated under reduced pressure. The residue was recrystallized from chloroform and chloroform-ether to give 2-(2-benzyloxy-4-methoxyphenylcarbonyl)-3-pyridine carboxylic acid (2.03 g) as a colorless solid.

(2) 6-Ethoxycarbonyl-7-(2-hydroxy-4-methoxyphenyl)-5-(3,4-methylenedioxyphenyl)cyclopenteno[1,2-b]pyridine The title compound was prepared using 2-(2-benzyloxy-4-methoxyphenylcarbonyl)-3-pyridine carboxylic acid which was prepared in (1), in the same manner as in Example 1-(2)-(5).

(3) 6-Ethoxycarbonyl-7-(2-ethoxycarbonylmethoxy-4-methoxyphenyl)-5-(3,4-methylenedioxyphenyl) cyclopenteno[1,2-b]pyridine To a DMF (1 ml) solution of 6-ethoxy-carbonyl-7-(2-hydroxy-4-methoxyphenyl)-5-(3,4-methylenedioxyphenyl) cyclopenteno[1,2-b]pyridine (15 mg, 0.035 mmol) was added a DMF (1.0 ml) suspension of NaH (1.60 mg, 0.040 mmol) under ice-cooling. The mixture was stirred under ice-cooling for 30 min, and at room temperature for 30 min. To the solution was added ethyl bromoacetate (5.74 µl, 0.052 mmol). The mixture was stirred at room temperature for 12 h and then at 50° C. for 3.5 h. 1N HCl was added to the solution and the mixture was partitioned between chloroform and water. The organic layer was washed with 1N HCl, a saturated aqueous solution of $NaHCO_3$ and brine, dried over $Na_2SO_4$, filtered, and concentrated under reduced pressure. The residue was purified by preparative TLC (E. Merck Kieselgel 60 $F_{254}$/hexane:AcOEt=1:1) to give 6-ethoxycarbonyl-7-(2-ethoxycarbonylmethoxy-4-methoxyphenyl)-5-(3,4-methylenedioxyphenyl) cyclopenteno[1,2-b]pyridine (8.8 mg) as a pale yellow solid.

(4) To a methanol (0.5 ml) solution of 6-ethoxycarbonyl-7-(2-ethoxycarbonylmethoxy-4-methoxyphenyl)-5-(3,4-methylenedioxyphenyl)cyclopenteno[1,2-b]pyridine (8.8 mg, 0.017 mmol) was added 4N NaOH (41.4 µl, 0.17 mmol) and the solution was stirred at room temperature for 3 days. The reaction mixture was diluted with water and washed with AcOEt. The pH value of the aqueous layer was turned to 2–3 and the aqueous layer was extracted with AcOEt. The organic layer was washed with 1N HCl and brine, dried over $Na_2SO_4$, filtered, and concentrated under reduced pressure. The residue was dried in vacuo to give (5RS,6SR,7SR)-6-carboxy-7-(2-carboxymethoxy-4-methoxyphenyl)-5-(3,4-methylenedioxyphenyl)cyclopenteno[1,2-b]pyridine (4.9 mg) as an orange powder.

mp: 154°–156° C.

High Resolution FAB-MS(m/e,$(C_{25}H_{21}NO_8+H)^+$): Calcd: 464.1345 Found: 464.1356

$^1$H-NMR(300 MHz,CDCl$_3$/CD$_3$OD=4/1,δ ppm): 3.66 (1H,t,J=10.3 Hz),3.80(3H,s), 4.60(2H,ABq,J=16.4 Hz,Δv=

47.0 Hz), 4.67(1H,d,J=10.3 Hz),5.10(1H,d,J=10.3 Hz), 5.97 (2H,S),6.50(1H,d,J=2.0 Hz), 6.55(1H,dd,J=2.5 Hz,8.3 Hz), 6.76(1H,s),6.80(2H,s), 7.18(1H,d,J=8.3 Hz),7.28(1H,dd,J= 5.5 Hz,7.7 Hz), 7.48(1H,td,J=1.4 Hz,7.7 Hz),8.32(1H,dd,J= 1.4 Hz,5.5 Hz)

Rf Value: 0.24 (E. Merck, Kieselgel 60 $F_{254}$/chloroform:methanol:acetic acid=10:1:1)

EXAMPLE 31

(5RS,6SR,7RS)-6-carboxy-5-(2-carboxymethoxy-4-methoxyphenyl)-7-(3,4-methylenedioxyphenyl)cyclopenteno-[1,2-c]pyridine The title compound was prepared using pyridine-3,4-dicarboxylic acid anhydride in the same manner as in Example 30.

EXAMPLE 32

(5RS,6SR,7SR)-6-carboxy-7-(2-hydroxy-4-methoxyphenyl)-5-(3,4-methylenedioxyphenyl)cyclopenteno-[1,2-b]pyridine The title compound was prepared using 6-ethoxycarbonyl-7-(2-hydroxy-4-methoxyphenyl)-5-(3,4-methylenedioxyphenyl)cyclopenteno[1,2-b]pyridine which was prepared in Example 30-(2) in the same manner as in Example 2.

EXAMPLE 33

(5RS,6SR,7SR)-6-carboxy-7-[2-(2-hydroxyethoxy)-4-methoxyphenyl]-5-(3,4-methylenedioxyphenyl)cyclopenteno-[1,2-b]pyridine The title compound was prepared using 2-(tert-butyldimethylsiloxy)ethylbromide the same manner as in Examples 30-(3) and (4).

EXAMPLE 34

(5RS,6SR,7SR)-6-carboxy-7-[2-(2-methylaminoethoxy)-4-methoxyphenyl]-5-(3,4-methylenedioxyphenyl)cyclopenteno[1,2-b]pyridine 6-Ethoxycarbonyl-7-[2-(2-hydroxyethoxy)-4-methoxyphenyl]-5-(3,4-methylenedioxyphenyl)cyclopenteno[1,2-b]-pyridine which was prepared in Example 33 was converted to the corresponding tosylate according to a conventional method and the tosylate was treated with methylamine. The resulting methylamino derivative was hydrolyzed in the same manner as in Example 2 to give (5RS,6SR,7SR)-6-carboxy-7-[2-(2-methylaminoethoxy)-4-methoxyphenyl]-5-(3,4-methylenedioxyphenyl)cyclopenteno[1,2-b]pyridine.

Each Compound in the following Examples 35–45 was prepared by the procedures given above.

EXAMPLE 35

(5RS,6SR,7SR)-6-Carboxy-2-ethoxymethyl-7-(4-methoxyphenyl)-5-(3,4-methylenedioxyphenyl)cyclopenteno[1,2-b]-pyridine

EXAMPLE 36

(5RS,6SR,7SR)-6-Carboxy-7-(4-methoxyphenyl)-5-(3,4-methylenedioxyphenyl)-2-propylcyclopenteno[1,2-b]-pyridine

EXAMPLE 37

(5RS,6SR,7SR)-6-Carboxy-2-isobutyl-7-(4-methoxyphenyl)-5-(3,4-methylenedioxyphenyl)cyclopenteno[1,2-b]-pyridine

EXAMPLE 38

6-Carboxy-7-hydroxy-7-(4-methoxyphenyl)5-3,4-methylenedioxyphenyl)cyclopent-1,3-dieno[1,2-b]pyridine

EXAMPLE 39

6-Carboxy-5-hydroxy-7-(4-methoxyphenyl-5-(3,4-methylenedioxyphenyl)-2-propylcyclopent-1,3-dieno-[2,1b]pyridine

EXAMPLE 40

(5RS,6SR,7RS)-6-Carboxy-5-hydroxy-7-(4-methoxyphenyl)-5-(3,4-methylenedioxyphenyl)cyclopenteno[1,2-b]-pyridine

EXAMPLE 41

(5RS,6SR,7SR)-6-Carboxy-7-(4-hydroxyphenyl)-5-(3,4-methylenedioxyphenyl)cyclopenteno[1,2-b]pyridine

EXAMPLE 42

(5RS,6SR,7RS)-6-Carboxy-7-[4-(2-hydroxyethoxy)phenyl]-5-(3,4-methylenedioxyphenyl)cyclopenteno[1,2-b]-pyridine

EXAMPLE 43

(5RS,6SR,7SR)-6-Carboxy-7-[4-(2-methylaminoethoxy)phenyl]-5-(3,4-methylenedioxyphenyl)cyclopenteno[1,2-b]-pyridine

EXAMPLE 44

(5RS,6SR,7SR)-6-Carboxy-7-(4-hydroxymethylphenyl)-5-(3,4-methylenedioxyphenyl)cyclopenteno[1,2-b]pyridine

EXAMPLE 45

(5RS,6SR,7SR)-6-Carboxy-5-(3,4-methylenedioxyphenyl)-7-(3-thienyl)cyclopenteno[1,2-b]pyridine

EXAMPLE 46

(5RS,6SR,7RS)-7-(4-Methoxyphenyl)-5-(3,4-methylenedioxyphenyl)-6-(2-oxo-3H-1,2,3,5-oxathiadiazol-4-yl)cyclopenteno[1,2-b]pyridine The title compound was prepared using (5RS,6SR,7SR)-6-carbamoyl-7-(4-methoxyphenyl)-5-(3,4-methylenedioxyphenyl)cyclopenteno[1,2-b]pyridine which was prepared in Example 26 as a starting material by the method described in the literature (J. Med. Chem. 1993, 36, 2485–2493).

EXAMPLE 47

(5RS,6SR,7SR)-6-(5-Oxo-4H-1,2,4-oxadiazol-3-yl)-5-(3,4-methylenedioxyphenyl)-7-(4-methoxyphenyl)cyclopenteno[1,2-b]pyridine The title compound was prepared using (5RS,6SR,7SR)-6-carbamoyl-5-(3,4-methylenedioxyphenyl)-7-(4-methoxyphenyl)cyclopenteno[1,2-b]pyridine which was prepared in Example 26 as a starting material by the method described in the literature(J. Med. Chem.,1993,36, 3691–3698).

mp: 251°–255° C.

High Resolution FAB-MS(m/e, $(C_{24}H_{19}N_3O_5+H)^+$): Calcd: 430.1403 Found: 430.1400

$^1$H-NMR(300 MHz, DMSO-d$_6$, δ ppm): 3.32(1H, t, J=10.8 Hz), 3.74(3H, s), 4.53(1H, d, J=10.8 Hz), 4.60(1H, d, J=10.8 Hz), 6.02(2H, s), 6.77(1H, dd, J=2.3 Hz, 7.8 Hz), 6.89(2H, d, J=8.7 Hz), 6.90(1H, d, J=7.8 Hz), 6.91(1H, d, J=2.3 Hz), 7.18(2H, d, J=8.7 Hz), 7.25(1H, dd, J=4.7 Hz, 7.7 Hz), 7.31(1H, d, J=7.7 Hz), 8.39(1H, d, J=4.7 Hz), 12.56 (1H, brs)

Rf Value: 0.21(E. Merck, Kieselgel 60F$_{254}$/ dichloromethane:methanol=20:1)

EXAMPLE 48

(5RS,6SR,7SR)-6-Tetrazol-5-(3,4-methylenedioxyphenyl-7-(4-methoxyphenyl) cyclopenteno[1,2-b]pyridine The title compound was prepared using (5RS,6SR,7SR) -6-carbamoyl-5-(3,4-methylenedioxyphenyl)-7-(4-methoxyphenyl)cyclopenteno[1,2-b]pyridine which was prepared in Example 26 as a starting material by the method described in the literature(J.Org.Chem., 1991.56, 2400-2404).

mp: 264°-266° C.

High Resolution FAB-MS(m/e, (C$_{23}$H$_{19}$N$_5$O$_3$+H)$^+$): Calcd: 414.1566 Found: 414.1561

$^1$H-NMR(300 MHz, DMSO-d$_6$, δ ppm): 3.71(3H, s), 3.86(1H, t, J=10.9 Hz), 4.63(1H, d, J=10.9 Hz), 4.71(1H, d, J=10.9 Hz), 6.00(2H, s), 6.66(1H, dd, J=1.7 Hz, 8.0 Hz), 6.85(1H, d, J=1.7 Hz), 6.85(2H, d, J=8.6 Hz), 6.85(1H, d, J=8.0 Hz), 7.11(2H, d, J=8.6 Hz), 7.25(1H, dd, J=4.6 Hz, 7.7 Hz), 7.30(1H, dd, J=1.8 Hz, 7.7 Hz), 8.40(1H, dd, J=1.8 Hz, 4.6 Hz)

Rf Value: 0.23(E. Merck, Kieselgel 60F$_{254}$/ dichloromethane:methanol=10:1)

EXAMPLE 49

(5RS,6SR,7SR)-5-(3,4-methylenedioxyphenyl)-6-methoxycarbonyl-7-(4-methoxyphenyl)cyclopenteno [1,2-b]pyridine To a DMF solution (1 ml) of sodium salt of (5RS,6SR,7SR)-6-carboxy-5-(3,4-methylenedioxyphenyl)-7-(4-methoxyphenyl)cyclopenteno[1,2-b]pyridine which was prepared in Example 2 was added methanol(15 l),EDCl.HCl (21 mg) and DMPA(2 mg) were added to the solution and the reaction solution was stirred at room temperature for 12 h, and partitioned between AcOEt and 10% citric acid. The organic layer was washed with a saturated aqueous solution of NaHCO$_3$ and brine, dried over MgSO$_4$ and concentrated under reduced pressure to give the title compound(20.2 mg) as a colorless powder.

mp: 140°-141.5° C.

High ResolutionFAB-MS(m/e, (C$_{24}$H$_{21}$NO$_6$+H)$^+$): Calcd: 404.1498 Found: 404.1510

$^1$H-NMR(300 MHz, CDCl$_3$, δ ppm): 3.27(1H, t, J=10.0 Hz), 3.64(3H, s), 3.80(3H, s), 4.59(1H, d, J=10.0 Hz), 4.67(1H, d, J=10.0 Hz), 5.92–6.01(2H, m), 6.66–6.83(3H, m), 6.90(2H, d, J=8.5 Hz), 7.09–7.20(1H, m), 7.16(2H, d, J=8.5 Hz), 7.29(1H, d, J=7.9 Hz), 8.46(1H, d, J=4.6 Hz)

Rf Value: 0.42(E. Merck, Kieselgel 60F$_{254}$/ hexane:AcOEt=1:1)

EXAMPLE 50

(5RS,6SR,7SR)-7-(2-Ethoxycarbonylmethoxy-4-methoxyphenyl)-6-carboxy-5-(3,4-methylenedioxyphenyl)cyclopenteno[1,2-b]pyridine (1) 5-Oxo-6-tert-butoxycarbonyl-7-(2-benzyloxy-4-methoxyphenyl)cyclopent-1,3-dieno[2,1-b]pyridine To a DMF(110 mg) suspension of 2-(2-benzyloxy-4-methoxyphenylcarbonyl)-3-pyridine carboxylic acid which was prepared in Example 30-(1) was added CDI(10.3 g) under ice-cooling. The mixture was stirred under ice-cooling for 1.5 h and at room temperature for 1 h, and partitioned between AcOEt and water. The aqueous layer was extracted with AcOEt, the combined organic layer was washed with water and brine, dried over MgSO$_4$ and evaporated to give a solid residue. The residue was dissolved in THF(350 ml), then cooled at −78° C. To the solution was added dropwise THF solution of lithium enolate of acetic acid tert-butyl ester which was prepared from acetic acid tert-butyl ester(14 ml) and LDA(1.7M,61 ml). The reaction solution was stirred at −78° C. for 15 min, and 1N HCl(500 ml) was added. The mixture was extracted with AcOEt, washed with a saturated aqueous solution of NaHCO$_3$ and brine, dried over MgSO$_4$, and concentrated under reduced pressure. To a dichloromethane solution of the residue was added SiO$_2$ (Wako gel C-200, 140 g), and the mixture was stirred at room temperature, filtrated to remove SiO$_2$, then washed with dichloromethane and AcOEt. Filtrate and washings were combined and concentrated. The residue was purified by silica gel column chromatography(E. Merck Kieselgel 60/dichloromethane:acetone=100:1 to 50:1) to give 5-oxo- 6-tert-butoxycarbonyl-7-(2-benzyloxy-4-methoxyphenyl)cyclopent-1,3-dieno[2,1-b]pyridine(9.83 g) as a reddish orange solid.

(2) 5-Hydroxy-6-tert-butoxycarbonyl-7-(2-benzyloxy-4-methoxyphenyl)-5-(3,4-methylenedioxyphenyl)cyclopent-1,3-dieno[2,1-b]pyridine To a THF(100 ml) solution of 5-oxo-6-tert-butoxycarbonyl-7-(2-benzyloxy-4-methoxyphenyl) cyclopent-1,3-dieno[2,1-b]pyridine(10.8 g,25.5 mg) was added a THF solution(1.0M,28.0 ml) of 3,4-methylenedioxyphenylmagnesium bromide dropwise at −78° C. The solution was stirred at −78° C. for 45 min and the temperature of the solution was raised at room temperature after addition of a saturated aqueous solution of NH$_4$Cl (300 ml). The reaction solution was partitioned between AcOEt and water, and the aqueous layer was extracted with AcOEt. The combined organic layer was washed with a saturated aqueous solution of NaHCO$_3$ and brine, dried over MgSO$_4$, and concentrated under reduced pressure. The residue was recrystallized from AcOEt-hexane to give 5-hydroxy-6-tert-butoxycarbonyl-7-(2-benzyloxy-4-methoxyphenyl)-5-(3,4-methylenedioxyphenyl)cyclopent-1,3-dieno[2,1-b]pyridine(11.1 g) as a reddish orange solid.

(3) (5RS,6RS,7SR)-6-tert-butoxycarbonyl-7-(2-benzyloxy-4-methoxyphenyl)-5-(3,4-methylenedioxyphenyl)cyclopenteno[1,2-b]pyridine To a THF(100 ml)-ethanol(100 ml) solution of 5-hydroxy-6-tert-butoxycarbonyl-7-(2-benzyloxy-4-methoxyphenyl)-5-(3,4-methylenedioxyphenyl)cyclopent-1,3-dieno[2,1-b]pyridine(11.4 g, 20.1 mmol) was added zinc powders(9.87 g) under ice-cooling. A HCl-dioxane solution (4N,45.3 ml) was added dropwise to this suspension, and then a saturated aqueous solution of NaHCO$_3$(300 ml) and ethyl acetate were added to quench the reaction. Resulting precipitates were removed off by filtration, washed and extracted with AcOEt. The filtrate, washings and extracts were combined, washed with brine, dried over MgSO$_4$ and concentrated. The residue was crystallized from AcOEt-hexane to give (5RS,6RS,7SR)-6-tert-butoxycarbonyl-7-(2-benzyloxy-4-methoxyphenyl)-5-(3,4-methylendioxyphenyl)cyclo-penteno[1,2-b]pyridine as a light yellow solid.

(4) (5RS,6SR,7SR)-6-Tert-butoxycarbonyl-7-(2-benzyloxy-4-methoxyphenyl)-5-(3,4-methylendioxyphenyl)cyclopenteno[1,2-b]pyridine To a t-BuOH(60 ml)-1,4-dioxane(60 ml) solution of (5RS, 6RS,7SR)-6-tert-butoxycarbonyl-7-(2-benzyloxy-4-methoxyphenyl)-5-(3,4-methylenedioxyphenyl)cyclopenteno[1,2-b]pyridine(6.96 g,12.6 mmol) solution was added potassium tert-butoxide(0.15 g). The solution was stirred at 60° C. for 8 h and partitioned between water and AcOEt. The aqueous layer was extracted with AcOEt, and the organic layers were combined, washed with brine and dried over MgSO$_4$. After removal of the solvent under reduced pressure the residue was crystallized from ether and hexane to give (5RS,6SR,7SR)-6-tert-butoxycarbonyl-7-(2-benzyloxy-4-methoxyphenyl)-5-(3,4-methylendioxyphenyl)cyclopenteno[1,2-b]pyridine(6.07 g) as a colorless crystal.

(5) (5RS,6SR,7SR)-7-(2-Hydroxy-4-methoxyphenyl)-6-tert-butoxycarbonyl-5-(3,4-methylendioxyphenyl)cyclopenteno[1,2-b]pyridine To a THF(25 ml)-1,4-dioxane(25 ml) solution of (5RS, 6SR,7SR)-6-tert-butoxycarbonyl-7-(2-benzyl-4-methoxyphenyl)-5-(3,4-methylenedioxyphenyl)cyclopenteno[1,2-b]pyridine(2.68 g,4.86 mmol) was added a water suspension(5 ml) of Pd black under argon atmosphere. The reaction mixture was stirred under hydrogen atmosphere at room temperature for 12 h, filtrated to remove the catalyst and concentrated under reduced pressure. The residue was recrystallized from AcEOt-hexane to give (5RS, 6SR,7SR)-7-(2-hydroxy methoxyphenyl)-6-tert-butoxycarbonyl-5-(3,4-methylenedioxyphenyl)cyclopenteno[1,2-b]pyridine(2.11 g) as a colorless crystal.

(6) (5RS,6SR,7SR)-7-(2-Ethoxycarbonylmethoxy-4-methoxyphenyl)-6-tert-butoxycarbonyl-5-(3,4-methylendioxyphenyl)cyclopenteno[1,2-b]pyridine The title compound was prepared in the same manner as in Example 30-(3) using (5RS,6RS,7SR)-7-(2-Hydroxy-4-methoxyphenyl)-6-tert-butoxycarbonyl-5-(3,4-methylendioxyphenyl)cyclopenteno[1,2-b]pyridine.

(7) (5RS,6SR,7SR)-7-(2-Ethoxycarbonylmethoxy-4-methoxyphenyl)-6-carboxy-5-(3,4-methylendioxyphenyl)cyclopenteno[1,2-b]pyridine (5RS,6SR,7SR)-7-(2-Ethoxycarbonylmethoxy-4-methoxyphenyl)-6-tert-butoxycarbonyl-5-(3,4-methylendioxyphenyl)cyclopenteno[1,2-b]pyridine(15 mg,0.027 mmol) was treated with TFA(1 ml) under ice-cooling and stirred at room temperature for 1.5 h. The title compound was prepared by removing TFA under reduced pressure as a light yellow solid.

High ResolutionFAB-MS(m/e, $(C_{27}H_{25}NO_8+H)^+$): Calcd: 492.1659 Found: 492.1651

$^1$H-NMR(300 MHz, CDCl$_3$, δ ppm): 1.20(3H, t, J=7.1 Hz), 3.77(3H, s), 3.84(1H, t, J=10.3 Hz), 4.01–4.18(2H, m), 4.36(1H, d, J=15.5 Hz), 4.46(1H, d, J=15.5 Hz), 4.70(1H, d, J=10.3 Hz), 5.02(1H, d, J=10.3 Hz), 5.95(1H, d, J=1.4 Hz), 5.97(1H, d, J=1.4 Hz), 6.33(1H, d, J=2.2 Hz), 6.48(1H, dd, J=2.2 Hz, 8.2 Hz), 6.78(1H, d, J=8.5 Hz), 6.84(1H, s), 6.84(1H, d, J=8.5 Hz), 7.22(1H, d, J=8.2 Hz), 7.53(1H, dd, J=5.7 Hz, 7.7 Hz), 7.81(1H, d, J=7.7 Hz), 8.39(1H, d, J=5.7 Hz)

Rf Value: 0.32(E. Merck, Kieselgel 60F$_{254}$/chloroform:methanol=10:1)

EXAMPLE 51

(5RS,6SR,7SR)-6-Carboxy-7-[2-(tetrazol-5-ylaminocarbonylmethoxy)-4-methoxyphenyl]-5-(3, 4-methylendioxyphenyl)cyclopenteno[1,2-b]pyridine (1) (5RS,6SR,7SR)-7-(2-Carboxymethoxy-4-methoxyphenyl)-6-tert-butoxycarbonyl-5-(3,4-methylenedioxyphenyl)cyclopenteno[1,2-b]pyridine To a methanol solution(4 ml) of (5RS,6SR,7SR)-7-(2ethoxycarbonylmethoxy-4-methoxyphenyl)-6-tert-butoxycarbonyl-5-(3,4-methylenedioxyphenyl)cyclopenteno[1,2-b]pyridine(263 mg,0.480 mmol) which was prepared in Example 50-(6) was added 6N NaOH(500 μl) at 0° C. The mixture was stirred at room temperature for 1 h and concentrated under reduced pressure. The residue was acidified with 3N HCl, and extracted with AcOEt. The organic layer was washed with brine, dried over Na$_2$SO$_4$ and concentrated under reduced pressure to give (5RS,6SR,7SR)-7-(2-carboxymethoxy-4-methoxyphenyl)-6-tert-butoxycarbonyl-5-(3,4-methylenedioxyphenyl)cyclopenteno[1,2-b]pyridine(248 mg).

(2) (5RS,6SR,7SR)-7-[2-Tetrazol-5-ylaminocarbonylmethoxy)-4-methoxyphenyl]-6-tert-butoxycarbonyl-5-(3,4-methylendioxyphenyl)cyclopenteno[1,2-b]pyridine To a THF(1 ml) solution of (5RS,6SR,7SR)-7-(2-carboxymethoxy-4-methoxyphenyl)-6-tert-butoxycarbonyl-5-(3,4-methylenedioxyphenyl)cyclopenteno[1,2-b]pyridine(64 mg,0.123 mmol) was added CDI(20 mg) at room temperature and the mixture was stirred for 1 h. 5-Aminotetrazole(11 mg) was added to the solution at room temperature and the mixture was stirred at room temperature for 16 h. The reaction solution was diluted with AcOEt, washed with 1N HCl and brine, and dried over Na$_2$SO$_4$. After removal of the solvent under reduced pressure the residue was purified by preparative TLC(E. Merck Kieselgel 60F$_{254}$/chloroform: methanol:acetic acid=20:1:1) to give (5RS,6SR,7SR)-7-[2-(tetrazol-5-ylaminocarbonylmethoxy)-4-methoxyphenyl]-6-tert-butoxycarbonyl-5-(3,4-methylenedioxyphenyl)cyclopenteno[1,2-b]pyridine(73.1 mg).

(3) A solution of (5RS,6SR,7SR)-7-[2-(tetrazol-5-ylaminocarbonylmethoxy)-4-methoxyphenyl]-6-tert-butoxycarbonyl-5-(3,4-methylenedioxyphenyl)cyclopenteno[1,2-b]pyridine(61 mg) and thioanisole(0.15 ml) in TFA(3 ml) was stirred at room temperature for 1 h. After removal of the solvent the residue was crystallized from ether to give the title compound(39.2 mg) as a colorless powder.

mp: >220° C.(dec.)

High Resolution FAB-MS(m/e, $(C_{26}H_{22}N_6O_7+H)^+$): Calcd: 531.1628 Found: 531.1654

$^1$H-NMR(300 MHz, DMSO-d$_6$, δ ppm): 3.57(1H, t, J=10.2 Hz), 3.72(3H, s), 4.56(1H, d, J=10.2 Hz), 4.82(1H, d, J=14.8 Hz), 4.93(1H, d, J=10.2 Hz), 4.97(1H, d, J=14.8 Hz), 5.98(2H, d, J=2.6 Hz), 6.50–6.60(2H, m), 6.75–6.90(3H, m), 7.15–7.33(3H, m), 8.56(1H, brs), 12.43(1H, brs)

Rf Value: 0.29(E. Merck, Kieselgel 60F$_{254}$/chloroform:methanol:acetic acid=10:1:1)

EXAMPLE 52

(5RS,6SR,7SR)-7-(2-Carbamoylmethoxy-4-methoxyphenyl)-6-carboxy-5-(3,4-methylendioxyphenyl)cyclopenteno[1,2-b]pyridine (5RS,6SR,7SR)-7-(2-Carboxymethoxy-4-methoxyphenyl)-6-tert-butoxycarbonyl-5-(3,4-methylendioxyphenyl)cyclopenteno[1,2-b]pyridine which was prepared in Example 51-(1) was condensed with ammonium chloride in the same manner as in Example 26 and the tert-butyl group was cleaved with TFA to give the title compound.

mp: 138°–139.5° C.

High Resolution FAB-MS(m/e, $(C_{25}H_{22}N_2O_7+H)^+$): Calcd: 463.1505 Found: 463.1501

$^1$H NMR(300 MHz, DMSO-$d_6$, δ ppm): 3.37(1H, t, J=10.0 Hz), 3.74(3H, s), 4.40(2H, s), 4.53(1H, d, J=10.0 Hz), 4.90(1H, d, J=10.0 Hz), 6.00(2H, s), 6.51(1H, d, J=2.9 Hz), 6.52(1H, dd, J=2.9 Hz, 8.2 Hz), 6.77(1H, dd, J=1.6 Hz, 7.8 Hz), 6.83(1H, d, J=1.6 Hz), 6.89(1H, d, J=7.8 Hz), 7.10(1H, d, J=8.2 Hz), 7.17(1H, dd, J=4.6 Hz, 7.5 Hz), 7.23(1H, dd, J=1.9 Hz, 7.5 Hz), 7.26(1H, brs), 7.41(1H, brs), 8.25(1H, dd, J=1.9 Hz, 4.6 Hz)

Rf Value: 0.37(E. Merck, Kieselgel 60F$_{254}$/chloroform:methanol=10:1)

EXAMPLE 53

(5RS,6SR,7SR)-6-carboxy-7-(2-methaneusulfonylaminocarbonylmethoxy-4-methoxyphenyl)-5-(3,4-methylenedioxyphenyl)cyclopenteno[1,2-b]pyridine (5RS,6SR,7SR)-7-(2-Carboxymethoxy-4-methoxyphenyl)-6-tert-butylcarbonyl-5-(3,4-methylenedioxyphenyl)cyclopenteno[1,2-b]pyridine which was prepared in Example 51-(1) was condensed with methanesulfoneamide in the same manner as in Example 27 and the tert-butyl group was cleaved with TFA to give the title compound.

mp: 143.5°–145° C.

High Resolution FAB-MS(m/e, $(C_{26}H_{24}N_2O_9S+H)^+$): Calcd: 541.1280 Found: 541.1282

$^1$H NMR(300 MHz, DMSO-$d_6$, δ ppm): 3.10(3H, s), 3.49(1H, t, J=10.2 Hz), 3.73(3H, s), 4.49(2H, ABq, J=16.3 Hz, Δν=61.3 Hz), 4.51(1H, d, J=10.2 Hz), 4.77(1H, d, J=10.2 Hz), 5.99(2H, s), 6.47(1H, d, J=2.4 Hz), 6.53(1H, dd, J=2.4 Hz, 8.4 Hz), 6.79(1H, dd, J=1.9 Hz, 8.0 Hz), 6.86(1H, d, J=1.9 Hz), 6.87(1H, d, J=8.0 Hz), 7.12(1H, d, J=8.4 Hz), 7.14–7.24(2H, m), 8.31(1H, d, J=4.9 Hz)

Rf Value: 0.27(E. Merck, Kieselgel 60F$_{254}$/chloroform:methanol=4:1)

EXAMPLE 54

(5RS,6SR,7SR)-6-Carboxy-7-[2-(tetrazol-5-ylmethoxy)-4-methoxyphenyl]-5-(3,4-methylenedioxyphenyl)cyclopenteno[1,2-b]pyridine (1) (5RS,6SR,7SR)-7-(2-Cyanomethoxy-4-methoxyphenyl)-6-tert-butoxycarbonyl-5-(3,4-methylenedioxyphenyl)cyclopenteno[1,2-b]pyridine (5RS,6SR,7SR)-7-(2-Hydroxy-4-methoxyphenyl)-6-tert-butoxycarbonyl-5-(3,4-methylenedioxyphenyl)cyclopenteno[1,2-b]pyridine which was prepared in Example 50-(5) was reacted with bromoacetonitrile in the same manner as in Example 50-(6) to give (5RS,6SR,7SR)-7-(2-cyanomethoxy-4-methoxyphenyl)-6-tert-butoxycarbonyl-5-(3,4-methylenedioxyphenyl)cyclopenteno[1,2-b]pyridine.

(2) (5RS,6SR,7SR)-7-[2-(tetrazol-5-ylmethoxy)-4-methoxyphenyl]-6-tert-butoxycarbonyl-5-(3,4-methylenedioxyphenyl)cyclopenteno[1,2-b]pyridine This compound was prepared in the same manner as in Example 48 using (5RS,6SR,7SR)-7-(2-cyanomethoxy-4-methoxyphenyl)-6-tert-butoxycarbonyl-5-(3,4-methylenedioxyphenyl) cyclopenteno[1,2-b]pyridine.

(3) The title compound was prepared by reacting (5RS,6SR,7SR)-7-[2-(tetrazol-5-ylmethoxy)-4-methoxyphenyl]-6-tert-butoxycarbonyl-5-(3,4-methylenedioxyphenyl) cyclopenteno[1,2-b]pyridine in THF at room temperature for 1.5 h.

mp: 155°–158° C.

High Resolution FAB-MS(m/e, $(C_{25}H_{21}N_5O_6+H)^+$): Calcd: 488.1570 Found: 488.1567

$^1$H-NMR(300 MHz, CDCl$_3$, δ ppm): 3.60(1H, dd, J=9.5 Hz, 10.6 Hz), 3.67(3H, s), 4.65(1H, d, J=9.5 Hz), 5.36(1H, d, J=10.6 Hz), 5.45(1H, d, J=15.3 Hz), 5.68(1H, d, J=15.3 Hz), 6.00(2H, s), 6.41(1H, d, J=1.9 Hz), 6.44(1H, dd, J=1.9 Hz, 8.5 Hz), 6.71(1H, d, J=1.6 Hz), 6.73(1H, dd, J=1.6 Hz, 7.9 Hz), 6.83(1H, d, J=7.9 Hz), 7.08(1H, d, J=8.5 Hz), 7.27(1H, dd, J=4.9 Hz, 7.6 Hz), 7.46(1H, d, J=7.6 Hz), 8.54(1H, d, J=4.9 Hz)

Rf Value: 0.26(E. Merck, Kieselgel 60F$_{254}$/chloroform:methanol:acetic acid=10:1:1)

EXAMPLE 55

(5RS,6SR,7SR)-6-Carboxy-7-[2-(1-methoxycarbonylpropoxy)-4-methoxyphenyl]-5-(3,4-methylenedioxyphenyl)cyclpenteno[1,2-b]pyridine (1) (5RS,6SR,7SR)-6-Tert-butoxycarbonyl-7-[2-(1-methoxycarbonylpropoxy)-4-methoxyphenyl]-5-3,4-methylenedioxyphenyl)cyclopenteno[1,2-b]pyridine To a methylethylketone(1.5 ml) solution of (5RS,6SR,7SR)-7-(2-hydroxy-4-methoxyphenyl)-6-tert-butoxycarbonyl-5-(3,4-methylenedioxyphenyl)cyclopenteno[1,2-b]pyridine(98.2 mg, 0.213 mmol), K$_2$CO$_3$ (48.8 mg) and KI(1.6 mg) was added 2-bromobutylic acid methyl ester(33 μl) and the solution was heated under reflux for 19.5 h. The reaction solution was partitioned between water and AcOEt, and organic layer was washed with brine and dried over Na$_2$SO$_4$. After removal of the solvent the residue was purified by silica gel column chromatography (E. Merck Kieselgel 60F$_{254}$/dichloromethane:AcOEt=3:1) and by preparative TLC(E. Merck Kieselgel 60F$_{254}$ dichloromethane:acetone=30:1) to give each of diastereomers (5RS,6SR,7SR)-6-tert-butoxycarbonyl-7-[2-(1-methoxycarbonylpropoxy)-4-methoxyphenyl]-5-(3,4-methylenedioxyphenyl)cyclopenteno[1,2-b]pyridine as a colorless amorphous solid. The yield of one of diastereomers is 56.2 mg and the other 38.8 mg.

(2) One of the diastereomers(56.2 mg, 0.100 mmol)which was prepared in (1) was dissolved under ice-cooling in TFA(2 ml) and the solution was stirred under ice-cooling to room temperature for 3.5 h. After removal of TFA the residue was neutrallized with a saturated aqueous solution of NaHCO$_3$, and the pH of suspension was adjusted at approximately 5. The suspension was extracted with AcOEt, washed with brine and dried over Na$_2$SO$_4$. After removal of the solvent the residue was purified by preparative TLC(E. Merck Kieselgel 60F$_{254}$ dichloromethane:acetone=4:1) to give one of diastereomers of title compound(45.3 mg) as a colorless amorphous solid.

mp: 85°–123° C.

High Resolution FAB-MS(m/e, $(C_{28}H_{27}NO_8+H)^+$): Calcd: 506.1815 Found: 506.1803

$^1$H-NMR(300 MHz, CDCl$_3$, δ ppm): 0.56(3H, t, J=7.4 Hz), 1.34–1.76(2H, m), 3.67(3H, s), 3.76(3H, s), 4.05(1H, t, J=10.5 Hz), 4.51(1H, dd, J=5.1 Hz, 8.1 Hz), 4.60(1H, d, J=10.5 Hz), 4.72(1H, d, J=10.5 Hz), 5.96(2H, s), 6.33(1H, d, J=2.3 Hz), 6.51(1H, dd, J=2.3 Hz, 8.3 Hz), 6.79(1H, d, J=7.7 Hz), 6.83(1H, d, J=1.6 Hz), 6.84(1H, dd, J=1.6 Hz, 7.7 Hz), 7.07(1H, dd, J=4.9 Hz, 7.6 Hz), 7.22(1H, d, J=8.3 Hz), 7.25(1H, d, J=7.6 Hz), 8.39(1H, d, J=4.9 Hz)

Rf Value:0.25(E. Merck, Kieselgel 60F$_{254}$/dichloromethane:acetone=3:1)

EXAMPLE 56

(5RS,6SR,7SR)-6-Carboxy-7-[2-(1-methoxycarbonylpropoxy)-4-methoxyphenyl]-5-(3,4-methylenedioxyphenyl)cyclopenteno[1,2-b]pyridine(the other diastereomer)

The other diastereomer(38.8 mg,00.691 mmol) which was prepared in Example 55-(2) was subjected to the same reaction as in Example 55-(2) to give the other diastereomer of title compound(31.5 mg) as a colorless amorphous solid.

mp: 94°–102° C.

High Resolution FAB-MS(m/e, $(C_{28}H_{27}NO_8+H)^+$): Calcd: 506.1815 Found: 506.1790

$^1$H-NMR(300 MHz, $CDCl_3$, δ ppm): 0.99(3H, t, J=7.4 Hz), 1.85–2.01(2H, m), 3.22(1H, t, J=10.0 Hz), 3.71(3H, s), 3.75(3H, s), 4.61(1H, t, J=6.6 Hz), 4.69(1H, d, J=10.0 Hz), 5.09(1H, d, J=10.0 Hz), 5.94(1H, d, J=2.0 Hz), 5.95(1H, d, J=2.0 Hz), 6.27(1H, d, J=2.1 Hz), 6.50(1H, dd, J=2.1 Hz, 8.3 Hz), 6.71(1H, s), 6.77(2H, s), 7.04(1H, d, J=8.3 Hz), 7.13 (1H, dd, J=5.1 Hz, 7.4 Hz), 7.33(1H, d, J=7.4 Hz), 8.48(1H, d, J=5.1 Hz)

Rf Value: 0.26(E. Merck, Kieselgel $60F_{254}$/dichloromethane:acetone=4:1)

EXAMPLE 57

(5RS,6SR,7SR)-6-Carboxy-7-[2-(1-carboxypropoxy)-4-methoxyphenyl]-5-(3,4-methylenedioxyphenyl)cyclopenteno[1,2-b]pyridine(one of diastereomers)

(5RS,6SR,7SR)-6-Carboxy-7-[2-(1-methoxycarbonylpropoxy)-4-methoxyphenyl]-5-(3,4-methylenedioxyphenyl)cyclopenteno[1,2-b]pyridine(one of diastereomers) which was prepared in Example 55 was subjected to the same reaction as in Example 30-(4) to give the title compound.

mp: 151°–154° C.

High Resolution FAB-MS(m/e, $(C_{27}H_{25}NO_8+H)^+$): Calcd: 492.1658 Found: 492.1646

$^1$H-NMR(300 MHz, $CDCl_3$, δ ppm): 1.02(3H, t, J=7.4 Hz), 1.92–2.08(2H, m), 3.78(3H, s), 3.81(1H, dd, J=9.9 Hz, 11.4 Hz), 4.72(1H, d, J=9.9 Hz), 4.90(1H, dd, J=5.8 Hz, 6.3 Hz), 5.24(1H, d, J=11.4 Hz), 6.00(2H, s), 6.51(1H, dd, J=2.3 Hz, 8.6 Hz), 6.58(1H, d, J=2.3 Hz), 6.70(1H, d, J=1.7 Hz), 6.77(1H, dd, J=1.7 Hz, 7.9 Hz), 6.84(1H, d, J=7.9 Hz), 7.20(1H, dd, J=4.8 Hz, 7.5 Hz), 7.23(1H, d, J=8.6 Hz), 7.38(1H, d, J=7.5 Hz), 8.24(1H, d, J=4.8 Hz)

Rf Value: 0.32(E. Merck, Kieselgel $60F_{254}$/dichloromethane:methanol:acetic acid=10:1:1)

EXAMPLE 58

(5RS,6SR,7SR)-6-Carboxy-7-[2-(1-carboxypropoxy)-4-methoxyphenyl]-5-(3,4-methylendioxyphenyl)cyclopenteno[1,2-b]pyridine(the other diastereomer)

The title compound was prepared in the same manner as in Example 57.

mp: 141°–144° C.

High Resolution FAB-MS(m/e, $(C_{27}H_{25}NO_8+H)^+$): Calcd: 492.1658 Found: 492.1639

$^1$H-NMR(300 MHz, $CDCl_3$, δ ppm): 0.88(3H, t, J=7.5 Hz), 1.51–1.83(2H, m), 3.33(1H, t, J=10.8 Hz), 3.76(3H, s), 4.62(1H, d, J=10.8 Hz), 4.68(1H, dd, J=5.4 Hz, 6.9 Hz), 4.96(1H, d, J=10.8 Hz), 5.95(1H, d, J=1.6 Hz), 5.97(1H, d, J=1.6 Hz), 6.38(1H, d, J=2.0 Hz), 6.52(1H, dd, J=2.0 Hz, 8.4 Hz), 6.64(1H, d, J=1.7 Hz), 6.73(1H, dd, J=1.7 Hz, 7.9 Hz), 6.79(1H, d, J=7.9 Hz), 7.09(1H, d, J=8.4 Hz), 7.18(1H, dd, J=4.8 Hz, 7.7 Hz), 7.36(1H, d, J=7.7 Hz), 8.41(1H, d, J=4.8 Hz)

Rf Value: 0.25(E. Merck, Kieselgel $60F_{254}$/dichloromethane:methanol:acetic acid=10:1:1)

EXAMPLE 59

(5RS,6SR,7SR)-7-[2-(1-ethoxycarbonylethoxy)-4-methoxyphenyl]-6-carboxy-5-(3,4-methylenedioxyphenyl)cyclopenteno[1,2-b]pyridine The title compound was prepared in the same manner as in Example 55 as a colorless solid(diastereomer ratio=2:1)

High Resolution FAB-MS(m/e, $(C_{28}H_{27}NO_8+H)^+$): Calcd: 506.1815 Found: 506.1817

$^1$H-NMR(300 MHz, $CDCl_3$, δ ppm): 1.01, 1.53(3H, 2d, J=6.5 Hz, J=6.6 Hz), 1.18(3H, t, J=7.3 Hz), 3.24, 3.93(1H, 2t, J=10.0 Hz, J=10.5 Hz), 3.74(3H, s), 4.08–4.24(2H, m), 4.52–4.78, 5.08(3H, m, d, J=10.0 Hz), 5.95(2H, s), 6.30(1H, d, J=2.1 Hz), 6.50(1H, dd, J=2.1 Hz, 8.2 Hz), 6.69–6.90(3H, m), 6.97–7.38(3H, m), 8.37, 8.47(1H, 2d, J=5.1 Hz, J=4.6 Hz)

Rf Value: 0.36(E. Merck, Kieselgel $60F_{254}$/chloroform:methanol=10:1)

EXAMPLE 60

(5RS,6SR,7SR)-6-Carboxy-7-[2-(1-carboxyethoxy)-4-methoxyphenyl]-5-(3,4-methylenedioxyphenyl)cyclopenteno[1,2-b]pyridine The title compound was prepared in the same manner as in Example 57 using (5RS,6SR,7SR)-7-[2-(1-ethoxycarbonylethoxy)-4-methoxyphenyl]-6-carboxy-5-(3,4-methylenedioxyphenyl)cyclopenteno[1,2-b]pyridine(2:1 diastereomer mixture) as a colorless solid(diastereomer ratio=2:1).

High Resolution FAB-MS(m/e, $(C_{26}H_{23}NO_8+H)^+$): Calcd: 478.1502 Found: 478.1521

$^1$H-NMR(300 MHz, $CDCl_3$, δ ppm): 1.26, 1.62(3H, 2d, J=7.0 Hz), 3.38, 3.75(1H, t+dd, J=10.5 Hz, J=9.9 Hz, 11.2 Hz), 3.75, 3.77(3H, 2s), 4.60, 4.71(1H, 2d, J=10.5 Hz, J=9.9 Hz), 4.83, 5.03(1H, 2q, J=7.0 Hz), 4.92, 5.25(1H, 2d, J=10.5 Hz, J=11.2 Hz), 5.95, 5.96, 6.00(2H, d, J=1.9 Hz, d, J=1.9 Hz, s), 6.38–6.87(5H, m), 7.08–7.41(3H, m), 8.40, 8.28(1H, 2d, J=4.9 Hz)

Rf Value: 0.27, 0.17(E. Merck, Kieselgel $60F_{254}$/chloroform:methanol:acetic

EXAMPLE 61–63

(5RS,6SR,7SR)-6-Carboxy-7-[2-(2-carboxyethoxy)-4-methoxyphenyl]-5-(3,4-methylenedioxyphenyl)cyclopenteno[1,2-b]pyridine(Example 61)

(5RS,6SR,7SR)-6-Carboxy-7-[2-[2-(2-carboxyethoxycarbonyl)ethoxy]-4-methoxyphenyl]-5-(3,4-methylenedioxyphenyl)cyclopenteno[1,2-b]pyridine(Example 62)

(5RS,6SR,7SR)-6-Carboxy-7-[2-[2-[2-(2-carboxyethoxycarbonyl)ethoxycarbonyl]ethoxy]-4-methoxyphenyl]-5-(3,4-methylenedioxyphenyl)cyclopenteno[1,2-b]pyridine(Example 63)

These three compounds were prepared by reacting (5RS,6SR,7SR)-7-(2-hydroxy-4-methoxyphenyl)-6-tertbutoxycarbonyl-5-(3,4-methylenedioxyphenyl) cyclopenteno[1,2-b]pyridine with β-propiolactone, followed by purification by preparative TLC(E. Merck Kieselgel 60F₂₅₄/chloroform:methanol:acetic acid=20:1:1).

EXAMPLE 61

High Resolution FAB-MS(m/e, $(C_{26}H_{23}NO_8+H)^+$): Calcd: 478.1502 Found: 478.1491

$^1$H-NMR(300 MHz, CDCl₃, δ ppm): 2.53–2.77(2H, m), 3.23(1H, t, J=9.6 Hz), 3.77(3H, s), 4.10–4.21(2H, m), 4.63, 5.08(1H×2, d×2, J=9.6 Hz), 5.91–5.96(2H, m), 6.42–6.52 (2H, m), 6.63–6.80(3H, m), 6.94(1H, d, J=8.8 Hz), 7.14(1H, dd, J=4.8 Hz, 7.7 Hz), 7.34(1H, d, J=7.7 Hz), 8.46(1H, d, J=4.8 Hz)

Rf Value: 0.44(E. Merck, Kieselgel 60F₂₅₄/chloroform:methanol:acetic acid=20:1:1)

EXAMPLE 62

High Resolution FAB-MS(m/e, $(C_{29}H_{27}NO_{10}+H)^+$): Calcd: 550.1713 Found: 550.1696

$^1$H-NMR(300 MHz, CDCl₃, δ ppm): 2.45–2.76(4H, m), 3.16(1H, t, J=9.4 Hz), 3.77(3H, s), 4.08–4.31(3H, m), 4.53–4.70(1H, m), 4.66, 5.16(1H×2, d×2, J=9.4 Hz), 5.92–5.96(2H, m), 6.43–6.51(2H, m), 6.65–6.81(3H, m), 6.84(1H, d, J=8.9 Hz), 7.18(1H, dd, J=5.0 Hz, 7.6 Hz), 7.38(1H, d, J=7.6 Hz), 8.44(1H, d, J=5.0 Hz)

Rf Value: 0.47(E. Merck, Kieselgel 60F₂₅₄/chloroform:methanol:acetic acid=20:1:1)

EXAMPLE 63

High Resolution FAB-MS(m/e, $(C_{32}H_{31}NO_{12}+H)^+$): Calcd: 622.1925 Found: 622.1938

$^1$H-NMR(300 MHz, CDCl₃, δ ppm): 2.50–2.90(6H, m), 3.03(1H, t, J=9.3 Hz), 3.78(3H, s), 4.09–4.54(6H, m), 4.63, 5.16(1H×2, d×2, J=9.3 Hz), 5.92–5.96(2H, m), 6.44–6.53 (2H, m), 6.64(1H, s), 6.66–6.80(2H, m), 6.91(1H, d, J=9.2 Hz), 7.15(1H, dd, J=4.9 Hz, 7.6 Hz), 7.33(1H, d, J=7.6 Hz), 8.53(1H, d, J=4.9 Hz)

Rf Value: 0.54(E. Merck, Kieselgel 60F₂₅₄/chloroform:methanol:acetic acid=20:1:1)

EXAMPLE 64

(5RS,6SR,7SR)-6-Carboxy-7-[2-(2-benzyloxy-1-methoxycarbonylethoxy)-4-methoxyphenyl]-5-(3,4-methylenedioxyphenyl)cyclopenteno[1,2-b]pyridine (one of diastereomers)

(1) (5RS,6SR,7SR)-7-[2-(2-Benzyloxy-1-methoxycarbonylethoxy)-4-methoxyphenyl]-6-tert-butoxycarbonyl- 5-(3,4-methylenedioxyphenyl) cyclopenteno[1,2-b]pyridine (5RS,6SR,7SR)-7-(2-Hydroxy-4-methoxyphenyl)-6-tert-butoxycarbonyl-5-(3,4-methylenedioxyphenyl) cyclopenteno[1,2-b]pyridine which was prepared in Example 50-(5) was allowed to react with 2-bromo-3-(benzyloxy)propionic acid methyl ester which was prepared from O-benzylserine according to the method described in a literature(J. Med. Chem., 1985,28,1447–1453)in the same manner as in Example 55-(1) and the crude product was purified by silica gel column chromatography(E. Merck Kieselgel 60/hexane:AcOEt=3:1 to 2:1 to 1:1) to give each of the diastereomers of (5RS,6SR,7SR)-7-[2-(2-benzyloxy-1-methoxycarbonylethoxy)-4-methoxyphenyl]-6-tert-butoxycarbonyl-5-(3,4-methylenedioxyphenyl) cyclopenteno[1,2-b]pyridine and (5RS,6SR,7SR)-7-[2-(1-methoxycarbonylethenyloxy)-4-methoxyphenyl]-6-tert-butoxycarbonyl-5-(3,4-methylenedioxyphenyl) cyclopenteno[1,2-b]pyridine.

(2) The title compound was prepared in the same manner as in Example 55-(2) using one of the diastereomers of (5RS,6SR,7SR)-7-[2-(2-benzyloxy-1-methoxycarbonylethoxy)-4-methoxyphenyl]-6-tert-butoxycarbonyl-5-(3,4-methylenedioxyphenyl) cyclopenteno[1,2-b]pyridine.

mp: 73°–76° C.

$^1$H-NMR(300 MHz, CDCl₃, δ ppm): 3.37(1H, t, J=10.0 Hz), 3.69(3H, s), 3.75(3H, s), 3.87(2H, d, J=5.0 Hz), 4.51 (1H, d, J=12.1 Hz), 4.56(1H, d, J=12.1 Hz), 4.65(1H, d, J=10.0 Hz), 4.88(1H, t, J=5.0 Hz), 5.04(1H, d, J=10.0 Hz), 5.92(1H, d, J=1.3 Hz), 5.94(1H, d, J=1.3 Hz), 6.36(1H, 1H, d, J=2.3 Hz), 6.53(1H, dd, J=2.3 Hz, 8.4 Hz), 6.72–6.80(3H, m), 7.07(1H, d, J=8.4 Hz), 7.10(1H, dd, J=4.5 Hz, 7.7 Hz), 7.18–7.40(6H, m), 8.46(1H, d, J=4.5 Hz)

Rf Value: 0.35(E. Merck, Kieselgel 60F₂₅₄/chloroform:methanol=10:1)

EXAMPLE 65

(5RS,6SR,7SR)-6-Carboxy-7-[2-(2-benzyloxy-1-methoxycarbonylethoxy)-4-methoxyphenyl]-5-(3,4-methylenedioxyphenyl)cyclopenteno[1,2-b]pyridine(the other diastereomer)

The title compound was prepared in the same manner as in Example 64-(2) using the other diastereomer of (5RS,6SR,7SR)-7-[2-(2-benzyloxy-1-methoxycarbonylethoxy)-4-methoxyphenyl]-6-tert-butoxycarbonyl-5-(3,4-methylenedioxyphenyl)cyclopenteno[1,2-b]pyridine which was prepared in Example 64-(1)(the other diastereomer).

mp: 75°–78° C.

$^1$H-NMR(300 MHz, CDCl₃, δ ppm): 3.37(1H, dd, J=3.6 Hz, 9.9 Hz), 3.55(1H, dd, J=5.4 Hz, 9.9 Hz), 3.70(1H, t, J=10.4 Hz), 3.70(3H, s), 3.75(3H, s), 4.35(1H, d, J=12.2 Hz), 4.42(1H, d, J=12.2 Hz), 4.59(1H, d, J=10.4 Hz), 4.77(1H, dd, J=3.6 Hz, 5.4 Hz), 4.85(1H, d, J=10.4 Hz), 5.92(2H, s), 6.32(1H, d, J=2.3 Hz), 6.52(1H, dd, J=2.3 Hz, 8.5 Hz), 6.72(1H, d, J=7.9 Hz), 6.83(1H, d, J=7.9 Hz), 6.88(1H, s), 7.03(1H, dd, J=4.8 Hz, 7.5 Hz), 7.17–7.38(7H, m), 8.36(1H, d, J=4.8 Hz)

Rf Value: 0.39(E. Merck, Kieselgel 60F₂₅₄/chloroform:methanol=10:1)

EXAMPLE 66

(5RS,6SR,7SR)-6-Carboxy-7-[2-(1-methoxycarbonylethenyloxy)-4-methoxyphenyl]-5-(3,4-methylenedioxyphenyl)cyclopenteno[1,2-b] pyridine The title compound was prepared in the same manner as in Example 64-(2) using (5RS,6SR,7SR)-7-[2-(1-methoxycarbonylethenyloxy)-4-methoxyphenyl]-6-tert-butoxycarbonyl-5-(3,4-methylenedioxyphenyl) cyclopenteno[1,2-b]pyridine which was prepared in Example 64-(1).

mp: 147°–150° C.

$^1$H-NMR(300 MHz, CDCl, δ ppm): 3.60(1H, t, J=10.0 Hz), 3.67(3H, s), 3.72(3H, s), 4.57(1H, d, J=10.0 Hz), 4.80(1H, d, J=10.0 Hz), 5.01(1H, d, J=2.1 Hz), 5.66(1H, d, J=2.1 Hz), 5.94(1H, d, J=1.4 Hz), 5.95(1H, d, J=1.4 Hz), 6.47(1H, d, J=2.5 Hz), 6.65(1H, dd, J=2.5 Hz, 8.5 Hz), 6.71–6.79(3H, m), 7.09(1H, dd, J=4.9 Hz, 7.6 Hz), 7.21(1H, d, J=8.5 Hz), 7.25(1H, d, J=7.6 Hz), 8.40(1H, d, J=4.9 Hz)

Rf Value: 0.22(E. Merck, Kieselgel 60F/chloroform:methanol=95:5)

Each Compound in the following Examples 67 and 68 was prepared by hydrogenation of the corresponding benzyl ether compound using palladium black as a catalyst.

EXAMPLE 67

(5RS,6SR,7SR)-6-Carboxy-7-[2-(2-hydroxy-1-methoxycarbonylethoxy)-4-methoxyphenyl]-5-(3,4-methylenedioxyphenyl)cyclopenteno[1,2-b]pyridine (one of diastereomers)

mp: 108°–110° C.

High Resolution FAB-MS(m/e, $(C_{27}H_{25}NO_9+H)^+$): Calcd: 508.1607 Found: 508.1602

$^1$H-NMR(300 MHz, CDCl$_3$, δ ppm): 3.31(1H, t, J=9.6 Hz), 3.75(3H, s), 3.76(3H, s), 3.99(1H, dd, J=4.2 Hz, 12.3 Hz), 4.10(1H, dd, J=2.2 Hz, 12.3 Hz), 4.63(1H, d, J=9.6 Hz), 4.79(1H, dd, J=2.2 Hz, 4.2 Hz), 5.29(1H, d, J=9.6 Hz), 5.96(2H, s), 6.28(1H, d, J=2.3 Hz), 6.52(1H, dd, J=2.3 Hz, 8.5 Hz), 6.70(1H, s), 6.74(1H, d, J=7.9 Hz), 6.78(1H, d, J=7.9 Hz), 7.07(1H, d, J=8.5 Hz), 7.14(1H, dd, J=4.9 Hz, 7.6 Hz), 7.35(1H, d, J=7.6 Hz), 8.43(1H, d, J=4.9 Hz)

Rf Value: 0.47(E. Merck, Kieselgel 60F$_{254}$/chloroform:methanol=10:1)

EXAMPLE 68

(5RS,6SR,7SR)-6-Carboxy-7-[2-(2-hydroxy-1-methoxycarbonylethoxy)- 4-methoxyphenyl]-5-(3,4-methylenedioxyphenyl)cyclopenteno[1,2-b]pyridine (the other diastereomer)

High Resolution FAB-MS(m/e, $(C_{27}H_{25}NO_9+H)^+$): Calcd: 508.1608 Found: 508.1579

$^1$H-NMR(300 MHz, CDCl$_3$, δ ppm): 3.48(1H, t, J=9.9 Hz), 3.66–3.80(2H, m), 3.69(3H, s), 3.75(3H, s), 4.55(1H, d, J=9.9 Hz), 4.77(1H, dd, J=3.0 Hz, 6.3 Hz), 5.07(1H, d, J=9.9 Hz), 5.94(2H, s), 6.31(1H, d, J=2.0 Hz), 6.52(1H, dd, J=2.0 Hz, 8.5 Hz), 6.73–6.76(3H, m), 7.10(1H, d, J=8.5 Hz), 7.13(1H, dd, J=5.0 Hz, 7.7 Hz), 7.29(1H, d, J=7.7 Hz), 8.45(1H, d, J=5.0 Hz)

Rf Value: 0.41(E. Merck, Kieselgel 60F$_{254}$/chloroform:methanol=10:1)

Each compound in the following Examples 69–71 was prepared by hydrolyzing the corresponding methyl ester compounds with base.

EXAMPLE 69

(5RS,6SR,7SR)-6-Carboxy-7-[2-(1-carboxy-2-hydroxyethoxy)-4-methoxyphenyl]-5-(3,4-methylenedioxyphenyl)cyclopenteno[1,2-b]pyridine (one of diastereomers)

mp: 158°–163° C.

High Resolution FAB-MS(m/e, $(C_{26}H_{23}NO_9+H)^+$): Calcd: 494.1451 Found: 494.1452

$^1$H-NMR(300 MHz, acetone-d$_6$, δ ppm): 3.79(3H, s), 3.898(1H, dd, J=10.2 Hz, 11.3 Hz), 3.900(1H, dd, J=4.6 Hz, 12.0 Hz), 3.99(1H, dd, J=3.0 Hz, 12.0 Hz), 4.68(1H, d, J=10.2 Hz), 5.03(1H, dd, J=3.0 Hz, 4.6 Hz), 5.28(1H, d, J=11.3 Hz), 6.03(2H, s), 6.58 (1H, dd, J=2.3 Hz, 8.4 Hz), 6.62(1H, d, J=2.3 Hz), 6.86–6.92(3H, m), 7.31(1H, dd, J=5.0 Hz, 7.6 Hz), 7.39–7.42(2H, m), 8.24(1H, d, J=5.0 Hz)

Rf Value: 0.25(E. Merck, Kieselgel 60F$_{254}$/chloroform:methanol:acetic acid=10:1:1)

EXAMPLE 70

(5RS,6SR,7SR)-6-Carboxy-7-[2-(1-carboxy-2-hydroxyethoxy)-4-methoxyphenyl]-5-(3,4-methylenedioxyphenyl)cyclopenteno[1,2-b]pyridine (the other diastereomer)

mp: 139°–142° C.

High Resolution FAB-MS(m/e, $(C_{26}H_{23}NO_9+H)^+$): Calcd: 494.1451 Found: 494.1454

$^1$H-NMR(300 MHz, acetone-d$_6$, δ ppm): 3.58(1H, t, J=9.7 Hz), 3.75–3.81(1H, dd, J=5.6 Hz, 11.9 Hz), 3.78(3H, s), 3.97(1H, dd, J=3.0 Hz, 11.9 Hz), 4.67(1H, d, J=9.7 Hz), 5.03(1H, dd, J=3.0 Hz, 5.6 Hz), 5.17(1H, d, J=9.7 Hz), 6.01(2H, s), 6.55(1H, dd, J=2.4 Hz, 8.4 Hz), 6.61(1H, d, J=2.4 Hz), 6.82–6.89(3H, m), 7.18(1H, d, J=8.4 Hz), 7.25 (1H, dd, J=5.0 Hz, 7.6 Hz), 7.39(1H, d, J=7.6 Hz), 8.32(1H, d, J=5.0 Hz)

Rf Value: 0.20(E. Merck, Kieselgel 60F$_{254}$/chloroform:methanol:acetic acid=10:1:1)

EXAMPLE 71

(5RS,6SR,7SR)-6-Carboxy-7-[2-(1-carboxyethenyloxy)-4-methoxyphenyl]-5-(3,4-methylenedioxyphenyl)cyclopenteno[1,2-b]pyridine mp: 144°–147° C.

High Resolution FAB-MS(m/e, $(C_{26}H_{21}NO_8+H)^+$): Calcd: 476.1345 Found: 476.1360

$^1$H-NMR(300 MHz, CDCl$_3$, δ ppm): 3.72(1H, t, J=10.4 Hz), 3.75(3H, s), 4.68(1H, d, J=10.4 Hz), 5.23(1H, d, J=10.4 Hz), 5.41(1H, s), 5.99(2H, s), 6.09(1H, s), 6.58(1H, d, J=2.4 Hz), 6.61(1H, dd, J=2.4 Hz, 8.1 Hz), 6.70(1H, d, J=1.6 Hz), 6.76(1H, dd, J=1.6 Hz, 7.9 Hz), 6.82(1H, d, J=7.9 Hz), 7.216(1H, d, J=8.1 Hz), 7.225(1H, dd, J=5.1 Hz, 7.7 Hz), 7.41(1H, d, J=7.7 Hz), 8.31(1H, d, J=5.1 Hz)

Rf Value: 0.46(E. Merck, Kieselgel 60F$_{254}$/chloroform:methanol:acetic acid=10:1:1)

EXAMPLE 72

(5RS,6SR,7SR)-6-Carboxy-2-hydroxymethyl-5-(3,4-methylenedioxyphenyl)-7-(4-methoxyphenyl)cyclopenteno[1,2-b]pyridine (1) 6-Methyl-3-(3,4-methylenedioxyphenylcarbonyl)pyridine-2-carboxylic acid methyl ester 6-Methyl-3-(3,4-methylenedioxyphenylcarbonyl)pyridine- 2-carboxylic acid which was prepared in the same manner as in Example 1-(1) was treated with HCl-methanol by a conventional method to give the methyl ester.

(2) 6-Methyl-3-(3,4-methylenedioxyphenylcarbonyl)-2-methoxycarbonylpyridine N-oxide To a dichloromethane(20 ml) solution of 6-methyl-3-(3, 4-methylenedioxyphenylcarbonyl)pyridine-2-carboxylic acid methyl ester(1.75 g,5.85 mmol) was added mCPBA (1.73 g) under ice-cooling. The mixture was stirred at room temperature for 20 h and an aqueous solution of sodium thiosulfate was added to the mixture to quench the reaction. The mixture was neutralized with a saturated aqueous solution of NaHCO$_3$ and extracted with dichloromethane. The organic layer was washed with brine, dried over MgSO$_4$ and concentrated under reduce pressure to give 6-methyl-3-(3, 4-methylenedioxyphenylcarbonyl)-2-methoxycarbonylpyridine N-oxide(1.57 g).

(3) 6-Hydroxymethyl-3-(3,4-methylenedioxyphenylcarbonyl)pyridine-2-carboxylic acid methyl ester To a DMF(15 ml) solution of 6-methyl-3-(3,4-methylenedioxyphenylcarbonyl)-2-methoxycarbonylpyridine N-oxide(1.56 g,4.95 mmol) was added anhydrous trifluoro acetic acid(7 ml) under ice-cooling, and the mixture was stirred at room temperature for 18 h. After removal of the excess anhydrous trifluoro acetic acid the residue was partitioned between water and AcOEt. The organic layer was washed with a saturated aqueous solution of NaHCO$_3$ and brine, dried over MgSO$_4$ and concentrated under reduced pressure to give 6-hydroxymethyl-3-(3,4-methylenedioxyphenylcarbonyl)pyridine-2-carboxylic acid methyl ester(1.72 g).

(4) 6-(Trimethylsilylethoxymethoxymethyl)-3-(3,4-methylenedioxyphenylcarbonyl)pyridine-2-carboxylic acid methyl ester To a dichloromethane(9 ml) solution of 6-hydroxymethyl-3-(3,4-methylenedioxyphenylcarbonyl)pyridine-2-carboxylic acid methyl ester(1.71 g,4.50 mmol) were added ethyldiisopropylamine(3.9 ml) and 2-trimethylsilylethoxymethyl chloride(2.4 ml) at room temperature. The mixture was stirred at room temperature for 17 h, partitioned between AcOEt and water. The organic layer was washed with a saturated aqueous solution of NaHCO$_3$ and brine, dried over Na$_2$SO$_4$ and concentrated under reduced pressure. The residue was purified by MPLC (E. Merck lobar column Kieselgel 60/hexane:AcOEt=3:1 to 1:1) to give 6-(2-trimethylsilylethoxymethoxymethyl)-3-(3,4-methylenedioxyphenylcarbonyl)pyridine-carboxylic acid methyl ester(1.44 g).

(5) 6-(2-Trimethylsilylethoxymethoxymethyl)-3-(3,4-methylenedioxyphenylcarbonyl)pyridine-2-carboxylic acid 6-(2-Trimethylsilylethoxymethoxymethyl)-3-(3,4-methylenedioxyphenylcarbonyl)pyridine-carboxylic acid methyl ester was subjected to alkaline hydrolysis in methanol to give 6-(2-trimethylsilylethoxymethoxymethyl)-3-(3,4-methylenedioxyphenylcarbonyl)pyridine-2-carboxylic acid.

(6) 6-Ethoxycarbonyl-7-oxo-2-(2-trimethylsilylethoxymethoxymethyl)-5-(3,4-methylenedioxyphenyl)cyclopent-1,3-dieno[1,2-b]pyridine To a THF(10 ml) solution of 6-(2-trimethylsilylethoxymethoxymethyl)-3-(3,4-methylenedioxyphenylcarbonyl)pyridine-2-carboxylic acid (1.27 g,2.94 mmol) was added CDI(950 ml) under ice-cooling. The mixture was stirred at room temperature for 5 h and treated with magnesium ethyl malonate(2.6 g) under ice-cooling. The mixture was stirred at room temperature for 63 h, treated with 3N HCl(10 ml) under ice-cooling, and then stirred at room temperature for 30 min. The mixture was extracted with dichloromethane and the organic layer was washed with brine, dried over Na$_2$SO$_4$ and concentrated under reduced pressure. The residue was dissolved in dichloromethane (20 ml), treated with Wako gel C-200(10 g) and stirred at room temperature for 4 h. The gel was removed by filtration and washed with AcOEt. The filtrate and washings were combined and concentrated under reduced pressure. The residue was purified by silica gel column chromatography(E. Merck Kieselgel 60/hexane:AcOEt= 3:1) to give 6-ethoxycarbonyl-7-oxo-2-(2-trimethylsilylethoxymethoxymethyl)- 5-(3,4-methylenedioxyphenyl)cyclopent-1,3-dieno[1,2-b]pyridine (556 mg) as a reddish orange solid.

(7) (5RS,6RS,7SR)-6-Ethoxycarbonyl-2-(2-trimethylsilylethoxymethoxymethyl)-5-(3,4-methylendioxyphenyl)-7-(4-methoxyphenyl)cyclopenteno[1,2-b]pyridine (5RS,6RS,7SR)-6-Ethoxycarbonyl-2-(2-trimethylsilylethoxymethoxymethyl)-5-(3,4-methylenedioxyphenyl)-7-(4-methoxyphenyl)cyclopent-1,3-dieno[1,2-b]pyridine was prepared in the same manner as in Example 50-(2),(3) using 6-ethoxycarbonyl-7-oxo-2-(2-trimethylsilylethoxymethoxymethyl)-5-(3,4-methylenedioxyphenyl)cyclopenteno[1,2-b]pyridine.

(8) (5RS,6RS,7SR)-6-Ethoxycarbonyl-2-hydroxymethyl-5-(3,4-methylenedioxyphenyl)-7-(4-methoxyphenyl)cyclopenteno[1,2-b]pyridine A solution of (5RS,6RS,7SR)-6-ethoxycarbonyl-2-(2-trimethylsilylethoxymethoxymethyl)-5-(3,4-methylenedioxyphenyl)-7-(4-methoxyphenyl)cyclopenteno[1,2-b]pyridine (34 mg,0.059 mmol) in 10% HCl-MeOH was stirred at room temperature for 15 h. After removal of the solvent the residue was partitioned between brine and AcOEt. The organic layer was washed a saturated aqueous solution of NaHCO$_3$ and brine, dried over Na$_2$SO$_4$ and concentrated under reduced pressure. The residue was purified by preparative TLC(E. Merck Kieselgel 60F$_{254}$/hexane:AcOEt=1:1) to give (5RS,6RS,7SR)-6-ethoxycarbonyl- 2-hydroxymethyl-5-(3,4-methylenedioxyphenyl)-7-(4-methoxyphenyl)cyclopenteno [1,2-b]pyridine(17 mg).

(9) The title compound was prepared in the same manner as in Example 2 using (5RS,6RS,7SR)-6-ethoxycarbonyl-2-hydroxymethyl-5-(3,4-methylenedioxyphenyl)-7-(4-methoxyphenyl)cyclopenteno[1,2-b]pyridine.

High Resolution FAB-MS(m/e, (C$_{24}$H$_{21}$NO$_6$+H)$^+$): Calcd: 420.1447 Found: 420.1457

$^1$H-NMR(300 MHz, CDCl$_3$, δ ppm): 3.30(1H, t, J=9.5 Hz), 3.81(3H, s), 4.60(1H, d, J=9.5 Hz), 4.70(2H, s), 4.71 (1H, d, J=9.5 Hz), 5.97(2H, s), 6.70(1H, brs), 6.75(1H, d, J=7.9 Hz), 6.80(1H, d, J=7.9 Hz), 6.89(2H, d, J=8.7 Hz), 7.09(1H, d, J=7.8 Hz), 7.17(2H, d, J=8.7 Hz), 7.31(1H, d, J=7.8 Hz)

Rf Value: 0.28(E. Merck, Kieselgel 60F$_{254}$/chloroform:methanol=10:1)

EXAMPLE 73

(5RS,6SR,7SR)-2-Ethoxymethyl-6-carboxy-7-(2-carboxymethoxy-4-methoxyphenyl)-5-(3,4-methylenedioxyphenyl)cyclopenteno[1,2-b]pyridine (1) (5RS,6RS,7SR)-2-Ethoxycarbonyl-2-hydroxymethyl-7-(2-hydroxy-4-methoxyphenyl)-5-(3,4-methylenedioxyphenyl)cyclopenteno[1,2-b]pyridine (5RS,6RS,7SR)-2-Ethoxycarbonyl-2-hydroxymethyl-7-(2-hydroxy-4-methoxyphenyl)-5-(3,4-methylenedioxyphenyl)cyclopenteno[1,2-b]pyridine was prepared in the same manner as in Example 72-(7),(8) using 6-ethoxycarbonyl-7-oxo-2-(2-trimethylsilylethoxymethoxymethyl)-5-(3,4-methylenedioxyphenyl)cyclopent-1,3-dieno[1,2-b]pyridine prepared in Example 72-(6) and 4-methoxy-2-methoxymethoxyphenyl bromide.

(2) (5RS,6RS,7SR)-2-Ethoxycarbonyl-7-(2-ethoxycarbonylmethoxy-4-methoxyphenyl)-2-hydroxymethyl-5-(3,4-methylenedioxyphenyl)cyclopenteno[1,2-b]pyridine (5RS,6RS,7SR)-2-Ethoxycarbonyl-7-(2-ethoxycarbonylmethoxy-4-methoxyphenyl)-2- hydroxymethyl-5-(3,4-methylenedioxyphenyl)cyclopenteno[1,2-b]pyridine was prepared in the same manner as in Example 30-(3) using (5RS,6RS,7SR)-2-ethoxycarbonyl-2-hydroxymethyl-7-(2-hydroxy-4-methoxyphenyl)-5-(3,4-methylenedioxyphenyl)cyclopenteno[1,2-b]pyridine which was prepared in (1).

(3) (5RS,6RS,7SR)-2-Ethoxycarbonyl-7-(2-ethoxycarbonylmethoxy-4-methoxyphenyl)-2-chloromethyl-5-(3,4-methylenedioxyphenyl)cyclopenteno[1,2-b]pyridine To a chloroform solution(1 ml) of (5RS,6RS,7SR)-2-ethoxycarbonyl-7-(2-ethoxycarbonylmethoxy-4-methoxyphenyl)-2-hydroxymethyl-5-(3,4-methylenedioxyphenyl)cyclopenteno[1,2-b]pyridine(17 mg,0.031 mmol) was added thionyl chloride(20 µl) under ice-cooling and the mixture was stirred at room temperature for 2 h. After removal of the solvent the residue was dried under reduced pressure to give (5RS,6RS,7SR)-2-ethoxycarbonyl- 7-(2-ethoxycarbonylmethoxy-4-methoxyphenyl)-2-chloromethyl-5-(3,4-methylenedioxyphenyl)cyclopenteno[1,2-b]pyridine(14 mg).

(4) (5RS,6RS,7SR)-2-Ethoxycarbonyl-7-(2-ethoxycarbonylmethoxy-4-methoxyphenyl)-2-chloromethyl-5-(3,4-methylenedioxyphenyl)cyclopenteno[1,2-b]pyridine (14 mg,0.025 mmol) which was prepared in (3) was dissolved in an ethanol solution of sodium ethoxide (1.1M,10 ml), stirred at room temperature for 16 h, treated with water, and then stirred at room temperature 18 h. The reaction solution was treated with 1N HCl and extracted with AcOEt. The organic layer was washed with brine, dried over $Na_2SO_4$ and concentrated under reduced pressure to give the title compound(8.4 mg).

High Resolution FAB-MS(m/e, $(C_{28}H_{27}NO_9+H)^+$): Calcd: 522.1764 Found: 522.1785

$^1$H-NMR(300 MHz, acetone-$d_6$, δ ppm): 1.18(3H, t, J=7.1 Hz), 3.54(2H, q, J=7.1 Hz), 3.68(1H, t, J=10.0 Hz), 3.79(3H, s), 4.45–4.55(3H, m), 4.63(1H, d, J=10.0 Hz), 4.74(1H, d, J=16.2 Hz), 4.95(1H, d, J=10.0 Hz), 6.00(2H, s), 6.57(1H, dd, J=2.4 Hz, 8.3 Hz), 6.61(1H, d, J=2.4 Hz), 6.82–6.93(3H, m), 7.22(1H, d, J=8.3 Hz), 7.34–7.40(2H, m)

Rf Value: 0.60(E. Merck, Kieselgel 60$F_{254}$/chloroform:methanol:acetic acid=10:1:1)

EXAMPLE 74

(5RS,6SR,7SR)-7-(2-Ethylaminocarbonylmethoxy-4-methoxyphenyl)-2-ethylaminomethyl-6-carboxy-5-(3,4-methylenedioxyphenyl)cyclopenteno[1,2-b]pyridine (1) (5RS,6RS,7SR)-2-Ethoxycarbonyl-7-(2-ethoxycarbonylmethoxy-4-methoxyphenyl)-2-chloromethyl-5-(3,4-methylenedioxyphenyl)cyclopenteno[1,2-b]pyridine which was prepared in Example 73-(3) was dissolved in a THF solution of ethylamine(21%,4 ml) and stirred at room temperature for 6 h. After removal of the solvent the residue was purified by preparative TLC(E. Merck Kieselgel 60$F_{254}$/chloroform:methanol=10:1) to give (5RS,6RS,7SR)-7-(2-ethylaminocarbonylmethoxy-4-methoxyphenyl)-2-ethylaminomethyl-6-ethoxycarbonyl-5-(3,4-methylenedioxyphenyl)cyclopenteno[1,2-b]pyridine (17.1 mg) and (5RS,6RS,7SR)-2-ethylaminomethyl-6-ethoxycarbonyl-7-(2-ethoxycarbonylmethoxy-4-methoxyphenyl)-5-(3,4-methylenedioxyphenyl)cyclopenteno[1,2-b]pyridine(1.2 mg).

(2) The title compound was prepared in the same manner as in Example 2 using (5RS,6RS,7SR)-7-(2-ethylaminocarbonylmethoxyoxy-4-methoxyphenyl)-2-ethylaminomethyl-6-ethoxycarbonyl-5-(3,4-methylenedioxyphenyl)cyclopenteno[1,2-b]pyridine which was prepared in (1).

High Resolution FAB-MS(m/e, $(C_{30}H_{33}N_3O_7+H)^+$): Calcd: 548.2397 Found: 548.2396

$^1$H-NMR(300 MHz, $CD_3OD$, δ ppm): 1.13(3H, t, J=7.3 Hz), 1.23(3H, t, J=7.2 Hz), 3.04(2H, q, J=7.2 Hz), 3.17(1H, t, J=9.9 Hz), 3.23–3.33(2H, m), 3.76(3H, s), 4.23(2H, s), 4.36(1H, d, J=14.6 Hz), 4.44(1H, d, J=14.6 Hz), 4.60(1H, d, J=9.9 Hz), 5.04(1H, d, J=9.9 Hz), 5.90(2H, s), 6.48(1H, d, J=2.3 Hz), 6.55(1H, dd, J=2.3 Hz, 8.1 Hz), 6.70(1H, s), 6.74–6.80(2H, m), 6.99(1H, d, J=8.1 Hz), 7.24(1H, d, J=7.9 Hz), 7.35–7.40(1H, m)

Rf Value: 0.43(E. Merck, Kieselgel 60$F_{254}$/chloroform:methanol:acetic acid=10:1:1)

EXAMPLE 75

(5RS,6SR,7SR)-2-Ethylaminomethyl-6-carboxy-7-(2-carboxymethoxy-4-methoxyphenyl)-5-(3,4-methylenedioxyphenyl)cyclopenteno[1,2-b]pyridine The title compound was prepared in the same manner as in Example 2 using (5RS,6RS,7SR)-2-ethylaminomethyl-6-ethoxycarbonyl-7-(2-ethoxycarbonylmethoxy-4-methoxyphenyl)-5-(3,4-methylenedioxyphenyl)cyclopenteno[1,2-b]pyridine which was prepared in Example 74-(1).

High Resolution FAB-MS(m/e, $(C_{28}H_{28}N_2O_8+H)^+$): Calcd: 521.1924 Found: 521.1939

$^1$H-NMR(300 MHz, $CD_3OD$, δ ppm): 1.25(3H, t, J=7.2 Hz), 3.06(2H, q, J=7.2 Hz), 3.56(1H, t, J=10.0 Hz), 3.75(3H, s), 4.17(1H, d, J=15.4 Hz), 4.19(2H, s), 4.28(1H, d, J=15.4 Hz), 4.56(1H, d, J=10.0 Hz), 4.71(1H, d, J=10.0 Hz), 5.92(2H, s), 6.42(1H, d, J=2.2 Hz), 6.49(1H, dd, J=2.2 Hz, 8.2 Hz), 6.71(1H, s), 6.75–6.81(2H, m), 7.13(1H, d, J=8.2 Hz), 7.17(1H, d, J=7.6 Hz), 7.27–7.31(1H, m)

Rf Value: 0.22(E. Merck, Kieselgel 60$F_{254}$/chloroform:methanol:acetic acid=10:1:1)

EXAMPLE 76

(5RS,6SR,7SR)-6-Carboxy-7-(2-carboxylmethoxy-4-methoxyphenyl)-2-propoxy-5-(3,4-methylenedioxyphenyl)cyclopenteno[1,2-b]pyridine The title compound was prepared in the same manner as in Example 30-(1), Example 50-(1)–(6) and Example 30-(4) using 6-propoxypyridine-2,3-dicarboxylic acid anhydride.

High Resolution FAB-MS(m/e, $(C_{28}H_{27}NO_9+H)^+$): Calcd: 522.1764 Found: 522.1769

$^1$H-NMR(300 MHz, $CDCl_3$, δ ppm): 0.97(3H, t, J=7.2 Hz), 1.72(2H, sext, J=7.2 Hz), 2.96(1H, t, J=9.6 Hz), 3.81 (3H, s), 4.02–4.22(2H, m), 4.52(1H, d, J=16.1 Hz), 4.61(1H, d, J=9.6 Hz), 4.67(1H, d, J=16.1 Hz), 5.22(1H, d, J=9.6 Hz), 5.92, 5.94(1H×2, d×2, J=1.9 Hz), 6.37(1H, d, J=2.3 Hz), 6.53(1H, dd, J=2.3 Hz, 8.6 Hz), 6.59(1H, d, J=8.4 Hz), 6.63–6.79(3H, m), 7.06(1H, d, J=8.4 Hz), 7.20(1H, d, J=8.6 Hz)

Rf Value: 0.31(E. Merck, Kieselgel 60$F_{254}$/chloroform:methanol:acetic acid=20:1:1)

EXAMPLE 77

(5RS,6SR,7SR)-2-Ethyl-6-carboxy-5-(3,4-methylenedioxyphenyl)-7-(4-methoxyphenyl)cyclopenteno[1,2-b]pyridine (1) 6-Phenylthiopyridine-2,3-dicarboxylic acid dimethyl ester To an anhydrous DMF suspension of $K_2CO_3$(8.29 g) was added thiophenol(3.08 ml) under nitrogen atmosphere and the mixture was stirred at room temperature for 10 min. A DMF(10 ml) solution of 6-chloropyridine-2,3-dicarboxylic acid dimethyl ester was added to the mixture. The mixture was stirred at 80° C. for 30 min and at 100° C. for 1 h, then cooled. The reaction solution was partitioned between water and AcOEt, and the organic layer was washed with water and then dried over $MgSO_4$. After evaporation of the solvent the residue was purified by dry flash column chromatography(E. Merck Kieselgel 60/hexane:dichloromethane=1:1 to dichloromethane) to give 6-phenylthiopyridine-2,3-dicarboxylic acid dimethyl ester(6.07 g) as a colorless powder.

(2) 5-Hydroxy-2-phenylthio-6-tert-butoxycarbonyl-5-(3, 4-methylenedioxyphenyl)-7-(4-methoxyphenyl)cyclopent-1,3-dieno[2,1-b]pyridine 6-phenylthiopyridine-2,3-dicarboxylic acid dimethyl ester which was prepared in (1) was converted to the acid anhydride in a conventional manner and subjected to the same reactions as in Example 30-(1), Example 50-(1),(2) to give 5-hydroxy-2-phenylthio-6-tert-butoxycarbonyl-5-(3,4-methylenedioxyphenyl)-7-(4-methoxyphenyl)cyclopent-1,3-dieno[2,1-b]pyridine.

(3) 5-(2-Trimethylsilylethoxymethoxy)-2-phenylthio-6-tert-butoxycarbonyl-5-(3,4-methylenedioxyphenyl)-7-(4-methoxyphenyl)cyclopent-1,3-dieno[2,1-b]pyridine To a dichloromethane(1 ml) solution of 5-hydroxy-2-phenylthio-6-tert-butoxycarbonyl-5-(3,4-methylenedioxyphenyl)-7-(4-methoxyphenyl)cyclopent-1,3-dieno[2,1-b]pyridine(647 mg,1.14 mmol) which was prepared in (2) was added ethyldiisopropylamine(0.99 ml). The mixture was cooled in an ice-bath and trimethylsilylethoxymethyl chloride(0.61 ml) was added dropwise to the mixture. The mixture was stirred at room temperature for 2 h. diluted with dichloromethane, washed with a saturated aqueous solution of $NaHCO_3$ and dried over $MgSO_4$. After removal of the solvent under reduced pressure the resulting residue was purified by column chromatography(E. Merck Kieselgel 60/hexane:dichloromethane=1:3 to 1:10) to give 5-(2-trimethylsilylethoxymethoxy)-2-phenylthio-6-tert-butoxycarbonyl-5-(3,4-methylenedioxyphenyl)-7-(4-methoxyphenyl)cyclopent-1,3-dieno[2,1-b]pyridine(594 mg) as a pale yellow oil.

(4) 5-(2-Trimethylsilylethoxymethoxy)-2-phenylsulfonyl-6-tert-butoxycarbonyl-5-(3,4-methylenedioxyphenyl)-7-(4-methoxyphenyl)cyclopent-1,3-dieno[2,1-b]pyridine To a chloroform(40 ml) solution of 5-(2-trimethylsilylethoxymethoxy)-2-phenylthio-6-tert-butoxycarbonyl-5-(3,4-methylenedioxyphenyl)-7-(4-methoxyphenyl)cyclopent-1,3-dieno[2,1-b]pyridine (593 mg,0.850 mmol) which was prepared in (3) was added mCPBA(323 mg) and the solution was stirred at room temperature for 12 h. The reaction solution was partitioned between chloroform and 5% aqueous solution of $NaHCO_3$. The organic layer was washed with a saturated aqueous solution of $NaHCO_3$ and dried over $MgSO_4$. After removal of the solvent under reduced pressure the residue was purified by dry flash chromatography(E. Merck Kieselgel 60/dichloromethane) to give 5-(2-trimethylsilylethoxymethoxy)-2-phenylsulfonyl-6-tert-butoxycarbonyl-5-(3,4-methylenedioxyphenyl)-7-(4-methoxyphenyl)cyclopent-1,3-dieno[2,1-b]pyridine (554 mg) as a pale yellow powder.

(5) 2-Ethyl-5-(2-trimethylsilylethoxymethoxy)-6-tert-butoxycarbonyl-5-(3,4-methylenedioxyphenyl)-7-(4-methoxyphenyl)cyclopent-1,3-dieno[2,1-b]pyridine To a THF(2.5 ml) solution of 5-(2-trimethylsilylethoxymethoxy)-2-phenylsulfonyl-6-tert-butoxycarbonyl-5-(3,4-methylenedioxyphenyl)-7-(4-methoxyphenyl)cyclopent-1,3-dieno[2,1-b]pyridine (100 mg,0.137 mmol) which was prepared in (4) was added a THF solution(0.10M,1.64 ml) of ethyllithium dropwise at −78° C. and the solution was stirred at −78° C. for 1.5 h. To the reaction solution was added 10% citric acid at −78° C. and the solution was extracted with AcOEt. The organic layer was washed with brine and dried over $MgSO_4$. After removal of the solvent under reduced pressure the resulting residue was purified by preparative TLC(E. Merck Kieselgel 60/hexane:AcOEt=3:1) to give 2-ethyl-5-(2-trimethylsilylethoxymethoxy)-6-tert-butoxycarbonyl-5-(3, 4-methylenedioxyphenyl)-7-(4-methoxyphenyl)cyclopent-1,3-dieno[2,1-b]pyridine(25.6 mg).

(6) 2-Ethyl-5-hydroxy-6-tert-butoxycarbonyl-5-(3,4-methylenedioxyphenyl)-7-(4-methoxyphenyl)cyclopent-1, 3-dieno[2,1-b]pyridine To a methanol(2 ml) solution of 2-ethyl-5-(2-trimethylsilylethoxymethoxy)-6-tert-butoxycarbonyl-5-(3, 4-methylenedioxyphenyl)-7-(4-methoxyphenyl)cyclopent-1,3-dieno[2,1-b]pyridine (52 mg,0.084 mmol) which was prepared in (5) was added 10%HCl-methanol(0.2 ml) dropwise under ice-cooling and the mixture was stirred at room temperature for 2 h. To the reaction solution was added a saturated aqueous solution of $NaHCO_3$ and the solution was extracted with AcOEt. The organic layer was washed with brine and dried over $MgSO_4$. The solvent was evaporated to give 2-ethyl-5-hydroxy-6-tert-butoxycarbonyl-5-(3,4-methylenedioxyphenyl)-7-(4-methoxyphenyl)cyclopent-1, 3-dieno[2,1-b]pyridine (45 mg).

(7) The title compound was prepared in the same manner as in Example 50-(3),(4),(7) using 2-ethyl-5-hydroxy-6-tert-butoxycarbonyl-5-(3,4-methylenedioxyphenyl)-7-(4-methoxyphenyl)cyclopent-1,3-dieno[2,1-b]pyridine which was prepared in (6).

High Resolution FAB-MS(m/e, $(C_{25}H_{23}NO_5+H)^+$): Calcd: 418.1654 Found: 418.1636

$^1$H-NMR(300 MHz, $CDCl_3$, δ ppm): 1.21(3H, t, J=7.6 Hz), 2.65–2.86(2H, m), 3.15(1H, t, J=9.2 Hz), 3.73(3H, s), 4.52, 4.75(1H×2, d×2, J=9.2 Hz), 5.94(2H, s), 6.71(1H, s), 6.64–6.87(2H, m), 6.81(2H, d, J=8.4 Hz), 7.01(1H, d, J=7.9 Hz), 7.13(2H, d, J=8.4 Hz), 7.24(1H, d, J=7.9 Hz)

Rf Value: 0.26(E. Merck, Kieselgel $60F_{254}$/chloroform:methanol=20:1)

Each compound in the following Examples 78–81 was prepared in the same manner as in Example 77.

EXAMPLE 78

(5RS,6SR,7SR)-6-Carboxy-2-cyclopropyl-5-(3,4-methylenedioxyphenyl)-7-(4-methoxyphenyl) cyclopenteno[1,2-b]pyridine mp: 98°–100° C.

High Resolution FAB-MS(m/e, $(C_{26}H_{23}NO_5+H)^+$): Calcd: 430.1654 Found: 430.1640

$^1$H-NMR(300 MHz, $CDCl_3$, δ ppm): 0.75–0.95(4H, m), 1.95–2.05(1H, m), 3.19(1H, t, J=9.5 Hz), 3.80(3H, s), 4.53 (1H, d, J=9.5 Hz), 4.67(1H, d, J=9.5 Hz), 5.95(2H, ABq, J=1.5 Hz), 6.69(1H, d, J=1.6 Hz), 6.73(1H, dd, J=1.6 Hz, 7.8 Hz), 6.78(1H, d, J=7.8 Hz), 6.86(2H, d, J=9.1 Hz), 6.89(1H, d, J=8.0 Hz), 7.15(1H, d, J=8.0 Hz), 7.16(2H, d, J=9.1 Hz)

Rf Value: 0.51(E. Merck, Kieselgel $60F_{254}$/chloroform:methanol=10:1)

EXAMPLE 79

(5RS,6RS,7SR)-6-Carboxy-2-pentyl-5-(3,4-methylenedioxyphenyl)-7-(4-methoxyphenyl)cyclopenteno[1,2-b]pyridine High Resolution FAB-MS(m/e, $(C_{28}H_{29}NO_5+H)^+$): Calcd: 460.2124 Found: 460.2127

$^1$H-NMR(300 MHz, CDCl$_3$, δ ppm): 0.86(3H, t, J=6.8 Hz), 1.24–1.38(4H, m), 1.57–1.70(2H, m), 2.69–2.77(2H, m), 3.17(1H, t, J=9.4 Hz), 3.78(3H, s), 4.54(1H, d, J=9.4 Hz), 4.73(1H, d, J=9.4 Hz), 5.95(2H, ABq, J=1.4 Hz), 6.69(1H, d, J=1.5 Hz), 6.75(1H, dd, J=1.5 Hz, 7.8 Hz), 6.78(1H, d, J=7.8 Hz), 6.85(2H, d, J=8.7 Hz), 6.99(1H, d, J=7.7 Hz), 7.14(2H, d, J=8.7 Hz), 7.21(1H, d, J=7.7 Hz)

Rf Value: 0.47(E. Merck, Kieselgel 60F$_{254}$/chloroform:methanol=10:1)

EXAMPLE 80

6-Carboxy-5-hydroxy-2-(3-butenyl)-5-(3,4-methylenedioxyphenyl)-7-(4-methoxyphenyl)cyclopent-1,3-dieno[2,1-b]pyridine High Resolution FAB-MS(m/e, $(C_{27}H_{23}NO_6+H)^+$): Calcd: 458.1604 Found: 458.1618

$^1$H-NMR(300 MHz, CDCl$_3$, δ ppm): 2.47(2H, q, J=7.3 Hz), 2.86(2H, t, J=7.3 Hz), 3.88(3H, s), 4.90–5.10(2H, m), 5.75–6.00(3H, m), 6.71(1H, d, J=7.6 Hz), 6.89–7.10(5H, m), 7.45(1H, d, J=7.6 Hz), 7.76(2H, d, J=7.8 Hz)

Rf Value: 0.42(E. Merck, Kieselgel 60F$_{254}$/chloroform:methanol=10:1)

EXAMPLE 81

(5RS,6RS,7SR)-6-Carboxy-2-(3-butenyl)-5-(3,4-methylenedioxyphenyl)-7-(4-methoxyphenyl)cyclopenteno[1,2-b]pyridine High Resolution FAB-MS(m/e, $(C_{27}H_{25}NO_5+H)^+$): Calcd: 444.1811 Found: 444.1805

$^1$H-NMR(300 MHz, CDCl$_3$, δ ppm): 2.34–2.48(2H, m), 2.74–2.93(2H, m), 3.19(1H, t, J=9.6 Hz), 4.55, 4.73(1H×2, d×2, J=9.6 Hz), 3.79(3H, s), 4.90–5.06(2H, m), 5.71–5.90 (1H, m), 5.91–6.00(2H, m), 6.69(1H, s), 6.71–6.81(2H, m), 6.86(2H, d, J=8.6 Hz), 6.99(1H, d, J=8.0 Hz), 7.15(2H, d, J=8.6 Hz), 7.24(1H, d, J=8.0 Hz)

Rf Value: 0.25(E. Merck, Kieselgel 60F$_{254}$/chloroform:methanol=20:1)

EXAMPLE 82

(5RS,6SR,7SR)-6-Carboxy-2-propylthio-5-(3,4-methylenedioxyphenyl)-7-(4-methoxyphenyl)cyclopenteno[1,2-b]pyridine (1) 5-(2-Trimethylsilylethoxymethoxy)-2-propylthio-6-tert-butoxycarbonyl-5-(3,4-methylenedioxyphenyl)-7-(4-methoxyphenyl)cyclopent-1,3-dieno[2,1-b]pyridine A benzene(1 ml) solution of 5-(2-trimethylsilylethoxymethoxy)-2-phenylsulfonyl-6-tert-butoxycarbonyl-5-(3,4-methylenedioxyphenyl)-7-(4-methoxyphenyl)cyclopent-1,3-dieno[2,1-b]pyridine(100 mg, 0.14 mmol) which was prepared in Example 77-(4) and 18-Crown-6(7.1 mg) was added to a benzene solution(1 ml) of sodium propylmercaptide which was prepared from sodium hydride(7.3 mg) and propanethiol(19 µl) and the mixture was stirred at room temperature under nitrogen atmosphere for 19 h. To the solution was added a saturated aqueous solution of NaHCO$_3$ and the solution was extracted with AcOEt. The organic layer was washed with brine, dried over MgSO$_4$ and concentrated under reduced pressure. The residue was purified by silica gel column chromatography (E. Merck Kieselgel 60/hexane:AcOEt=9:1 to 3:1) to give 5-(2-trimethylsilylethoxymethoxy)-2-propylthio-6-tert-butoxycarbonyl-5-(3,4-methylenedioxyphenyl)-7-(4-methoxyphenyl)cyclopent-1,3-dieno[2,1-b]pyridine(19 mg) as a brown solid.

(2) The title compound was prepared in the same manner as in Example 77-(5),(6) using 5-(2-trimethylsilylethoxymethoxy)-2-propylthio-6-tert-butoxycarbonyl-5-(3,4-methylenedioxyphenyl)-7-(4-methoxyphenyl)cyclopent-1,3-dieno[2,1-b]pyridine which was prepared in (1).

mp: 62°–65° C.

High Resolution FAB-MS(m/e, $(C_{26}H_{25}NO_5S+H)^+$): Calcd: 464.1532 Found: 464.1541

$^1$H-NMR(300 MHz, CDCl$_3$, δ ppm): 0.84(3H, t, J=7.4 Hz), 1.55(2H, sext, J=7.4 Hz), 2.80(1H, dt, J=13.7 Hz, 7.4 Hz), 3.08(1H, dt, J=13.7 Hz, 7.4 Hz), 3.27(1H, t, J=8.8 Hz), 3.79(3H, s), 4.53(1H, d, J=8.8 Hz), 4.65(1H, d, J=8.8 Hz), 5.94(2H, brs), 6.68(1H, s), 6.73(1H, d, J=7.8 Hz), 6.77(1H, d, J=7.8 Hz), 6.86(2H, d, J=8.3 Hz), 6.99(1H, d, J=8.2 Hz), 7.07(1H, d, J=8.2 Hz), 7.18(2H, d, J=8.3 Hz)

Rf Value: 0.32(E. Merck, Kieselgel 60F$_{254}$/hexane:AcOEt=1:1)

Each compound in the following Example 83 and 84 was prepared in the same manner as in Example 77 using lithium amide instead of lithium alkyl.

EXAMPLE 83

(5RS,6SR,7SR)-6-Carboxy-2-propylamino-5-(3,4-methylenedioxyphenyl)-7-(4-methoxyphenyl)cyclopenteno[1,2-b]pyridine mp: 92°–100° C.

High Resolution FAB-MS(m/e, $(C_{26}H_{26}N_2O_5+H)^+$): Calcd: 447.1920 Found: 447.1902

$^1$H-NMR(300 MHz, CDCl$_3$, δ ppm): 0.94(3H, t, J=7.2 Hz), 1.61(2H, sext, J=7.2 Hz), 2.97(1H, t, J=8.3 Hz), 3.08 (2H, t, J=7.2 Hz), 3.64(3H, s), 4.33(1H, d, J=8.3 Hz), 4.63(1H, d, J=8.3 Hz), 5.93(2H, s), 6.33(1H, d, J=8.7 Hz), 6.63–6.76(3H, m), 6.79(2H, d, J=8.5 Hz), 7.15(2H, d, J=8.5 Hz), 7.21(1H, d, J=8.7 Hz)

Rf Value: 0.56(E. Merck, Kieselgel 60F$_{254}$/chloroform:methanol=10:1)

EXAMPLE 84

(5RS,6SR,7SR)-6-Carboxy-2-piperidino-5-(3,4-methylenedioxyphenyl)-7-(4-methoxyphenyl)cyclopenteno[1,2-b]pyridine mp: 48°–50° C.

High Resolution FAB-MS(m/e, $(C_{28}H_{28}N_2O_5+H)^+$): Calcd: 473.2077 Found: 473.2078

$^1$H-NMR(300 MHz, CDCl$_3$, δ ppm): 1.50–1.70(6H, m), 3.15(1H, dd, J=9.1 Hz, 9.5 Hz), 3.30–3.50(4H, m), 3.81(3H, s), 4.48(1H, d, J=9.1 Hz), 4.60(1H, d, J=9.5 Hz), 5.94(2H, ABq, J=1.4 Hz), 6.59(1H, d, J=8.6 Hz), 6.71(1H, s), 6.76 (2H, s), 7.07(1H, d, J=8.6 Hz), 7.21(2H, d, J=8.8 Hz), 6.87(2H, d, J=8.8 Hz)

Rf Value: 0.23(E. Merck, Kieselgel 60F$_{254}$/chloroform:methanol=20:1)

Each compound in the following Example 85 and 86 was prepared in the same manner as in Example 77-(4), (5), Example 50-(3) to (6) and Example 30-(4) using 6-ethoxycarbonyl-5-(trimethylsilylethoxymethoxy)-2-phenylsulfonyl-7-(2-benzyloxy-4-methoxyphenyl)-5-(3,4-methylenedioxyphenyl)cyclopent-1,3-dieno[2,1-b]pyridine instead of 5-(trimethylsilylethoxymethoxy)-2-phenylsulfonyl-6-tert-butoxycarbonyl-5-(3,4-methylenedioxyphenyl)-7-(4-methoxyphenyl)cyclopent-1, 3-dieno[2,1-b]pyridine.

EXAMPLE 85

(5RS,6SR,7SR)-6-Carboxy-7-(2-carboxymethoxy-4-methoxyphenyl)-2-butyl-5-(3,4-methylenedioxyphenyl)cyclopenteno[1,2-b]pyridine mp: 123°–128° C.

High Resolution FAB-MS(m/e, $(C_{29}H_{29}NO_8+H)^+$): Calcd: 520.1971 Found: 520.1968

$^1$H-NMR(300 MHz, $CD_3OD$, δ ppm): 0.91(3H, t, J=7.3 Hz), 1.28–1.40(2H, m), 1.55–1.65(2H, m), 2.78(2H, dd, J=7.7 Hz, 7.8 Hz), 3.53(1H, t, J=9.9 Hz), 3.77(3H, s), 4.33(1H, d, J=16.0 Hz), 4.53(1H, d, J=16.0 Hz), 4.55(1H, d, J=9.9 Hz), 4.91(1H, d, J=9.9 Hz), 5.92(2H, s), 6.50(1H, d, J=2.4 Hz), 6.56(1H, dd, J=2.4 Hz, 8.4 Hz), 6.76–6.83(3H, m), 7.13(1H, d, J=8.4 Hz), 7.21(1H, d, J=7.9 Hz), 7.40(1H, d, J=7.9 Hz)

Rf Value: 0.18(E. Merck, Kieselgel $60F_{254}$/chloroform:methanol:acetic acid=20:1:1)

EXAMPLE 86

(5RS,6SR,7SR)-6-Carboxy-7-(2-carboxymethoxy-4-methoxyphenyl)-2-propylamino-5-(3,4-methylenedioxyphenyl)cyclopenteno[1,2-b]pyridine mp: 166°–168.5° C.

High Resolution FAB-MS(m/e, $(C_{28}H_{28}N_2O_8+H)^+$): Calcd: 521.1924 Found: 521.1945

H-NMR(300 MHz, acetone-d, δ ppm): 0.91(3H, t, J=7.4 Hz), 1.58(2H, sept, J=7.4 Hz), 3.00–3.32(1H, br), 3.18(2H, brt.dt-like, J=7.4 Hz), 3.51(1H, t, J=9.0 Hz), 3.77(3H, s), 4.52(1H, d, J=9.0 Hz), 4.67(2H, ABq, J=16.1 Hz, Δv=54.0 Hz), 5.03(1H, d, J=9.0 Hz), 5.99(2H, s), 6.50(1H, d, J=8.4 Hz), 6.54(1H, dd, J=2.3 Hz, 8.5 Hz), 6.61(1H, d, J=2.3 Hz), 6.82(2H, S), 6.84(1H, s), 7.17(1H, d, J=8.4 Hz), 7.19(1H, d, J=8.5 Hz)

Rf Value: 0.68(E. Merck, Kieselgel 60F/chloroform:methanol:acetic acid=10:1:1)

EXAMPLE 87

(5RS,6SR,7SR)-6-Carboxy-7-(2-carboxymethylamino-4-methoxyphenyl)-5-(3,4-methylenedioxyphenyl)cyclopenteno[1,2-b]pyridine (1) 6-Ethoxycarbonyl-7-oxo-5-(3,4-methylenedioxyphenyl)cyclopent-1,3-dieno[1,2-b]pyridine 6-Ethoxycarbonyl-7-oxo-5-(3,4-methylenedioxyphenyl)cyclopent-1,3-dieno[1,2-b]pyridine was prepared in the same manner as in Example 72-(6) using 3-(3,4-methylenedioxyphenylcarbonyl)pyridine-2-carboxylic acid.

(2) 6-Ethoxycarbonyl-7-(2-nitro-4-methoxyphenyl)-7-hydroxy-5-(3,4-methylenedioxyphenyl)cyclopent-1,3-dieno[1,2-b]pyridine To a solution of 4-methoxy-3-nitrophenyl bromide(472 mg) in THF(24 ml) was added a solution of phenyl lithium in cyclohexane-ether(7:3,1.8M, 1.11 ml) dropwise at –100° C. To the solution was added a solution of 6-ethoxycarbonyl-7-oxo-5-(3,4-methylenedioxyphenyl)cyclopent-1,3-dieno[1,2-b]pyridine(500 mg,1.55 mmol) in THF(24 ml). The temperature of the reaction solution was raised to –78° C. over 1 h. After adding water the solution was extracted with AcOEt. The organic layer was washed with brine, dried over $MgSO_4$ and concentrated under reduced pressure. The residue was purified by silica gel chromatography(E. Merck Kieselgel 60/hexane:AcOEt=1:1 to 2:3 to 1:2) to give 6-ethoxycarbonyl-7-(2-nitro-4-methoxyphenyl)-7-hydroxy-5-(3,4-methylenedioxyphenyl)cyclopent-1,3-dieno[1,2-b]pyridine(758 mg).

(3) 7-Acetoxy-6-ethoxycarbonyl-7-(2-nitro-4-methoxyphenyl)- 5-(3,4-methylenedioxyphenyl)cyclopent-1,3-dieno[1,2-b]pyridine To a AcOEt(2 ml) suspension of 6-ethoxycarbonyl-7-(2-nitro-4-methoxyphenyl)-7-hydroxy-5-(3,4-methylenedioxyphenyl)cyclopent-1,3-dieno[1,2-b]pyridine which was prepared in (2) was added TEA(1.25 ml), $Ac_2O$ (0.85 ml) and DMAP(110 mg) at 0° C. The reaction solution was stirred at room temperature for 15 min and at 50° C. for 2 h, diluted with water, adjusted at pH4 with HCl and extracted with AcOEt. The organic layer was washed with a saturated aqueous solution of $NaHCO_3$ and dried over $MgSO_4$. After removal of the solvent the residue was purified by dry column flash chromatography(E. Merck Kieselgel 60/hexane:AcOEt=2:1to 1:1 to 2:3) to give 7-acetoxy-6-ethoxycarbonyl-7-(2-nitro-4-methoxyphenyl)-5-(3,4-methylenedioxyphenyl)cyclopent-1,3-dieno[1,2-b]pyridine(753 mg).

(4) 7-(2-Amino-4-methoxyphenyl)-6-ethoxycarbonyl-5-(3,4-methylenedioxyphenyl)cyclopenteno[1,2-b]pyridine To a THF(25 ml)-EtOH(25 ml) suspension of 7-acetoxy-6-ethoxycarbonyl-7-(2-nitro-4-methoxyphenyl)-5-(3,4-methylenedioxyphenyl)cyclopent-1,3-dieno[1,2-b]pyridine which was prepared in (3) and zinc(1.43 g) was added 4N HCl-dioxane(10.9 ml) dropwise at –78° C. The reaction solution was stirred at –78° C. for 1 h and the temperature of the solution was raised to room temperature over 2 h. After adding a saturated aqueous solution of $Na_2CO_3$ the resulting insoluble material was removed by filtration and washed with AcOEt. The filtrate and washings were partitioned between water and AcOEt. The organic layer was washed with brine and dried over $MgSO_4$. After removal of the solvent the residue was purified by silica gel column chromatography(E. Merck Kieselgel 60/hexane:AcOEt= 2:1to 1:1 to 2:3) to give 7-(2-amino-4-methoxyphenyl)-6-ethoxycarbonyl-5-(3,4-methylenedioxyphenyl)cyclopenteno[1,2-b]pyridine(355 mg).

(5) 6-Ethoxycarbonyl-7-(2-tert-butoxycarbonylmetylaminophenyl)-5-(3,4-methylenedioxyphenyl)cyclopenteno[1,2-b]pyridine To a THF(3 ml) solution of 7-(2-amino-4-methoxyphenyl)-6-ethoxycarbonyl-5-(3,4-methylene dioxyphenyl)cyclopenteno[1,2-b]pyridine(150 mg,0.35 mmol) which was prepared in (4) was added TEA(1.75 ml) and tert-butyl bromoacetate(1.75 ml) and the solution was stirred under reflux for 16 h. After cooling the reaction solution was diluted with water and made weak acid with HCl and extracted with AcOEt. The organic layer was washed with brine and dried over $MgSO_4$. After removal of the solvent the residue was purified by preparative TLC(E. Merck Kieselgel $60F_{254}$/hexane:AcOEt=2:1) to give (5RS, 7SR)-6-ethoxycarbonyl-7-(2-tert-butoxycarbonylmethylaminophenyl)-5-(3,4- methylenedioxyphenyl)cyclopenteno[1,2-b]pyridine(33 mg) and (5RS,7RS)-6-ethoxycarbonyl- 7-(2-tert-butoxycarbonylmethylaminophenyl)-5-(3,4-methylenedioxyphenyl)cyclopenteno[1,2-b]pyridine(20 mg).

(6) To a methanol(0.4 ml) and dioxane(0.4 ml) solution of (5RS,7SR)-6-ethoxycarbonyl-7-(2-tert-butoxycarbonylmethylaminophenyl)-5-(3,4-methylenedioxyphenyl)cyclopenteno[1,2-b]pyridine(33 mg,0.06 mmol) which was prepared in (5) was added 6N NaOH(0.1 ml) and the solution was stirred at room temperature for 16 h. After removal of the solvent the residue was partitioned between water and AcOEt and the aqueous layer was made at pH4 with HCl and extracted with AcOEt. The organic layer was washed with brine and dried over $MgSO_4$. After removal of the solvent the residue was reprecipitated from AcOEt and hexane to give the title compound(15.3 mg) as a colorless solid.

mp: 152°–155° C.

High Resolution FAB-MS(m/e, $(C_{25}H_{22}N_2O_7+H)^+$): Calcd: 463.1506 Found: 463.1512

$^1$H-NMR(300 MHz, $CDCl_3+CD_3OD$, δ ppm): 3.47(1H, t, J=9.4 Hz), 3.78(3H, s), 3.80–3.95(2H, m), 4.62(1H, d, J=9.4 Hz), 4.92(1H, d, J=9.4 Hz), 5.95(2H, s), 6.16(1H, d, J=2.2 Hz), 6.32(1H, dd, J=2.2 Hz, 8.4 Hz), 6.78–6.82(3H, m), 6.88(1H, d, J=8.4 Hz), 7.22(1H, dd, J=5.0 Hz, 7.8 Hz), 7.42(1H, d, J=7.8 Hz), 8.36(1H, d, J=5.0 Hz)

Rf Value: 0.13(E. Merck, Kieselgel 60$F_{254}$/chloroform:methanol:acetic acid=10:1:1)

EXAMPLE 88

(5RS,7SR)-6-Ethoxycarbonyl-7-(2-carboxymethylamino-4-methoxyphenyl)-5-(3,4-methylenedioxyphenyl)cyclopenteno[1,2-b]pyridine (5RS,7SR)-6-Ethoxycarbonyl-7-(2-tert-butoxycarbonylmethylaminophenyl)-5-(3,4-methylenedioxyphenyl)cyclopenteno[1,2-b]pyridine which was prepared in Example 87-(5) was hydrolized under ice-cooling to give the title compound.

mp: 113°–117° C.

$^1$H-NMR(300 MHz, $CDCl_3$, δ ppm): 1.04(3H, t, J=7.2 Hz), 3.69–3.92(1H, m), 3.76(3H, s), 3.86(2H, q, J=7.2 Hz), 3.94–4.89(2H, m), 4.86(1H, d, J=9.6 Hz), 5.21(1H, d, J=9.9 Hz), 5.92–5.93(2H, m), 6.22(1H, d, J=2.5 Hz), 6.32(1H, dd, J=2.5 Hz, 8.5 Hz), 6.47(1H, d, J=1.8 Hz), 6.54(1H, dd, J=1.8 Hz, 8.0 Hz), 6.72(1H, d, J=8.0 Hz), 6.84(1H, d, J=8.5 Hz), 7.21(1H, dd, J=5.0 Hz, 7.3 Hz), 7.52(1H, d, J=7.3 Hz), 8.43(1H, d-like, J=5.0 Hz)

Rf Value: 0.44(E. Merck, Kieselgel 60$F_{254}$/chloroform:methanol=5:1)

Each compound in the following Examples 89 to 93 was prepared in the same manner as in Example 76 using pyridine-2,3-dicarboxylic acid anhydride.

EXAMPLE 89

(5RS,6SR,7SR)-6-Carboxy-7-(2-pyridyl)-5-(3,4-methylenedioxyphenyl)cyclopenteno[1,2-b]pyridine $^1$H-NMR(300 MHz, $CDCl_3$, δ ppm): 3.48(1H, t, J=9.4 Hz), 4.88(1H, d, J=9.4 Hz), 5.04(1H, d, J=9.4 Hz), 5.91(1H, d, J=1.4 Hz), 5.91(1H, d, J=1.4 Hz), 6.67(1H, d, J=1.7 Hz), 6.74(1H, d, J=8.0 Hz), 6.80(1H, dd, J=1.7 Hz, 8.0 Hz), 7.24(1H, dd, J=4.9 Hz, 7.8 Hz), 7.37(1H, dd, J=5.2 Hz, 7.8 Hz), 7.42(1H, d, J=7.8 Hz), 7.89(1H, t, J=7.8 Hz), 8.54(1H, d, J=7.8 Hz), 8.56(1H, d, J=5.2 Hz), 8.62(1H, d, J=4.9 Hz)

Rf Value: 0.25(E. Merck, Kieselgel 60$F_{254}$/chloroform:methanol=10:1)

EXAMPLE 90

(5RS,6SR,7SR)-6-Carboxy-5-(3-fluorophenyl)-7-(4-methoxyphenyl)cyclopenteno[1,2-b]pyridine mp: 211°–212° C.

High Resolution FAB-MS(m/e, $(C_{22}H_{18}FNO_3+H)^+$): Calcd: 364.1350 Found: 364.1347

$^1$H-NMR(300 MHz, $CD_3OD$, δ ppm): 3.21(1H, t, J=9.9 Hz), 3.78(3H, s), 4.69(2H, d, J=9.9 Hz), 6.92(2H, d, J=8.8 Hz), 7.00–7.45(4H, m), 7.12(1H, td, J=1.3 Hz, 7.9 Hz), 7.16(2H, d, J=8.8 Hz), 7.28(1H, dd, J=4.8 Hz, 7.5 Hz), 8.34(1H, d, J=4.8 Hz)

Rf Value: 0.51(E. Merck, Kieselgel 60$F_{254}$/chloroform:methanol=10:1)

EXAMPLE 91

(5RS,6SR,7SR)-6-Carboxy-5-(3-methoxyphenyl)-7-(4-methoxyphenyl)cyclopenteno[1,2-b]pyridine mp: 193°–195° C.

High Resolution FAB-MS(m/e, $(C_{23}H_{21}NO_4+H)^+$): Calcd: 376.1550 Found: 376.1541

$^1$H-NMR(300 MHz, $CDCl_3$, δ ppm): 3.36(1H, t, J=9.6 Hz), 3.77(3H, s), 3.79(3H, s), 4.65(1H, d, J=9.6 Hz), 4.72 (1H, d, J=9.6 Hz), 6.80–6.90(3H, m), 6.88(2H, d, J=8.8 Hz), 7.11–7.15(1H, m), 7.17(2H, d, J=8.8 Hz), 7.23–7.33(2H, m), 8.47(1H, td, J=1.3 Hz, 4.8 Hz)

Rf Value: 0.54(E. Merck, Kieselgel 60$F_{254}$/chloroform:methanol=10:1)

EXAMPLE 92

(5RS,6SR,7SR)-6-Carboxy-7-(4-fluorophenyl)-5-(3,4-methylenedioxyphenyl)-cyclopenteno[1,2-b]pyridine mp: 234°–236° C.

High Resolution FAB-MS(m/e, $(C_{22}H_{16}FNO_4+H)^+$): Calcd: 378.1142 Found: 378.1139

$^1$H-NMR(300 MHz, $CDCl_3$, δ ppm): 3.29(1H, t, J=10.0 Hz), 4.62(1H, d, J=10.0 Hz), 4.75(1H, d, J=10.0 Hz), 5.98(2H, s), 6.71(1H, d, J=1.3 Hz), 6.77(1H, dd, J=1.3 Hz, 7.9 Hz), 6.81(1H, d, J=7.9 Hz), 7.03–7.25(5H, m), 7.33(1H, d, J=7.6 Hz), 8.49(1H, d-like, J=4.7 Hz)

Rf Value: 0.42(E. Merck, Kieselgel 60$F_{254}$/chloroform:methanol=10:1)

EXAMPLE 93

(5RS,6SR,7SR)-6-Carboxy-5-(2-methoxyphenyl)-7-(4-methyloxyphenyl)cyclopenteno[1,2-b]pyridine mp: 194°–197° C.

High Resolution FAB-MS(m/e, $(C_{23}H_{21}NO_4+H)^+$): Calcd: 376.1549 Found: 376.1547

$^1$H-NMR(300 MHz, $CDCl_3$, δ ppm): 3.48(1H, t, J=9.6 Hz), 3.67(3H, s), 3.75(3H, s), 4.73(1H, d, J=9.6 Hz), 4.94 (1H, d, J=9.6 Hz), 6.82–6.97(4H, m), 7.06–7.19(4H, m), 7.24–7.31(2H, m), 8.43(1H, d-like, J=5.0 Hz)

Rf Value: 0.38(E. Merck, Kieselgel 60$F_{254}$/chloroform:methanol=10:1)

EXAMPLE 94

(5RS,6SR,7SR)-7-[2-(5-Oxo-4H-1,2,4-oxadiazol-3-ylmethoxy)-4-methoxyphenyl]-6-carboxy-5-(3,4-methylenedioxyphenyl)cyclopenteno[1,2-b]pyridine mp: 161°–163° C.

High Resolution FAB-MS(m/e, $(C_{26}H_{21}N_3O_8+H)^+$): Calcd: 504.1407 Found: 504.1380

$^1$H-NMR(300 MHz, DMSO-$d_6$, δ ppm): 3.28(1H, t, J=10.1 Hz), 3.76(3H, s), 4.51(1H, d, J=10.1 Hz), 4.79(1H, d, J=13.1 Hz), 4.85(1H, d, J=10.1 Hz), 5.09(1H, d, J=13.1 Hz), 6.00(2H, s), 6.58(1H, dd, J=2.4 Hz, 8.4 Hz), 6.69(1H, dd, J=1.7 Hz, 8.0 Hz), 6.75(1H, d, J=2.4 Hz), 6.79(1H, d, J=1.7 Hz), 6.86(1H, d, J=8.0 Hz), 7.11(1H, d, J=8.4 Hz), 7.15(1H, dd, J=4.9 Hz, 7.3 Hz), 7.21(1H, d, J=7.3 Hz), 8.29(1H, d, J=4.9 Hz)

Rf Value: 0.18(E. Merck, Kieselgel 60F$_{254}$/ dichloromethane:methanol=10:1)

EXAMPLE 95

6-Carboxy-5-hydroxy-5-(3,4-methylenedioxyphenyl)-7-(4-methoxyphenyl)cyclopent-1,3-dieno[2,1-d]pyrimidine (1) 4-(4-Methoxyphenylcarbonyl)pyrimidine-5-carboxylic acid ethyl ester To a THF solution(30 ml) of pyrimidine-4,5-dicarboxylic acid diethyl ester(1.46 g,6.52 mmol) which was prepared by the method described in the literature(Chem. Pharm. Bull., 1972,20,1513–1521) was added a THF solution of 4-methoxyphenyl magnesium bromide (1.25M,5.47 ml) dropwise at −78° C. The reaction solution was stirred at −78° C. for 30 min, treated with 1N HCl and extracted with AcOEt. The organic layer was washed with brine and dried over MgSO$_4$. After removal of the solvent under reduced pressure the residue was purified by silica gel column chromatography(E. Merck Kieselgel 60/chloroform) to give 4-(4-methoxyphenylcarbonyl)pyrimidine-5-carboxylic acid ethyl ester(1.57 g) as a pale yellow oil.

(2) 4-(4-Methoxyphenylcarbonyl)pyrimidine-5-carboxylic acid

To a methanol solution(15 ml) of 4-(4-methoxyphenylcarbonyl)pyrimidine-5-carboxylic acid ethyl ester was added 4N NaOH(4 ml). The solution was stirred at room temperature for 15 h. Water was added to the reaction solution to dissolve the resulting solid. After removal of methanol the aqueous layer was washed with AcOEt, made pH2 with 2N HCl and extracted with AcOEt. The organic layer was washed with brine and dried over Na$_2$SO$_4$. After removal of the solvent the residue was recrystallized from AcOEt and hexane(1:1) to give 4-(4-methoxyphenylcarbonyl)pyrimidine-5-carboxylic acid(1.06 g) as a yellow solid.

(3) 6-Ethoxycarbonyl-5-oxo-7-(4-methoxyphenylcyclopent-1,3-dieno[2,1-d]pyrimidine 6-Ethoxycarbonyl-5-oxo-7-(4-methoxyphenyl)cyclopent-1,3-dieno[2,1-d]pyrimidine was prepared in the same manner as in Example 72-(6) using 4-(4-methoxyphenylcarbonyl)pyrimidine-5-carboxylic acid which was prepared in (2).

(4) The title compound was prepared in the same manner as in Example 1-(4) and Example 29 using 6-ethoxycarbonyl-5-oxo-7-(4-methoxyphenyl)cyclopent-1,3-dieno[2,1-d]pyrimidine which was prepared in (3).

High Resolution FAB-MS(m/e, $(C_{22}H_{16}N_2O_6+H)^+$): Calcd: 405.1087 Found: 405.1083

$^1$H-NMR(300 MHz, CDCl$_3$, δ ppm): 3.89(3H, s), 5.95 (1H, d, J=1.4 Hz), 5.96(1H, d, J=1.4 Hz), 6.76(1H, d, J=8.1 Hz), 6.99(1H, d, J=1.7 Hz), 7.02(1H, dd, J=1.7 Hz, 8.1 Hz), 7.05(2H, d, J=8.8 Hz), 7.72(2H, d, J=8.8 Hz), 8.58(1H, s), 9.18(1H, s)

Rf Value: 0.86(E. Merck, Kieselgel 60F$_{254}$/ chloroform:methanol:acetic acid=10:1:1)

EXAMPLE 96

6-Carboxy-5-hydroxy-2-butyl-5-(3,4-methylenedioxyphenyl)-7-(methoxyphenyl)cyclopent-1,3-dieno[2,1-d]pyrimidine The title compound was prepared in the same manner as in Example 95 using 2-butylpyrimidine-4,5-dicarboxylic acid diethyl ester.

High Resolution FAB-MS(m/e, $(C_{26}H_{24}N_2O_6+H)^+$): Calcd: 461.1713 Found: 461.1709

$^1$H-NMR(300 MHz, CDCl$_3$, δ ppm): 0.91(3H, t, J=7.3 Hz), 1.36(2H, sext, J=7.3 Hz), 1.74(2H, quint, J=7.3 Hz), 2.93(2H, t, J=7.3 Hz), 3.89(3H, s), 5.94(2H, d, J=2.2 Hz), 6.74(1H, d, J=8.0 Hz), 6.97(1H, s), 7.00(1H, d, J=8.0 Hz), 7.02(2H, d, J=8.9 Hz), 7.76(2H, d, J=8.9 Hz), 8.48(1H, s)

Rf Value: 0.82(E. Merck, Kieselgel 60F$_{254}$/ chloroform:methanol:acetic acid=10:1:1)

Each compound in the following Example 97 and 98 was prepared in the same manner as in Example 57.

EXAMPLE 97

(5RS,6SR,7SR)-6-Carboxy-7-[2-(1-carboxypentyloxy)-4-methoxyphenyl]-5-(3,4-methylenedioxyphenyl)cyclopenteno[1,2-b]pyridine (one of diastereomers)

mp: 135°–138° C.

$^1$H-NMR(300 MHz, CDCl$_3$, δ ppm): 0.84(3H, t, J=7.2 Hz), 1.20–1.53(4H, m), 1.82–2.07(2H, m), 3.77(3H, s), 3.81(1H, t, J=10.9 Hz), 4.73(1H, d, J=10.9 Hz), 4.93(1H, dd, J=5.3 Hz, 6.7 Hz), 5.23(1H, d, J=10.9 Hz), 6.00(2H, s), 6.51(1H, dd, J=2.3 Hz, 8.6 Hz), 6.58(1H, d, J=2.3 Hz), 6.71(1H, d, J=1.6 Hz), 6.77(1H, dd, J=1.6 Hz, 7.9 Hz), 6.84(1H, d, J=7.9 Hz), 7.21(1H, dd, J=4.9 Hz, 7.7 Hz), 7.24(1H, d, J=8.6 Hz), 7.39(1H, d, J=7.7 Hz), 8.26(1H, d, J=4.9 Hz)

Rf Value: 0.67(E. Merck, Kieselgel 60F$_{254}$/ chloroform:methanol:acetic acid=10:1:1)

EXAMPLE 98

(5RS,6SR,7SR)-6-Carboxy-7-[2-(1-carboxypentyloxy)-4-methoxyphenyl]-5-(3,4-methylenedioxyphenyl)cyclopenteno[1,2-b]pyridine (the other diastereomer mp: 130°–133° C.

$^1$H-NMR(300 MHz, CDCl$_3$, δ ppm): 0.83(3H, t, J=6.7 Hz), 1.10–1.80(6H, m), 3.36(1H, t, J=10.4 Hz), 3.74(3H, s), 4.61(1H, d, J=10.4 Hz), 4.71(1H, dd, J=4.7 Hz, 7.1 Hz), 4.96(1H, d, J=10.4 Hz), 5.95–6.05(2H, m), 6.39(1H, s), 6.50(1H, d, J=8.0 Hz), 6.65(1H, s), 6.73(1H, d, J=8.9 Hz), 6.79(1H, d, J=8.9 Hz), 7.09(1H, d, J=8.0 Hz), 7.17–7.27(1H, m), 7.40(1H, d, J=7.3 Hz), 8.38–8.43(1H, m)

Rf Value: 0.45(E. Merck, Kieselgel 60F$_{254}$/ chloroform:methanol:acetic acid=10:1:1)

EXAMPLE 99

(5RS,6SR,7SR)-6-Carboxy-7-[2-[(E)-2-carboxyethenyl]-4-methoxyphenyl]-5-(3,4-methylenedioxyphenyl)cyclopenteno[1,2-b]pyridine (1) (5RS,6SR,7SR)-7-(2-trifluoromethanesulfonyloxy-4-methoxyphenyl)-6-tert-butoxycarbonyl-5-(3,4-methylenedioxyphenyl)cyclopenteno[1,2-b]pyridine To a dichloromethane solution(3.5 ml) of (5RS,6SR,7SR)-7-(2-hydroxy-4-methoxyphenyl)-6-tert-butoxycarbonyl-5-(3,4-methylenedioxyphenyl)cyclopenteno[1,2-b]pyridine which was prepared in Example 50-(5), DMPA(7.9 mg) and TEA(0.45 ml) was added a dichloromethane solution(3 ml) of N-phenyltrifluoromethanesulfoneimide(695 mg) dropwise under ice-cooling. The solution was stirred at the same temperature for 5 min and at room temperature for 1 h. After concentration under reduced pressure the residue was purified by silica gel column chromatography(E. Merck Kieselgel 60/hexane:AcOEt=2:1) to give (5RS,6SR,7SR)-7-(2-trifluoromethanesulfonyloxy-4-methoxyphenyl)-6-tert-buthoxycarbonyl-5-(3,4-methylenedioxyphenyl)cyclopenteno[1,2-b]pyridine(410 mg) as a colorless amorphous solid.

(2) (5RS,6SR,7SR)-6-Tert-butoxycarbonyl-5-(3,4-methylenedioxyphenyl)7-[(2-[(E)-2-methoxycarbonylethenyl]-4-methoxyphenyl]cyclopenteno[1,2-b]pyridine A DMF(6 ml)-TEA(8 ml) solution of (5RS,6SR,7SR)-7-(2-trifluoromethanesulfonyloxy-4-methoxyphenyl)-6-tert-butoxycarbonyl-5-(3,4-methylenedioxyphenyl)cyclopenteno[1,2-b]pyridine(411 mg,0.650 mmol) which was prepared in (1), palladium(II) acetate(15 mg), 1,3-bis(diphenylphosphino)propane(28 mg) and acrylic acid methyl ester(1.8 ml) was heated under reflux for 24 h under argon atmosphere. The catalyst was removed by filtration and washed with AcOEt. The filtrate and washings were combined and concentrated under reduced pressure. The residue was purified by silica gel column chromatography (E. Merck Kieselgel 60F/hexane:AcOEt=2:1) to give (5RS,6SR,7SR,)-6-tert-butoxycarbonyl-5-(3,4-methylenedioxyphenyl)-7-[2-[(E)-2-methoxycarbonylethenyl]-4-methoxyphenyl]cyclopenteno[1,2-b]pyridine(147 mg) as a pale brown amorphous solid.

(3) To (5RS,6SR,7SR)-6-tert-butoxycarbonyl-5-(3,4-methylenedioxyphenyl)-7-[2-[(E)-2-methoxycarbonylethenyl]-4-methoxyphenyl]cyclopenteno[1,2-b]pyridine(107 mg,0.202 mmol) was added TFA(5 ml) under ice-cooling and the solution was stirred at room temperature for 2 h. After concentration of the solution the residue was dissolved in 0.5N NaOH and washed with ether. The aqueous layer was adjusted at pH5 to 6 with 1N HCl and extracted with ether. The organic layer was washed with brine, dried over $Na_2SO_4$ and concentrated under reduced pressure to give the title compound(77.5 mg) as a pale yellow powder.

mp: 180° C. (dec.)

$^1$H-NMR(300 MHz, $CDCl_3$, δ ppm): 3.03(1H, t, J=10.2 Hz), 3.83(3H, s), 4.77(1H, d, J=10.2 Hz), 5.27(1H, d, J=10.2 Hz), 5.95(1H, d, J=1.9 Hz), 5.96(1H, d, J=1.9 Hz), 6.29(1H, d, J=15.4 Hz), 6.68(1H, d, J=1.8 Hz), 6.76(1H, dd, J=1.8 Hz, 7.9 Hz), 6.79(1H, d, J=7.9 Hz), 7.00(1H, dd, J=2.3 Hz, 8.9 Hz), 7.03(1H, d, J=8.9 Hz), 7.12(1H, d, J=2.3 Hz), 7.20(1H, dd, J=4.9 Hz, 7.9 Hz), 7.38(1H, d, J=7.9 Hz), 8.32(1H, d, J=15.4 Hz), 8.54(1H, d, J=4.9 Hz)

Rf Value: 0.37(E. Merck, Kieselgel 60F$_{254}$/dichloromethane:methanol:acetic acid=10:1:1)

EXAMPLE 100

(5RS,6SR,7SR)-6-Carboxy-5-(3,4-methylenedioxyphenyl)-7-[2-(2-methoxycarbonylethyl)-4-methoxyphenyl]cyclopenteno[1,2-b]pyridine (1) (5RS,6SR,7SR)-6-Tert-butoxycarbonyl-5-(3,4-methylenedioxyphenyl-7-[2-(2-methoxycarbonylethyl-4-methoxyphenyl]cyclopenteno1,2-b]pyridine To a solution of (5RS,6SR,7SR)-6-tert-butoxycarbonyl-5-(3,4-methylenedioxyphenyl)-7-[[(E)-2-methoxycarbonylethenyl]-4-methoxyphenyl]cyclopenteno[1,2-b]pyridine(60 mg,0.11 mmol) in AcOEt(1.5 ml) was added 10% Pd-carbon(61 mg) and the solution was stirred at room temperature under hydrogen atmosphere. After the reaction was completed, the catalyst was removed by filtration and washed with AcOEt. The filtrate and washings were combined and concentrated under reduced pressure to give (5RS,6SR,7SR)-6-tert-butoxycarbonyl-5-(3,4-methylenedioxyphenyl)-7-[2-(2-methoxycarbonylethyl)-4-methoxyphenyl]cyclopenteno[1,2-b]pyridine(59 mg) as a pale brown amorphous solid.

(2) The title compound was prepared in the same manner as in Example 50-(7).

mp: 95°–103° C.

$^1$H-NMR(300 MHz, $CDCl_3$, δ ppm): 2.52–2.80(2H, m), 2.83–3.22(2H, m), 3.38(1H, t, J=9.9 Hz), 3.63(3H, s), 3.77 (3H, s), 4.62(1H, d, J=9.9 Hz), 4.96(1H, d, J=9.9 Hz), 5.97(1H, d, J=2.4 Hz), 5.98(1H, d, J=2.4 Hz), 6.74–6.80(5H, m), 6.84–7.00(1H, m), 7.11(1H, dd, J=4.7 Hz, 7.6 Hz), 7.30(1H, d, J=7.6 Hz), 8.43(1H, d, J=4.7 Hz)

Rf Value: 0.36(E. Merck, Kieselgel 60F$_{254}$/hexane:acetone=1:1)

EXAMPLE 101

(5RS,6SR,7SR)-6-Carboxy-7-[2-(2-carboxyethyl)-4-methoxyphenyl]-5-(3,4-methylenedioxyphenyl)cyclopenteno[1,2-b]pyridine The title compound was prepared in the same manner as in Example 2 using (5RS,6SR,7SR)-6-carboxy-5-(3,4-methylenedioxyphenyl)-7-[2-(2-methoxycarbonylethyl)-4-methoxyphenyl]cyclopenteno[1,2-b]pyridine which was prepared in Example 100.

mp: 130°–139° C.

$^1$H-NMR(300 MHz, $CDCl_3$, δ ppm): 2.60–2.80(2H, m), 2.98–3.26(2H, m), 3.43(1H, t, J=9.9 Hz), 3.76(3H, s), 4.64 (1H, d, J=9.9 Hz), 5.04(1H, d, J=9.9 Hz), 5.98(1H, d, J=2.3 Hz), 5.99(1H, d, J=2.3 Hz), 6.72–6.83(5H, m), 6.90(1H, d, J=8.2 Hz), 7.19(1H, dd, J=5.0 Hz, 8.1 Hz), 7.39(1H, dt, J=1.9 Hz, 8.1 Hz), 8.38(1H, dt, J=1.9 Hz, 5.0 Hz)

Rf Value: 0.43(E. Merck, Kieselgel 60F$_{254}$/dichloromethane:methanol:acetic acid=10:1:1)

EXAMPLE 102

(5RS,6SR,7SR)-6-Carboxy-5-(3,4-methylenedioxyphenyl)-7-[2-(2-methoxycarbonylpropyl)-4-methoxyphenyl]cyclopenteno[1,2-b]pyridine(one of diastereomers)

(1) (5RS,6SR,7SR)-6-tert-butoxycarbonyl-5-(3,4-methylenedioxyphenyl)-7-[2-(2-methoxycarbonylpropenyl)-4-methoxyphenyl]cyclopenteno[1,2-b]pyridine (5RS,6SR,7SR)-6-tert-butoxycarbonyl-5-(3,4-methylenedioxyphenyl)-7-[2-(2-methoxycarbonylpropenyl)-4-methoxyphenyl]cyclopenteno[1,2-b]pyridine was prepared as a mixture of 1-propenyl isomer and 2-propenyl isomer in the same manner as in Example 99-(2) using methacrylic acid methyl ester instead of acrylic acid methyl ester.

(2) (5RS,6SR,7SR)-6-Tert-butoxycarbonyl-5-(3,4-methylenedioxyphenyl)-7-[2-(2-methoxycarbonylpropyl)-4-methoxyphenyl]cyclopenteno[1,2-b]pyridine (5RS,6SR,7SR)-6-Tert-butoxycarbonyl-5-(3,4-methylenedioxyphenyl)-7-[2-(2-methoxycarbonylpropyl)-

4-methoxyphenyl]cyclopenteno[1,2-b]pyridine was prepared in the same manner as in Example 100-(1) using the mixture of 1-propenyl isomer and 2-propenyl isomer of (5RS,6SR,7SR)-6-tert-butoxycarbonyl-5-(3,4-methylenedioxyphenyl)-7-[2-(2-methoxycarbonylpropenyl)-4-methoxyphenyl]cyclopenteno[1,2-b]pyridine which was prepared in (1).

(3) The title compound was prepared in the same manner as in Example 100-(2) using (5RS,6SR,7SR)-6-tert-butoxycarbonyl-5-(3,4-methylenedioxyphenyl)-7-[2-(2-methoxycarbonylpropyl)-4-methoxyphenyl]cyclopenteno[1,2-b]pyridine which was prepared in (2).

mp: 86°–88° C.

High Resolution FAB-MS(m/e, $(C_{28}H_{27}NO_7+H)^+$): Calcd: 490.1866 Found: 490.1856

$^1$H-NMR(300 MHz, CDCl$_3$, δ ppm): 1.16(3H, d, J=6.3 Hz), 2.73–2.86(2H, m), 3.03–3.17(1H, m), 3.32(1H, t, J=9.9 Hz), 3.59(3H, s), 3.74(3H, s), 4.60(1H, d, J=9.9 Hz), 4.95(1H, d, J=9.9 Hz), 5.96(1H, d, J=1.4 Hz), 5.97(1H, d, J=1.4 Hz), 6.72–6.81(5H, m), 6.90(1H, d, J=7.9 Hz), 7.12(1H, dd, J=4.9 Hz, 7.6 Hz), 7.31(1H, d, J=7.6 Hz), 8.45(1H, d, J=4.9 Hz)

Rf Value: 0.44(E. Merck, Kieselgel 60F$_{254}$/chloroform:methanol=10:1)

EXAMPLE 103

(5RS,6SR,7SR)-6-Carboxy-7-[2-(2-carboxypropyl)-4-methoxyphenyl]-5-(3,4-methylenedioxyphenyl)cyclopenteno[1,2-b]pyridine(one of diastereomers)

The title compound was prepared in the same manner as in Example 2 using (5RS,6SR,7SR)-6-carboxy-5-(3,4-methylenedioxyphenyl)-7-[2-(2-methoxycarbonylpropyl)-4-methoxyphenyl]cyclopenteno[1,2-b]pyridine which was prepared in 102-(3).

mp: 138°–141° C.

High Resolution FAB-MS(m/e, $(C_{27}H_{25}NO_7+H)^+$): Calcd: 476.1709 Found: 476.1717

$^1$H-NMR(300 MHz, CDCl$_3$, δ ppm): 1.30(3H, d, J=6.1 Hz), 2.68(1H, dd, J=12.2 Hz, 13.2 Hz), 2.93(1H, ddq, J=5.7 Hz, 12.2 Hz, 6.1 Hz), 3.29(1H, dd, J=5.7 Hz, 13.2 Hz), 3.65(1H, t, J=9.7 Hz), 3.76(3H, s), 4.65(1H, d, J=9.7 Hz), 5.02(1H, d, J=9.7 Hz), 6.01(2H, s), 6.73–6.84(5H, m), 6.95(1H, d, J=8.6 Hz), 7.23(1H, dd, J=5.1 Hz, 7.7 Hz), 7.44(1H, d, J=7.7 Hz), 8.30(1H, d, J=5.1 Hz)

Rf Value: 0.59(E. Merck, Kieselgel 60F$_{254}$/chloroform:methanol:acetic acid=10:1:1)

EXAMPLE 104

(5RS,6SR,7SR)-6-Carboxy-5-(3,4-methylenedioxyphenyl)-7-[2-(2-carboxy-2-propenyl)-4-methoxyphenyl]cyclopenteno[1,2-b]pyridine The title compound was prepared in the same manner as in Example 100-(2) using 2-propenyl isomer prepared by isolation and purification of (5RS,6SR,7SR)-6-tert-butoxycarbonyl-5-(3,4-methylenedioxyphenyl)-7-[2-(2-methoxycarbonylpropenyl)-4-methoxyphenyl]cyclopenteno[1,2-b]pyridine(a mixture of 1-propenyl isomer and 2-propenyl isomer) which was prepared in Example 102-(1).

mp: 97°–100° C.

High Resolution FAB-MS(m/e, $(C_{28}H_{25}NO_7+H)^+$): Calcd: 488.1710 Found: 488.1717

$^1$H-NMR(300 MHz, CDCl$_3$, δ ppm): 3.27–3.42(1H, m), 3.65–3.85(2H, m), 3.65(3H, s), 3.75(3H, s), 4.58(1H, d, J=10.0 Hz), 4.86(1H, d, J=10.0 Hz), 5.45(1H, s), 5.96(2H, s), 6.23(1H, s), 6.68–7.01(6H, m), 7.12(1H, dd, J=4.7 Hz, 7.6 Hz), 7.30(1H, d, J=7.6 Hz), 8.44(1H, d, J=4.7 Hz)

Rf Value: 0.12(E. Merck, Kieselgel 60F$_{254}$/chloroform:methanol=95:5)

EXAMPLE 105

(5RS,6SR,7SR)-6-Carboxy-7-[2-(2-carboxy-2-propenyl)-4-methoxyphenyl]-5-(3,4-methylenedioxyphenyl)cyclopenteno[1,2-b]pyridine The title compound was prepared in the same manner as in Example 2 using (5RS,6SR,7SR)-6-carboxy-5-(3,4-methylenedioxyphenyl)-7-[2-(2-methoxycarbonyl-2-propenyl)-4-methoxyphenyl]cyclopenteno[1,2-b]pyridine which was prepared in Example 104.

mp: 150°–153° C.

High Resolution FAB-MS(m/e, $(C_{27}H_{23}NO_7+H)^+$): Calcd: 474.1553 Found: 474.1538

$^1$H-NMR(300 MHz, CDCl$_3$, δ ppm): 3.28(1H, t, J=9.6 Hz), 3.65(1H, d, J=17.2 Hz), 3.75(3H, s), 3.93(1H, d, J=17.2 Hz), 4.56(1H, d, J=9.6 Hz), 5.06(1H, d, J=9.6 Hz), 5.46(1H, s), 5.96(2H, s), 6.24(1H, s), 6.65–6.94(6H, m), 7.16(1H, dd, J=4.9 Hz, 7.6 Hz), 7.36(1H, d, J=7.6 Hz), 8.50(1H, d, J=4.9 Hz)

Rf Value: 0.58(E. Merck, Kieselgel 60F$_{254}$/chloroform:methanol:acetic acid=10:1:1)

EXAMPLE 106

(5RS,6SR,7SR)-6-Carboxy-7-[2-(1,2-dihydroxy-2-methoxycarbonylethyl)-4-methoxyphenyl]-5-(3,4-methylenedioxyphenyl)cyclopenteno[1,2-b]pyridine (one of diastereomers)

(1) (5RS,6SR,7SR)-7-[2-(1,2-dihydroxy-2-methoxycarbonylethyl)-4-methoxyphenyl]-6-tert-butoxycarboxy-5-(3,4-methylenedioxyphenyl)cyclopenteno[1,2-b]pyridine To a acetone(1.0 ml)-water(0.5 ml) solution of (5RS,6SR,7SR)-6-tert-butoxycarboxy-5-(3,4-methylenedioxyphenyl)-7-[[(E)-2-methoxycarbonylethenyl]-4-methoxyphenyl]cyclopenteno[1,2-b]pyridine (108 mg,0.204 mmol) which was prepared in Example 99-(2) was added N-methylmorpholine N-oxide(45 mg) and a solution of osmium tetraoxide in tert-butanol(0.079 mmol/ml,0.50 ml). The solution was stirred at room temperature under nitrogen atmosphere for 22.5 h, treated with 1.5N sodium sulfite, stirred at room temperature for 30 min, diluted with water and extracted with AcOEt. The organic layer was washed with 10% aqueous solution of citric acid and brine and dried over Na$_2$SO$_4$. After removal of the solvent the resulting residue was purified by preparative TLC(E. Merck Kieselgel 60F$_{254}$/chloroform:methanol=95:5) to give (5RS,6SR,7SR)-7-[2-(1,2-dihydroxy-2-methoxycarbonylethyl)-4-methoxyphenyl]-6-tert-butoxycarbonyl-5-(3,4-methylenedioxyphenyl)cyclopenteno[1,2-b]pyridine(21 mg, the other diastereomer).

(2) The title compound was prepared in the same manner as in Example 50-(7) using one of diastereomer of (5RS,6SR,7SR)-7-[2-(1,2-dihydroxy-2-methoxycarbonylethyl)-4-methoxyphenyl]-6-tert-butoxycarbonyl-5-(3,4-methylenedioxyphenyl)cyclopenteno[1,2-b]pyridine which was prepared in (1).

mp: 133°–136° C.

High Resolution FAB-MS(m/e, $(C_{27}H_{25}NO_9+H)^+$): Calcd: 508.1607 Found: 508.1602

¹H-NMR(300 MHz, CDCl₃+CD₃OD, δ ppm): 3.52(1H, t, J=9.5 Hz), 3.82(6H, s), 4.54(1H, brs), 4.67(1H, d, J=9.5 Hz), 5.15(1H, d, J=9.5 Hz), 5.50(1H, brs), 5.99(2H, s), 6.77(1H, s), 6.78–6.87(3H, m), 6.97(1H, d, J=8.5 Hz), 7.17(1H, dd, J=5.0 Hz, 7.6 Hz), 7.37(1H, d, J=2.7 Hz), 7.39(1H, d, J=7.6 Hz), 8.27(1H, d, J=5.0 Hz)

Rf Value: 0.53(E. Merck, Kieselgel 60F$_{254}$/chloroform:methanol:acetic acid=10:1:1)

EXAMPLE 107

(5RS,6SR,7SR)-6-Carboxy-7-[2-(1,2-dihydroxy-2-methoxycarbonylethyl)-4-methoxyphenyl]-5-(3,4-methylenedioxyphenyl)cyclopenteno[1,2-b]pyridine
(the other diastereomer)

The title compound was prepared in the same manner as in Example 106 using the other diastereomer which was prepared in Example 106-(1).

mp: 134°–137° C.

High Resolution FAB-MS(m/e, (C₂₇H₂₅NO₉+H)⁺): Calcd: 508.1607 Found: 508.1590

¹H-NMR(300 MHz, CDCl₃+CD₃OD, δ ppm): 3.35(1H, t, J=9.9 Hz), 3.81(3H, s), 3.83(3H, s), 4.53(1H, d, J=2.0 Hz), 4.65(1H, d, J=9.9 Hz), 5.03(1H, d, J=9.9 Hz), 5.63(1H, brs), 5.98(1H, d, J=1.4 Hz), 5.99(1H, d, J=1.4 Hz), 6.76(1H, s), 6.78–6.86(3H, m), 6.89(1H, d, J=8.6 Hz), 7.20(1H, dd, J=4.9 Hz, 7.7 Hz), 7.21(1H, d, J=2.6 Hz), 7.40(1H, d, J=7.7 Hz), 8.30(1H, d, J=4.9 Hz)

Rf Value: 0.41(E. Merck, Kieselgel 60F$_{254}$/chloroform:methanol:acetic acid=10:1:1)

Each compound in the following Examples 108 and 109 was prepared in the same manner as in Example 2 using compounds of Examples of 106 and 107.

EXAMPLE 108

(5RS,6SR,7SR)-6-Carboxy-7-[2-(2-carboxy-1,2-dihydroxyethyl)-4-methoxyphenyl]-5-(3,4-methylenedioxyphenyl)cyclopenteno[1,2-b]pyridine
(one of diastereomers)

mp: 189°–191° C.

High Resolution FAB-MS(m/e, (C₂₆H₂₃NO₉+H)⁺): Calcd: 494.1451 Found: 494.1440

¹H-NMR(300 MHz, DMSO-d₆, δ ppm): 3.47(1H, t, J=10.1 Hz), 3.74(3H, s), 4.22(1H, brs), 4.55(1H, d, J=10.1 Hz), 4.93(1H, d, J=10.1 Hz), 5.41(1H, brs), 6.02(2H, s), 6.76(1H, dd, J=2.9 Hz, 8.6 Hz), 6.83(1H, dd, J=1.5 Hz, 8.0 Hz), 6.86–6.97(2H, m), 7.09(1H, d, J=8.6 Hz), 7.14–7.20 (2H, m), 7.24(1H, d, J=7.3 Hz), 8.27(1H, d, J=4.9 Hz)

Rf Value: 0.07(E. Merck, Kieselgel 60F$_{254}$/chloroform:methanol:acetic acid=10:1:1)

EXAMPLE 109

(5RS,6SR,7SR)-6-Carboxy-7-[2-(2-carboxy-1,2-dihydroxyethyl)-4-methoxyphenyl]-5-(3,4-methylenedioxyphenyl)cyclopenteno[1,2-b]pyridine
(the other diastereomer)

mp: 168°–170°0 C.

High Resolution FAB-MS(m/e, (C₂₆H₂₃NO₉+H)⁺): Calcd: 494.1451 Found: 494.1446

¹H-NMR(300 MHz, CDCl₃+CD₃OD, δ ppm): 3.36(1H, t, J=9.9 Hz), 3.84(3H, s), 4.46(1H, d, J=2.4 Hz), 4.65(1H, d, J=9.9 Hz), 5.05(1H, d, J=9.9 Hz), 5.68(1H, brs), 5.98(1H, d, J=1.4 Hz), 5.99(1H, d, J=1.4 Hz), 6.75(1H, s), 6.80(1H, d, J=8.6 Hz), 6.83(1H, d, J=8.6 Hz), 6.84(1H, dd, J=2.9 Hz, 8.6 Hz), 6.89(1H, d, J=8.6 Hz), 7.23(1H, dd, J=5.3 Hz, 7.8 Hz), 7.26(1H, d, J=2.9 Hz), 7.42(1H, d, J=7.8 Hz), 8.30(1H, d, J=5.3 Hz)

Rf Value: 0.03(E. Merck, Kieselgel 60F$_{254}$/chloroform:methanol:acetic acid=10:1:1)

EXAMPLE 110

(5RS,6SR,7SR)-6-Carboxy-7-[2-(3-hydroxy-1-propynyl)-4-methoxyphenyl]-5-(3,4-methylenedioxyphenyl)cyclopenteno[1,2-b]pyridine (1) 3-(Tetrahydropyranyloxy)-1-tributylstanyl-1-propyne To an ether(20 ml) solution of 3-(tetrahydropyranyloxy)-1-propyne(2.00 g,14.3 mmol) which was prepared by the method described in the literature[see J. Chem. Soc. Perkin 1,1089(1992)] was added a butyl lithium-hexane solution (1.66M,8.60 ml) dropwise at −78° C. and the solution was stirred at the same temperature for 30 min. To the solution was added tributylstanyl chloride(3.87 ml) dropwise at −78° C. and the solution was stirred at the same temperature for 1 h. After adding water at −78° C. to quench the reaction the temperature of the mixture was raised to room temperature. The organic layer was separated, washed with brine and dried over MgSO₄. The solvent was evaporated to give 3-(tetrahydropyranyloxy)-1-tributylstanyl-1-propyne(6.13 g).

(2) (5RS,6SR,7SR)-7-[2-(3-Tetrahydropyranyloxy-1-propynyl)-4-methoxypheny]-6-tert-butoxycarbonyl-5-(3,4-methylenedioxyphenyl)cyclopenteno[1,2-b]pyridine To a DMF(1 ml) solution of (5RS,6SR,7SR)-7-(2-trifluoromethanesulfonyl-4-methoxyphenyl]-6-tert-butoxycarbonyl-5-(3,4-methylenedioxyphenyl)cyclopenteno[1,2-b]pyridine(30 mg,0.0505 mmol) which was prepared in Example 99-(1) and 3-(tetrahydropyranyloxy)-1-tributylstanyl-1-propyne which was prepared in (1) were added lithium chloride(7 mg) and palladium(II) chloride bis-triphenylphosphine complex(2 mg) at room temperature under nitrogen atmosphere. The mixture was stirred at 100° C. for 2 h and cooled to room temperature. After removal of DMF the residue was dissolved in AcOEt, treated with a 40% aqueous KF solution(1 ml) and stirred at room temperature for 30 min. The resulting tributylstanyl fluoride was removed by Celite-filtration. The filtrate and washings were combined, washed with brine and dried over MgSO₄. After removal of the solvent the residue was purified by preparative TLC (E. Merck Kieselgel 60F$_{254}$/AcOEt:hexane=1:1) to give (5RS,6SR,7SR)-7-[2-(3-tetrahydropyranyloxy-1-propynyl)-4-methoxyphenyl]-6-tert-butoxycarbonyl-5-(3,4-methylenedioxyphenyl)cyclopenteno[1,2-b]pyridine(17.2 mg).

(3) (5RS,6SR,7SR)-7-[2-(3-Hydroxy-1-propynyl)-4-methoxyphenyl]-6-tert-butoxycarbonyl-5-(3,4-methylenedioxyphenyl)cyclopenteno[1,2-b]pyridine To a ethanol solution(0.5 ml) of (5RS,6SR,7SR)-7-[2-(3-tetrahydropyranyloxy-1-propynyl)-4-methoxyphenyl]-6-tert-butoxycarbonyl-5-(3,4-methylenedioxyphenyl)cyclopenteno[1,2-b]pyridine(31.0 mg,0.0532 mmol) which was prepared in (2) was added pyridium p-toluene sulfonate (13 mg) and the mixture was subjected to react at room temperature to give (5RS,6SR,7SR)-7-[2-(3-hydroxy-1-propynyl)-4-methoxyphenyl]-6-tert-butoxycarbonyl-5-(3,4-methylenedioxyphenyl)cyclopenteno[1,2-b]pyridine(18.4 mg).

(4) The title compound was prepared in the same manner as in Example 50-(7) using (5RS,6SR,7SR)-7-[2-(3- hydroxy-1-propynyl)]-4-methoxyphenyl]-6-tert-butoxycarbonyl-5-(3,4-methylenedioxyphenyl)cyclopenteno[1,2-b]pyridine which was prepared in (3).

mp: -200° C. (dec.)

High Resolution FAB-MS(m/e, $(C_{26}H_{21}NO_6+H)^+$): Calcd: 444.1447 Found: 444.1458

$^1$H-NMR(300 MHz, CD$_3$OD, δ ppm): 3.30(1H, t, J=9.9 Hz), 3.79(3H, s), 4.19(2H, s), 4.62(1H, d, J=9.9 Hz), 5.08 (1H, d, J=9.9 Hz), 5.94(2H, s), 6.77–6.82(3H, m), 6.92(1H, dd, J=2.6 Hz, 8.6 Hz), 7.02(1H, d, J=2.6 Hz), 7.07(1H, d, J=8.6 Hz), 7.25(1H, dd, J=4.9 Hz, 7.5 Hz), 7.38(1H, dt, J=1.9 Hz, 7.5 Hz), 8.29(1H, dt, J=1.9 Hz, 4.9 Hz)

Rf Value: 0.1 (E. Merck, Kieselgel 60F$_{254}$/AcOEt:hexane=1:1)

EXAMPLE 111

(5RS,6SR,7SR)-6-Carboxy-7-[2-[(Z)-(3-hydroxy-1-propenyl)-4-methoxyphenyl]-5-(3,4-methylenedioxyphenyl)cyclopenteno[1,2-b]pyridine (1) (5RS,6SR,7SR)-7-[2-(3-Tetrahydropyranyloxy-1-propenyl)-4-methoxyphenyl]-6-tert-butoxycarbonyl-5-(3,4-methylenedioxyphenyl)cyclopenteno[1,2-b]pyridine The mixture of (3-tetrahydropyranyloxy-1-propenyl) tributyltin(320 mg) which was prepared by the method described in the literature[J-Org. Chem., 40, 2265(1975)], (5RS,6SR,7SR)-7-(2-trifluoromethanesulfonyloxy-4-methoxy)-6-tert-butoxycarbonyl-5-(3,4-methylenedioxyphenyl)cyclopenteno[1,2-b]pyridine(264 mg,0.445 mmol) which was prepared in Example 99-(1), palladium (II) dichloride bis-triphenylphosphin complex (25.8 mg), lithium chloride(57.0 mg), 2,6-di-tertbutyl-4-methylphenol(20 mg) and DMF(2.2 ml) in a schlenk reactor was heated under nitrogen atmosphere at 110° C. in an oil bath for 17 h with stirring. The reaction solution was cooled and concentrated under reduced pressure. The residue was treated with ether(4 ml) and a 40% aqueous KF solution(2 ml) and the mixture was stirred at room temperature for 30 min. The insoluble material was removed by Celite-filtration. The filtrate and washings were combined, washed with a 40% aqueous KF solution, water and brine, dried over Na$_2$SO$_4$ and concentrated under reduced pressure. The residue was purified by silica gel chromatography(E. Merck Kieselgel 60/hexane:AcOEt=2:1) to give (Z)-1-propenyl isomer(42.8 mg), (E)-1-propenyl isomer(57.7 mg) and the mixture (150.5 mg,Z/E=1/2.4) of (5RS,6SR,7SR)-7-[2-(3-tetrahydropyranyloxy-1-propenyl)-4-methoxyphenyl]-6-tert-butoxycarbonyl-5-(3,4-methylenedioxyphenyl)cyclopenteno[1,2-b]pyridine.

(2) The title compound was prepared in the same manner as in Example 110-(3) and (4) using (5RS,6SR,7SR)-7-[2-(3-tetrahydropyranyloxy-1-propenyl)-4-methoxyphenyl]-6-tert-butoxycarbonyl-5-(3,4-methylenedioxyphenyl)cyclopenteno[1,2-b]pyridine which was prepared in (1).

High Resolution FAB-MS(m/e, $(C_{26}H_{23}NO_6+H)^+$): Calcd: 446.1604 Found: 446.1581

$^1$H-NMR(300 MHz, DMSO-d$_6$, δ ppm): 3.10(1H, t, J=10.0 Hz), 3.73(3H, s), 3.97(1H, ddd, J=1.2 Hz, 6.5 Hz, 13.3 Hz), 4.03(1H, ddd, J=1.2 Hz, 6.5 Hz, 13.3 Hz), 4.50 (1H, d, J=10.0 Hz), 4.74(1H, d, J=10.0 Hz), 5.78(1H, td, J=6.5 Hz, 11.3 Hz), 6.00(2H, s), 6.44–6.54(1H, m), 6.65(1H, d, J=2.7 Hz), 6.74(1H, dd, J=1.6 Hz, 8.0 Hz), 6.79(1H, d, J=1.6 Hz), 6.80(1H, dd, J=2.7 Hz, 8.5 Hz), 6.88(1H, d, J=8.0 Hz), 6.99(1H, d, J=8.5 Hz), 7.16(1H, dd, J=4.6 Hz, 7.7 Hz), 7.23(1H, d, J=7.7 Hz), 8.29(1H, d, J=4.6 Hz)

Rf Value: 0.24(E. Merck, Kieselgel 60F$_{254}$/chloroform:methanol=15:1)

EXAMPLE 112

(5RS,6SR,7SR)-6-Carboxy-7-[2-[(E)-(3-hydroxy-1-propenyl)]-4-methoxyphenyl]-5-(3,4-methylenedioxyphenyl)cyclopenteno[1,2-b]pyridine The title compound was prepared in the same manner as in Example 110-(3) and (4) using (E)-propenyl isomer of (5RS,6SR,7SR)-7-[2-(3-tetrahydropyranyloxy-1-propenyl)-4-methoxyphenyl]-6-tert-butoxycarbonyl-5-(3,4-methylenedioxyphenyl)cyclopenteno[1,2-b]pyridine which was prepared in Example 111-(1).

mp: 218°–221° C.

High Resolution FAB-MS(m/e, $(C_{26}H_{23}NO_6+H)^+$): Calcd: 446.1604 Found: 446.1621

$^1$H-NMR(300 MHz, CDCl$_3$, δ ppm): 3.18(1H, t, J=9.5 Hz), 3.79(3H, s), 4.12–4.26(2H, m), 4.54(1H, d, J=9.5 Hz), 5.10(1H, d, J=9.5 Hz), 5.94(1H, d, J=1.4 Hz), 5.95(1H, d, J=1.4 Hz), 6.07(1H, td, J=5.7 Hz, 15.5 Hz), 6.67(1H, brs), 6.71(1H, d, J=8.0 Hz), 6.76(1H, d, J=8.0 Hz), 6.66–6.86(1H, m), 6.81(1H, dd, J=2.7 Hz, 8.5 Hz), 6.91(1H, d, J=2.7 Hz), 6.93(1H, d, J=8.5 Hz), 7.15(1H, dd, J=4.8 Hz, 7.7 Hz), 7.33(1H, d, J=7.7 Hz), 8.47(1H, d, J=4.8 Hz)

Rf Value: 0.33(E. Merck, Kieselgel 60F$_{254}$/chloroform:methanol=10:1)

EXAMPLE 113

(5RS,6SR,7SR)-6-Carboxy-7-[2-(3-hydroxypropyl)-4-methoxyphenyl]-5-(3,4-methylenedioxyphenyl)cyclopenteno[1,2-b]pyridine The title compound was prepared by hydrogenation of a mixture of E/Z -isomers of (5RS,6SR,7SR)-7-[2-(3-tetrahydropyranyloxy-1-propenyl)-4-methoxyphenyl]-6-tert-butoxycarbonyl-5-(3,4-methylenedioxyphenyl)cyclopenteno[1,2-b]pyridine which was prepared in Example 111-(1) using palladium black as a catalyst, followed by the same reactions as in Example 110-(3) and (4).

mp: 222°–226° C.

High Resolution FAB-MS(m/e, $(C_{26}H_{25}NO_6+H)^+$): Calcd: 448.1760 Found: 448.1770

$^1$H-NMR(300 MHz, DMSO-d$_6$, δ ppm): 1.62–1.78(2H, m), 2.48–2.86(2H, m), 3.19(1H, t, J=10.2 Hz), 3.33–3.50 (2H, m), 3.72(3H, s), 4.53(1H, d, J=10.2 Hz), 4.83(1H, d, J=10.2 Hz), 6.01(2H, s), 6.70(1H, dd, J=2.7 Hz, 8.4 Hz), 6.74(1H, d, J=2.7 Hz), 6.78(1H, dd, J=1.6 Hz, 8.0 Hz), 6.86(1H, d, J=1.6 Hz), 6.90(1H, d, J=8.0 Hz), 6.95(1H, d, J=8.4 Hz), 7.16(1H, dd, J=4.6 Hz, 7.4 Hz), 7.23(1H, td, J=1.4 Hz, 7.4 Hz), 8.30(1H, td, J=1.4 Hz, 4.6 Hz)

Rf Value: 0.12(E. Merck, Kieselgel 60F$_{254}$/chloroform:methanol=15:1)

Each compound in the following Examples 114 and 115 was prepared in the same manner as in Example 111-(1) and Example 106 using vinyltributyl tin.

EXAMPLE 114

(5RS,6SR,7SR)-6-Carboxy-7-[2-(1,2-dihydroxyethyl)-4-methoxyphenyl]-5-(3,4-methylenedioxyphenyl)cyclopenteno[1,2-b]pyridine (one of diastereomers.)

mp: 140°–144° C.

High Resolution FAB-MS(m/e, $(C_{25}H_{23}NO_7+H)^+$): Calcd: 450.1553 Found: 450.1558

$^1$H-NMR(300 MHz, acetone-$d_6$, δ ppm): 3.47(1H, t, J=9.9 Hz), 3.56(1H, dd, J=8.0 Hz, 11.6 Hz), 3.79(3H, s), 3.89(1H, dd, J=4.4 Hz, 11.6 Hz), 4.64(1H, d, J=9.9 Hz), 5.09(1H, d, J=9.9 Hz), 5.26(1H, brs), 6.02(2H, s), 6.79(1H, dd, J=2.5 Hz, 8.6 Hz), 6.85–6.93(3H, m), 7.04(1H, d, J=8.6 Hz), 7.20–7.26(2H, m), 7.35(1H, d, J=7.1 Hz), 8.33(1H, d, J=4.5 Hz)

Rf Value: 0.30(E. Merck, Kieselgel 60F$_{254}$/chloroform:methanol=10:1)

EXAMPLE 115

(5RS,6SR,7SR)-6-Carboxy-7-[2-(1,2-dihydroxyethyl)-4-methoxyphenyl]-5-(3,4-methylenedioxyphenyl)cyclopenteno[1,2-b]pyridine (the other diastereomer).

mp: 132°–135° C.

High Resolution FAB-MS(m/e, $(C_{25}H_{23}NO_7+H)^+$): Calcd: 450.1553 Found: 450.1563

$^1$H-NMR(300 MHz, acetone-$d_6$, δ ppm): 3.50–3.80(3H, m), 3.78(3H, s), 4.67(1H, d, J=9.2 Hz), 5.05–5.20(2H, m), 6.01(2H, s), 6.80(1H, dd, J=3.1 Hz, 8.5 Hz), 6.87(3H, s), 7.09–7.16(2H, m), 7.19(1H, dd, J=4.8 Hz, 7.5 Hz), 7.33(1H, d, J=7.5 Hz), 8.32(1H, d, J=4.8 Hz)

Rf Value: 0.27(E. Merck, Kieselgel 60F$_{254}$/chloroform:methanol=10:1)

A Z/E mixture of (5RS,6SR,7SR)-7-[2-(3-tetrahydropyranyloxy-1-propenyl)-4-methoxyphenyl]-6-tert-butoxycarbonyl-5-(3,4-methylenedioxyphenyl)cyclopenteno[1,2-b]pyridine was treated with a solution of diborane in dimethylsulfide and THF under ice-cooling to room temperature and treated with an aqueous 35% hydrogen peroxide solution to give a mixture of hydroxy isomers. The tetrahydropyranyl group of the hydroxyl isomers was removed and the resulting material was separated to each of isomers by preparative TLC(E. Merck Kieselgel 60/chloroform:AcOEt=5:2, then AcOEt only) in the same manner as in Example 110-(3) and followed by the same treatment as in Example 110-(4) to give each compound in the following Examples 116–119.

EXAMPLE 116

(5RS,6SR,7SR)-6-Carboxy-7-[2-(1,3-dihydroxypropyl)-4-methoxypheny]-5-(3,4-methylenedioxyphenyl)cyclopenteno[1,2-b]pyridine (one of diastereomers)

mp: 115°–120° C.

High Resolution FAB-MS(m/e, $(C_{26}H_{25}NO_7+H)^+$): Calcd: 464.1709 Found: 464.1716

$^1$H-NMR(300 MHz, CD$_3$OD, δ ppm): 1.88–2.17(2H, m), 3.27(1H, t, J=9.8 Hz), 3.65–3.75(2H, m), 3.79(3H, s), 4.59(1H, d, J=9.8 Hz), 5.09(1H, d, J=9.8 Hz), 5.28–5.40(1H, m), 5.94(2H, s), 6.74–6.84(4H, m), 6.89(1H, d, J=8.5 Hz), 7.15(1H, d, J=2.7 Hz), 7.25(1H, dd, J=4.8 Hz, 7.5 Hz), 7.39(1H, d, J=7.5 Hz), 8.29(1H, d, J=4.8 Hz)

Rf Value: 0.07(E. Merck, Kieselgel 60F$_{254}$/chloroform:methanol=10:1)

EXAMPLE 117

(5RS,6SR,7SR)-6-Carboxy-7-[2-(1,3-dihydroxypropyl)-4-methoxypheny]-5-(3,4-methylenedioxyphenyl)cyclopenteno[1,2-b]pyridine (the other diastereomer)

mp: 104°–108° C.

High Resolution FAB-MS(m/e, $(C_{26}H_{25}NO_7+H)^+$): Calcd: 464.1709 Found: 464.1725

$^1$H-NMR(300 MHz, CDCl$_3$, δ ppm): 1.78–1.94(1H, m), 1.94–2.13(1H, m), 3.45(1H, t, J=9.3 Hz), 3.67–3.92(2H, m), 3.76(3H, s), 4.67(1H, d, J=9.3 Hz), 5.36(1H, m), 5.47(1H, d, J=9.3 Hz), 5.97(2H, s), 6.63–6.84(5H, m), 7.04(1H, brs), 7.41(1H, dd, J=5.5 Hz, 7.4 Hz), 7.68(1H, d, J=7.4 Hz), 8.41(1H, d, J=5.5 Hz)

Rf Value: 0.10(E. Merck, Kieselgel 60F$_{254}$/chloroform:methanol=10:1)

EXAMPLE 118

(5RS,6SR,7SR)-6-Carboxy-7-[2-(2,3-dihydroxypropyl)-4-methoxypheny]-5-(3,4-methylenedioxyphenyl)cyclopenteno[1,2-b]pyridine (on of diastereomers)

mp: 115°–120° C.

High Resolution FAB-MS(m/e, $(C_{26}H_{25}NO_7+H)^+$): Calcd: 464.1709 Found: 464.1699

$^1$H-NMR(300 MHz, CDCl$_3$, δ ppm): 2.73(1H, m), 3.06(1H, dd, J=9.5 Hz, 13.3 Hz), 3.30(1H, t, J=9.4 Hz), 3.44–3.76(2H, m), 3.72(3H, s), 3.80–3.97(1H, m), 4.52(1H, d, J=9.4 Hz), 5.20(1H, d, J=9.4 Hz), 5.96(2H, s), 6.66–6.80(5H, m), 6.84(1H, d, J=8.3 Hz), 7.21(1H, dd, J=5.3 Hz, 7.6 Hz), 7.39(1H, d, J=7.6 Hz), 8.34(1H, d, J=5.3 Hz)

Rf Value: 0.13(E. Merck, Kieselgel 60F$_{254}$/chloroform:methanol=10:1)

EXAMPLE 119

(5RS,6SR,7SR)-6-Carboxy-7-[2-(2,3-dihydroxypropyl)-4-methoxyphenyl]-5-(3,4-methylenedioxyphenyl)cyclopenteno[1,2-b]pyridine (the other diastereomer)

mp: 208°–212° C.

High Resolution FAB-MS(m/e, $(C_{26}H_{25}NO_7+H)^+$): Calcd: 464.1709 Found: 464.1722

$^1$H-NMR(300 MHz, CDCl$_3$+CD$_3$OD, δ ppm): 2.40–2.75 (1H, m), 3.18(1H, dd, J=4.2 Hz, 13.8 Hz), 3.34(1H, t, J=9.7 Hz), 3.57(1H, dd, J=6.7 Hz, 11.3 Hz), 3.67(1H, dd, J=3.8 Hz, 11.3 Hz), 3.80(3H, s), 3.89–4.00(1H, m), 4.62(1H, d, J=9.7 Hz), 4.99(1H, d, J=9.7 Hz), 5.97(1H, d, J=1.4 Hz), 5.98(1H, d, J=1.4 Hz), 6.75(1H, brs), 6.76–6.84(4H, m), 6.88(1H, d, J=8.2 Hz), 7.17(1H, dd, J=5.0 Hz, 7.6 Hz), 7.38(1H, d, J=7.6 Hz), 8.31(1H, d, J=5.0 Hz)

Rf Value: 0.13(E. Merck, Kieselgel 60F$_{254}$/chloroform:methanol=10:1)

Each compound in the following Examples 120–123 was prepared in the same manner as in Example 106-(1) and Example 111-(3), (4) using (E)-propenyl isomer (Examples 120 and 121) and (Z)-isomer (Examples 123 and 123) of (5RS,6SR,7SR)-7-[2-(3-tetrahydropyranyloxy-1-propenyl)-4-methoxypheny]-6-tert-butoxycarbonyl-5-(3,4-methylenedioxyphenyl)cyclopenteno[1,2-b]pyridine.

EXAMPLE 120

(5RS,6SR,7SR)-6-Carboxy-7-[2-(1,2,3-trihydroxypropyl)-4-methoxyphenyl]-5-(3,4-methylenedioxyphenyl)cyclopenteno[1,2-b]pyridine (one of diastereomers derived from (E)-propenyl isomer)

mp: 127°–129° C.

High Resolution FAB-MS(m/e, $(C_{26}H_{25}NO_8+H)^+$): Calcd: 480.1658 Found: 480.1652

$^1$H-NMR(300 MHz, CDCl$_3$, δ ppm): 3.32(1H, dd, J=9.2 Hz, 10.6 Hz), 3.40–3.55(2H, m), 3.64(3H, s), 3.95–4.05(1H, m), 4.49(1H, d, J=9.2 Hz), 5.02–5.11(1H, m), 5.25(1H, d, J=10.6 Hz), 5.94(2H, s), 6.61–6.68(2H, m), 6.72–6.81(2H, m), 6.88(1H, d, J=8.9 Hz), 6.97(1H, d, J=2.0 Hz), 7.06(1H, dd, J=5.3 Hz, 7.6 Hz), 7.32(1H, d, J=7.6 Hz), 8.22(1H, d, J=5.3 Hz)

Rf Value: 0.19(E. Merck, Kieselgel 60F$_{254}$/chloroform:methanol:acetic acid=10:1:1)

EXAMPLE 121

(5RS,6SR,7SR)-6-Carboxy-7-[2-(1,2,3-trihydroxypropyl)-4-methoxyphenyl]-5-(3,4-methylenedioxyphenyl)cyclopenteno[1,2-b]pyridine (the other diastereomer derived from (E)-propenyl isomer)

mp: 143°–146° C.

High Resolution FAB-MS(m/e, $(C_{26}H_{25}NO_8+H)^+$): Calcd: 480.1658 Found: 480.1660

$^1$H-NMR(300 MHz, CDCl$_3$+CD$_3$OD, δ ppm): 3.34(1H, t, J=9.8 Hz), 3.63(1H, dd, J=5.3 Hz, 11.6 Hz), 3.70(1H, dd, J=4.7 Hz, 11.6 Hz), 3.83(3H, s), 3.91(1H, ddd, J=4.7 Hz, 5.2 Hz, 5.3 Hz), 4.63(1H, d, J=9.8 Hz), 5.11(1H, d, J=9.8 Hz), 5.21(1H, d, J=5.2 Hz), 5.98(1H, d, J=1.4 Hz), 5.99(1H, d, J=1.4 Hz), 6.76(1H, d, J=2.6 Hz), 7.20(1H, dd, J=5.1 Hz, 7.7 Hz), 7.40(1H, td, J=1.4 Hz, 7.7 Hz), 8.30(1H, td, J=1.4 Hz, 5.1 Hz)

Rf Value: 0.19(E. Merck, Kieselgel 60F$_{254}$/chloroform:methanol:acetic acid=10:1:1)

EXAMPLE 122

(5RS,6SR,7SR)-6-Carboxy-7-[2-(1,2,3-trihydroxypropyl)-4-methoxyphenyl]-5-(3,4-methylenedioxyphenyl)cyclopenteno[1,2-b]pyridine (one of diastereomers derived from (Z)-propenyl isomer).

High Resolution FAB-MS(m/e, $(C_{26}H_{25}NO_8+H)^+$): Calcd: 480.1658 Found: 480.1630

$^1$H-NMR(300 MHz, CD$_3$OD, δ ppm): 3.49(1H, t, J=10.0 Hz), 3.72–3.94(3H, m), 3.82(3H, s), 4.69(1H, d, J=10.0 Hz), 5.22(1H, d, J=6.3 Hz), 5.38(1H, d, J=10.0 Hz), 5.96(2H, s), 6.80–6.88(3H, m), 6.89(1H, dd, J=2.8 Hz, 8.6 Hz), 7.04(1H, d, J=8.6 Hz), 7.25(1H, d, J=2.8 Hz), 7.53(1H, dd, J=5.8 Hz, 7.7 Hz), 7.72(1H, d, J=7.7 Hz), 8.37(1H, d, J=5.5 Hz)

Rf Value: 0.23(E. Merck, Kieselgel 60F$_{254}$/chloroform:methanol:acetic acid=10:1:1)

EXAMPLE 123

(5RS,6SR,7SR)-6-Carboxy-7-[2-(1,2,3-trihydroxypropyl)-4-methoxyphenyl-5-(3,4-methylenedioxyphenyl)cyclopenteno[1,2-b]pyridine (the other diastereomer derived from (Z)-propenyl isomer)

High Resolution FAB-MS(m/e, $(C_{26}H_{25}NO_8+H)^+$): Calcd: 480.1658 Found: 480.1667

$^1$H-NMR(300 MHz, CDCl$_3$+CD$_3$OD, δ ppm): 3.54(1H, t, J=9.6 Hz), 3.75–3.95(3H, m), 3.82(3H, s), 4.73(1H, d, J=9.6 Hz), 5.05(1H, d, J=7.6 Hz), 5.43(1H, d, J=9.6 Hz), 6.00(2H, s), 6.78(1H, brs), 6.81(1H, dd, J=1.5 Hz, 8.0 Hz), 6.85(1H, d, J=8.0 Hz), 6.87(1H, dd, J=2.7 Hz, 8.6 Hz), 6.95(1H, d, J=8.6 Hz), 7.15(1H, d, J=2.7 Hz), 7.45(1H, dd, J=5.5 Hz, 7.6 Hz), 7.67(1H, d, J=7.6 Hz), 8.42(1H, d, J=5.5 Hz)

Rf Value: 0.26(E. Merck, Kieselgel 60F$_{254}$/chloroform:methanol:acetic acid=10:1:1)

EXAMPLE 124

(5RS,6SR,7SR)-6-Carboxy-7-[2-(1-carboxy-2-hydroxyethoxy)-4-methoxyphenyl]-2-propylamino-5-(3,4-methylenedioxyphenyl)cyclopenteno[1,2-b]pyridine(one of diastereomers)

(1) (5RS,6SR,7SR)-6-Tert-butoxycarbonyl-7-(2-benzyloxy-4-methoxyphenyl)-5-(3,4-methylenedioxyphenyl)cyclopenteno[1,2-b]pyridine N-oxide To a dichloromethane(4 ml) solution of (5RS,6SR,7SR)-6-tert-butoxycarbonyl-7-(2-benzyloxy-4-methoxyphenyl)-5-(3,4-methylenedioxyphenyl)cyclopenteno[1,2-b]pyridine (386 mg,0.70 mmol) which was prepared in Example 50-(4) was added mCPBA(190 mg) at 0° C. over 5 min. The mixture was stirred at 0° C. 1.5 h and at room temperature for 4 h, diluted with dichloromethane, washed with a saturated aqueous solution of NaHCO$_3$ and brine and dried over MgSO$_4$. After removal of the solvent the residue was purified by dry column flash chromatography(E. Merck Kieselgel 60/chloroform:methanol=50:1 to 30:1) to give (5RS,6SR,7SR)-6-tert-butoxycarbonyl-7-(2-benzyloxy-4-methoxyphenyl)-5-(3,4-methylenedioxyphenyl)cyclopenteno[1,2-b]pyridine N-oxide(345 mg).

(2) (5RS,6SR,7SR)-6-Tert-butoxycarbonyl-7-(2-benzyloxy-4-methoxyphenyl)-2-[(N-benzoyl)propylamino]-5-(3,4-methylenedioxyphenyl)cyclopenteno[1,2-b]pyridine (5RS,6SR,7SR)-6-Tert-butoxycarbonyl-7-(2-benzyloxy-4-methoxyphenyl)-5-(3,4-methylenedioxyphenyl)cyclopenteno[1,2-b]pyridine N-oxide(224 mg, 0.395 mmol) and CsF(1.82 g) were dried under reduced pressure. To the mixture were added dichloromethane(4.0 ml) under nitrogen atmosphere and N-propylbenzimidoyl chloride(210 mg) which was prepared from benzoic acid N-propylamide and thionyl chloride. The solution was stirred vigorously under heating at reflux, treated with an aqueous saturated solution of NaHCO$_3$ and water, stirred at room temperature to make the solution homogeneous and extracted with dichloromethane. The organic layer was washed with brine and dried over MgSO$_4$. After removal of the solvent the residue was purified by MPL(E. Merck Kieselgel 60 lobar column/dichloromethane:acetone=100:1 to 50:1 to 30:1) to give (5RS,6SR,7SR)-6-tert-butoxycarbonyl-7-(2-benzyloxy-4-methoxyphenyl)-2-[(N-benzoyl)propylamino]-5-(3,4-methylenedioxyphenyl)cyclopenteno[1,2-b]pyridine(138 mg).

(3) (5RS,6SR,7SR)-6-Tert-butoxycarbonyl-7-[2-(2-benzyloxy-1-methoxycarbonylethoxy)-4-methoxyphenyl]-

2-[(N-benzoyl)propylamino]-5-(3,4-methylenedioxyphenyl)cyclopenteno[1,2-]pyridine Each of diastereomers of (5RS,6SR,7SR)-6-tert-butoxycarbonyl-7-[2-(2-benzyloxy-1-methoxycarbonylethoxy)-4-methoxyphenyl]-2-[(N-benzoyl)propylamino]-5-(3,4-methylenedioxyphenyl)cyclopenteno[1,2-b]pyridine and (5RS,6SR,7SR)-6-tert-butoxycarbonyl-2-[(N-benzoyl)propylamino]-5-(3,4-methylenedioxyphenyl)-7-[2-(1-methoxycarbonylethenyloxy)-4-methoxyphenyl] cyclopenteno[1,2-b]pyridine were prepared in the same manner as in Example 64-(1) using (5RS,6SR,7SR)-6-tert-butoxycarbonyl-7-(2-benzyloxy-4-methoxyphenyl)-2-[(N-benzoyl)propylamino]-5-(3,4-methylenedioxyphenyl)cyclopenteno[1,2-b]pyridine which was prepared in (2).

(4) One of diastereomers of (5RS,6SR,7SR)-6-tert-butoxycarbonyl-7-[2-(2-benzyloxy-1-methoxycarbonylethoxy)-4-methoxyphenyl]-2-[(N-benzoyl)propylamino]-5-(3,4-methylenedioxyphenyl)cyclopenteno[1,2-b]pyridine which was prepared in (3) was subjected to debenzylation using palladium black as a catalyst, de-tert-butylation with TFA, demethylation and debenzoylation with 4N NaOH to give the title compound.
mp: 183°–188° C.

High Resolution FAB-MS(m/e, $(C_{29}H_{30}N_2O_9+H)^+$):
Calcd: 551.2030 Found: 551.2057

$^1$H-NMR(300 MHz, CDCl$_3$, δ ppm): 0.86(3H, t, J=7.3 Hz), 1.54(2H, sext, J=7.3 Hz), 2.99–3.13(2H, m), 3.62(1H, t, J=8.7 Hz), 3.67(3H, s), 3.93–4.07(2H, m), 4.63(1H, d, J=8.7 Hz), 4.83–4.93(1H, m), 5.43(1H, d, J=8.7 Hz), 5.97 (2H, s), 6.36–6.52(2H, m), 6.62–6.72(2H, m), 6.78(1H, d, J=8.4 Hz), 7.08(1H, d, J=8.6 Hz), 7.36(1H, d, J=8.9 Hz), 7.74(1H, brs)

Rf Value: 0.47(E. Merck, Kieselgel 60F$_{254}$/ chloroform:methanol:acetic acid=10:1:1)

EXAMPLE 125

(5RS,6SR,7SR)-6-Carboxy-7-[2-(1-carboxy-2-hydroxyethoxy)-4-methoxyphenyl]-2-propylamino-5-(3,4-methylenedioxyphenyl)cyclopenteno[1,2-b] pyridine(the other diastereomer)

The title compound was prepared in the same manner as in Example 124-(4) using the other diastereomer of (5RS,6SR,7SR)-6-tert-butoxycarbonyl-7-[2-(2-benzyloxy-1-methoxycarbonylethoxy)-4-methoxyphenyl]-2-[(N-benzoyl)propylamino]-5-(3,4-methylenedioxyphenyl)cyclopenteno[1,2-b]pyridine which was prepared in Example 124-(3).
mp: 165°–175° C.

High Resolution FAB-MS(m/e, $(C_{29}H_{30}N_2O_9+H)^+$):
Calcd: 551.2030 Found: 551.2046

$^1$H-NMR(300 MHz, Acetone-d$_6$, δ ppm): 0.90(3H, t, J=7.4 Hz), 1.56(2H, sext, J=7.4 Hz), 3.11–3.21(2H, m), 3.26(1H, t, J=8.2 Hz), 3.76(3H, s), 3.83–4.04(2H, m), 4.47 (1H, d, J=8.2 Hz), 4.91–4.99(1H, m), 5.06(1H, d, J=8.2 Hz), 5.97(2H, s), 6.41(1H, d, J=8.5 Hz), 6.48–6.58(2H, m), 6.80(3H, s), 7.08(1H, d, J=7.9 Hz), 7.10(1H, d, J=7.6 Hz)

Rf Value: 0.27(E. Merck, Kieselgel 60F$_{254}$/ chloroform:methanol:acetic acid=10:1:1)

EXAMPLE 126

(5RS,6SR,7SR)-6-Carboxy-7-[2-(1-carboxyethenyloxy)-4-methoxyphenyl]-2-propylamino-5-(3,4-methylenedioxyphenyl)cyclopenteno[1,2-b]pyridine (5RS,6SR,7SR)-6-tert-butoxycarbonyl-2-[(N-benzoyl) propylamino]-5-(3,4-methylenedioxyphenyl)-7-[2-(1-methoxycarbonylethenyloxy)-4-methoxyphenyl] cyclopenteno[1,2-b]pyridine which was prepared in Example 124-(3) was subjected to de-tert-butylation with TFA, demethylation and debenzoylation with 4N NaOH to give the title compound.
mp: 165°–169° C.

High Resolution FAB-MS(m/e, $(C_{29}H_{28}N_2O_8+H)^+$):
Calcd: 533.1924 Found: 533.1940

$^1$H-NMR(300 MHz, CDCl$_3$, δ ppm): 0.86(3H, t, J=7.4 Hz), 1.55(2H, sext, J=7.4 Hz), 3.03–3.17(2H, m), 3.69(3H, s), 3.70(1H, t, J=8.0 Hz), 4.59(1H, d, J=8.0 Hz), 5.31(1H, brs), 5.34(1H, d, J=8.0 Hz), 5.98(2H, s), 6.06(1H, brs), 6.42–6.52(2H, m), 6.59(1H, d, J=2.2 Hz), 6.69–6.83(3H, m), 7.11(1H, d, J=8.6 Hz), 7.33(1H, d, J=8.9 Hz), 7.63(1H, brs)

Rf Value: 0.35(E. Merck, Kieselgel 60F$_{254}$/ chloroform:methanol:acetic acid=20:1:1)

EXAMPLE 127

(5RS,6SR,7SR)-7-(2-Ethoxycarbonylmethoxy-4-methoxyphenyl)- 6-carboxy-2-(N-propyl-N-methylamino)-5-(3,4-methylenedioxyphenyl) cyclopenteno[1,2-b]pyridine (1) (5RS,6SR,7SR)-6-Tert-butoxycarbonyl-2-propylamino-7-[2-benzyloxy-4-methoxyphenyl]-5-(3,4-methylenedioxyphenyl)cyclopenteno[1,2-b]pyridine To a dioxane solution(3 ml) of (5RS,6SR,7SR)-6-tert-butoxycarbonyl-7-(2-benzyloxy-4-methoxyphenyl)-2-[(N-benzoyl)propylamino]-5-(3,4-methylenedioxyphenyl)cyclopenteno[1,2-b]pyridine(215 mg,0.301 mmol) which was prepared in Example 124-(2) was added 4N NaOH(3 ml) and tetrabutylammonium bromide(97 mg) and the mixture stirred at 110° C. for 22 h. The reaction solution made acid with 3N HCl and extracted with AcOEt. The organic layer was washed with water, a saturated aqueous solution of NaHCO$_3$ and brine and dried over Na$_2$SO$_4$. After removal of the solvent under reduced pressure the residue was purified by dry flash column chromatography(E. Merck Kieselgel 60/hexane:AcOEt=1:1) to give (5RS,6SR,7SR)-6-tert-butoxycarbonyl-2-propylamino-7-(2-benzyloxy-4-methoxyphenyl)-5-(3,4-methylenedioxyphenyl)cyclopenteno[1,2-b]pyridine(167 mg).

(2) (5RS,6SR,7SR)-6-Tert-butoxycarbonyl-2-(N-propyl-N-methylamino-7-(2-benzyloxy-4-methoxyphenyl)-5-(3,4-methylenedioxyphenyl)cyclopenteno[1,2-b]pyridine To a THF solution(3 ml) of (5RS,6SR,7SR)-6-tert-butoxycarbonyl-2-propylamino-7-(2-benzyloxy-4-methoxyphenyl)-5-(3,4-methylenedioxyphenyl) cyclopenteno[1,2-b]pyridine(163 mg,0.267 mmol) which was prepared in (1) was added 1M lithium hexamethyldisilazide-THF solution(290 µl) at −78° C. The mixture was stirred at the same temperature for 10 min and at room temperature for 30 min. The reaction solution was treated with methyl iodide(18 µl) at room temperature, stirred at room temperature for 1 h, cooled at 0° C. and treated with 3N HCl to quench the reaction. The reaction solution was extracted with AcOEt and the organic layer was washed with water, a saturated aqueous solution of NaHCO$_3$ and brine and dried over Na$_2$SO$_4$. After removal of the solvent under reduced pressure the residue was purified by dry flash column chromatography(E. Merck Kieselgel 60/hexane:AcOEt=2:1) to give (5RS,6SR,7SR)-6-Tert-butoxycarbonyl-2-(N-propyl-N-methylamino-7-(2-benzyloxy-4-methoxyphenyl)-5-(3,4-methylenedioxyphenyl)cyclopenteno[1,2-b]pyridine(152 mg).

(3) The title compound was prepared in the same manner as in Example 50-(5),(6),(7) using (5RS,6SR,7SR)-6-tert-butoxycarbonyl-2-(N-propyl-N-methylamino-7-(2-benzyloxy-4-methoxyphenyl)-5-(3,4-methylenedioxyphenyl)cyclopenteno[1,2-b]pyridine which was prepared in (2).

mp: 55°–57° C.

High Resolution FAB-MS(m/e, $(C_{31}H_{34}N_2O_8+H)^+$): Calcd: 563.2393 Found: 563.2417

$^1$H-NMR(300 MHz, CDCl$_3$, δ ppm): 0.82(3H, t, J=7.4 Hz), 1.21(3H, t, J=7.1 Hz), 1.46–1.59(2H, m), 2.95(3H, s), 3.15(1H, t, J=9.2 Hz), 3.15–3.27(1H, m), 3.50–3.59(1H, m), 3.77(3H, s), 4.18(2H, q, J=7.1 Hz), 4.46(1H, d, J=15.9 Hz), 4.53(1H, d, J=9.2 Hz), 4.57(1H, d, J=15.9 Hz), 4.90(1H, d, J=9.2 Hz), 5.91–5.92(2H, m), 6.29(1H, d, J=8.6 Hz), 6.35 (1H, d, J=2.3 Hz), 6.50(1H, dd, J=2.3 Hz, 8.4 Hz), 6.71–6.77 (3H, m), 7.06(1H, d, J=8.6 Hz), 7.11(1H, d, J=8.4 Hz)

Rf Value: 0.66(E. Merck, Kieselgel 60F$_{254}$/ chloroform:methanol=10:1).

EXAMPLE 128

(5RS,6SR,7SR)-6-Carboxy-7-(2-carboxymethoxy-4-methoxyphenyl)-2-(N-propyl-N-methylamino)-5-(3,4-methylenedioxyphenyl)cyclopenteno[1,2-b]pyridine The title compound was prepared in the same manner as in Example 2 using (5RS,6SR,7SR)-7-(2-ethoxycarbonylmethoxy-4-methoxyphenyl)-6-carboxy-2-(N-propyl-N-methylamino)-5-(3,4-methylenedioxyphenyl)cyclopenteno[1,2-b]pyridine which was prepared in Example 127.

mp: 120°–123° C.

High Resolution FAB-MS(m/e, $(C_{29}H_{30}N_2O_8+H)^+$): Calcd: 535.2080 Found: 535.2110

$^1$H-NMR(300 MHz, CDCl$_3$, δ ppm): 0.83(3H, t, J=7.4 Hz), 1.49– 1.61(2H, m), 2.92(1H, t, J=9.0 Hz), 2.99(3H, s), 3.19–3.29(1H, m), 3.50–3.60(1H, m), 3.77(3H, s), 4.45–4.60(3H, m), 5.17(1H, d, J=9.0 Hz), 5.90–5.91(2H, m), 6.35–6.37(2H, m), 6.47(1H, d, J=2.3 Hz), 6.66(1H, s), 6.68–6.74(2H, m), 7.05(1H, d, J=8.6 Hz), 7.11(1H, d, J=8.6 Hz)

Rf Value: 0.30(E. Merck, Kieselgel 60F$_{254}$/ chloroform:methanol:acetic acid=10:1:1)

Each compound in the following Examples 129 and 130 was prepared in the same manner as in Examples 127 and 128.

EXAMPLE 129

(5RS,6SR,7SR)-6-Carboxy-7-(2-carboxymethoxy-4-methoxyphenyl)-2-methylamino)-5-(3,4-methylenedioxyphenyl)cyclopenteno[1,2-b]pyridine mp: 194°–196° C.

High Resolution FAB-MS(m/e, $(C_{26}H_{24}N_2O_8+H)^+$): Calcd: 493.1611 Found: 493.1622

$^1$H-NMR(300 MHz, DMSO-d$_6$, δ ppm): 2.62(3H, d, J=4.8 Hz), 3.04(1H, t, J=8.8 Hz), 3.71(3H, s), 4.30(1H, d, J=8.5 Hz), 4.36(1H, d, J=16.4 Hz), 4.56(1H, d, J=16.4 Hz), 4.61(1H, d, J=8.5 Hz), 5.96(2H, s), 6.21(1H, d, J=8.3 Hz), 6.34(1H, d, J=4.8 Hz), 6.46–6.49(2H, m), 6.68(1H, d, J=8.2 Hz), 6.71(1H, s), 6.82(1H, d, J=7.6 Hz), 6.90–6.96(2H, m)

Rf Value: 0.46(E. Merck, Kieselgel 60F$_{254}$/ chloroform:methanol:acetic acid=10:1:1)

EXAMPLE 130

(5RS,6SR,7SR)-6-Carboxy-7-(2-carboxymethoxy-4-methoxyphenyl)-2-(N,N-dimethylamino)-5-(3,4-methylenedioxyphenyl)cyclopenteno[1,2-b]pyridine mp: 153°–156° C.

High Resolution FAB-MS(m/e, $(C_{27}H_{26}N_2O_8+H)^+$): Calcd: 507.1767 Found: 507.1759

$^1$H-NMR(300 MHz, CD$_3$OD, δ ppm): 3.03(6H, s), 3.19–3.25(1H, m), 3.76(3H, s), 4.38–4.55(3H, m), 4.86(1H, m), 5.89(2H, s), 6.47(1H, d, J=2.1 Hz), 6.53(1H, dd, J=2.1 Hz, 8.5 Hz), 6.61(1H, d, J=8.9 Hz), 6.72(1H, s), 6.75(2H, s), 7.03(1H, d, J=8.5 Hz), 7.19(1H, d, J=8.9 Hz)

Rf Value: 0.57(E. Merck, Kieselgel 60F$_{254}$/ chloroform:methanol:acetic acid=5:1:1)

EXAMPLE 131

(5RS,6SR,7SR)-6-Carboxy-7-(2-carboxymethoxy-5-tert-butyl-4-methoxyphenyl)-2-methylamino-5-(3,4-methylenedioxyphenyl)cyclopenteno[1,2-b]pyridine To a tert-butyl acetate solution(10 ml) of (5RS,6SR,7SR)-6-carboxy-7-(2-carboxymethoxy-4-methoxyphenyl)-2-methylamino-5-(3,4-methylenedioxyphenyl)cyclopenteno[1,2-b]pyridine(64.1 mg,0.13 mmol) which was prepared in Example 129 was added 70% perchloric acid to make acid(pH1–2), and the mixture was stirred at room temperature for 66 h, neutralized with a saturated aqueous solution of NaHCO$_3$ and extracted with AcOEt and dried over Na$_2$SO$_4$. After removal of the solvent under reduced pressure the residue was purified by preparative TLC(E. Merck Kieselgel 60/chloroform:methanol=10:1) to give mono tert-butyl esters of 7-(2-carboxymethoxy-5-tert-butyl-4-methoxyphenyl) compounds(yields: 49 mg,10 mg), followed by removing the tert-butyl ester with TFA to give the title compound.

mp: 190°–192° C.

High Resolution FAB-MS(m/e, $(C_{30}H_{32}N_2O_8+H)^+$): Calcd: 549.2237 Found: 549.2253

$^1$H-NMR(400 MHz, CD$_3$OD, δ ppm): 1.27(9H, s), 2.95 (3H, s), 3.57(1H, t, J=8.4 Hz), 3.84(3H, s), 4.59(1H, d, J=8.4 Hz), 4.64(1H, d, J=16.4 Hz), 4.80(1H, d, J=16.4 Hz), 5.17(1H, d, J=8.4 Hz), 5.95(2H, s), 6.62(1H, s), 6.75–6.84 (4H, m), 7.09(1H, s), 7.55 (1H, d, J=8.8 Hz)

Rf Value: 0.55(E. Merck, Kieselgel 60F$_{254}$/ chloroform:methanol:acetic acid=10:1:1)

EXAMPLE 132

(5RS,6SR,7SR)-2-Amino-6-carboxy-7-(2-carboxymethoxy-4--methoxyphenyl)-5-(3,4-methylenedioxyphenyl)cyclopenteno[1,2-b]pyridine (1) (5RS,6SR,7SR)-6-Tert-butoxycarbonyl-7-(2-tert-butoxycarbonylmethoxy-4-methoxyphenyl)-5-(3,4-methylenedioxyphenyl)cyclopenteno[1,2-b]pyridine N-oxide (5RS,6SR,7SR)-6-Tert-butoxycarbonyl-7-(2-tert-butoxycarbonylmethoxy-4-methoxyphenyl)-5-(3,4-methylenedioxyphenyl)cyclopenteno[1,2-b]pyridine N-oxide was prepared in the same manner as in Example 124-(1) using (5RS,6SR,7SR)-6-tert-butoxycarbonyl-7-(2-tert-butoxycarbonylmethoxy-4-methoxyphenyl)-5-(3,4-methylenedioxyphenyl)cyclopenteno[1,2-b]pyridine which was prepared in the same manner as in Example 50-(6) using tert-butyl bromoacetate.

(2) (5RS,6SR,7SR)-6-Tert-butoxycarbonyl-7-(2-tert-butoxycarbonylmethoxy-4-methoxyphenyl-2-[N-(benzoyl)benzylamino]-5-(3,4-methylenedioxyphenyl)cyclopenteno[1,2-b]pyridine (5RS,6SR,7SR)-6-Tert-butoxycarbonyl-7-(2-tert-butoxycarbonylmethoxy-4-methoxyphenyl)-5-(3,4-methylenedioxyphenyl)cyclopenteno[1,2-b]pyridine N-oxide which was prepared in (1) was reacted with N-benzylbenzimidoyl chloride which was prepared from N-benzylbenzamide in the same manner as in Example 124-(2) to give (5RS,6SR,7SR)-6-tert-butoxycarbonyl-7-(2-tert-butoxycarbonylmethoxy-4-methoxyphenyl)-2-[(N-benzoyl)benzylamino]-5-(3,4-methylenedioxyphenyl)cyclopenteno[1,2-b]pyridine.

(3) (5RS,6SR,7SR)-6-tert-butoxycarbonyl-7-(2-tert-butoxycarbonylmethoxy-4-methoxyphenyl-2-(benzoylamino)-5-(3,4-methylenedioxyphenyl)cyclopenteno[1,2-b]pyridine (5RS,6SR,7SR)-6-Tert-butoxycarbonyl-7-(2-tert-butoxycarbonylmethoxy-4-methoxyphenyl)-2-[(N-benzoyl)benzylamino]-5-(3,4-methylenedioxyphenyl)cyclopenteno[1,2-b]pyridine which was prepared in (2) was subjected to hydrogenation under hydrogen atmosphere at 50 to 60 psi using palladium black as a catalyst to give (5RS,6SR,7SR)-6-tert-butoxycarbonyl-7-(2-tert-butoxycarbonylmethoxy-4-methoxyphenyl)-2-(benzoylamino)-5-(3,4-methylenedioxyphenyl)cyclopenteno[1,2-b]pyridine.

(4) (5RS,6SR,7SR)-6-tert-butoxycarbonyl-7-(2-tert-butoxycarbonylmethoxy-4-methoxyphenyl)-2-(benzoylamino)-5-(3,4-methylenedioxyphenyl)cyclopenteno[1,2-b]pyridine was subjected to the same reaction as in Example 124-(4) to give the title compound.

mp: 204°–206° C.

High Resolution FAB-MS(m/e, $(C_{25}H_{22}N_2O_8+H)^+$): Calcd: 479.1454 Found: 479.1458

$^1$H-NMR(300 MHz, CD$_3$OD, δ ppm): 3.70(1H, t, J=9.2 Hz), 3.77(3H, s), 4.55(1H, d, J=9.2 Hz), 4.61(1H, d, J=16.2 Hz), 4.78(1H, d, J=16.2 Hz), 5.22(1H, d, J=9.2 Hz), 5.95 (2H, s), 6.54(1H, dd, J=2.2 Hz, 8.4 Hz), 6.58(1H, d, J=2.2 Hz), 6.72–6.78(3H, m), 6.83(1H, d, J=8.4 Hz), 7.23(1H, d, J=8.3 Hz), 7.40(1H, d, J=8.9 Hz)

Rf Value: 0.48(E. Merck, Kieselgel 60F$_{254}$/chloroform:methanol:acetic acid=10:1:1)

Each compound in the following Examples 133 to 135 was prepared in the same manner as in Example 132 using N-(3-benzyloxypropyl)- or N-(2-benzyloxyethyl)-bezimidoyl chloride.

EXAMPLE 133

(5RS,6SR,7SR)-6-Carboxy-7-(2-carboxymethoxy-4-methoxyphenyl)-2-[(N-benzoyl)-3-hydroxypropylamino]-5-(3,4-methylenedioxyphenyl)cyclopenteno[1,2-b]pyridine mp: 127°–132° C.

High Resolution FAB-MS(m/e, $(C_{35}H_{32}N_2O_{10}+H)^+$): Calcd: 641.2135 Found: 641.2131

$^1$H-NMR(300 MHz, CD$_3$OD, δ ppm): 1.71–1.89(2H, m), 3.52(1H, t, J=9.6 Hz), 3.52–3.58(2H, m), 3.79(3H, s), 4.00 (2H, t, J=6.9 Hz), 4.42(1H, d, J=16.2 Hz), 4.48(1H, d, J=9.6 Hz), 4.58(1H, d, J=16.2 Hz), 4.77(1H, d, J=9.6 Hz), 5.89 (2H, s), 6.46(1H, d, J=2.3 Hz), 6.53(1H, dd, J=2.3 Hz, 8.4 Hz), 6.68(1H, d, J=7.9 Hz), 6.71–6.75(3H, m), 7.00(1H, d, J=8.4 Hz), 7.06(1H, dd, J=1.4 Hz, 7.9 Hz), 7.22–7.37(5H, m)

Rf Value: 0.39(E. Merck, Kieselgel 60F$_{254}$/chloroform:methanol:acetic acid=30:1:1)

EXAMPLE 134

(5RS,6SR,7SR)-6-Carboxy-7-(2-carboxymethoxy-4-methoxyphenyl)-2-(3-hydroxypropylamino)-5-(3,4-methylenedioxyphenyl)cyclopenteno[1,2-b]pyridine mp: 166°–169° C.

High Resolution FAB-MS(m/e, $(C_{28}H_{28}N_2O_9+H)^+$): Calcd: 537.1873 Found: 537.1864

$^1$H-NMR(300 MHz, CD$_3$OD, δ ppm): 1.81(2H, quint, J=6.3 Hz), 3.39(2H, t, J=6.3 Hz), 3.60–3.70(3H, m), 3.78 (3H, s), 4.56(1H, d, J=9.2 Hz), 4.61(1H, d, J=13.8 Hz), 4.76(1H, d, J=13.8 Hz), 5.20(1H, d, J=10.0 Hz), 5.96(2H, s), 6.53–6.57(2H, m), 6.78–6.86(4H, m), 7.22(1H, d, J=8.5 Hz), 7.47(1H, d, J=8.9 Hz)

Rf Value: 0.33(E. Merck, Kieselgel 60F$_{254}$/chloroform:methanol:acetic acid=30:1:1)

EXAMPLE 135

(5RS,6SR,7SR)-6-Carboxy-7-(2-carboxymethoxy-4-methoxyphenyl)-2-(2-hydroxypropylamino)-5-(3,4-methylenedioxyphenyl)cyclopenteno[1,2-b]pyridine mp: 200° C. (dec.)

High Resolution FAB-MS(m/e, $(C_{27}H_{26}N_2O_9+H)^+$): Calcd: 523.1717 Found: 523.1687

$^1$H-NMR(300 MHz, CD$_3$OD, δ ppm): 3.35(2H, t, J=5.2 Hz), 3.43(1H, t, J=9.6 Hz), 3.67(2H, t, J=5.2 Hz), 3.75(3H, s), 4.48(1H, d, J=9.6 Hz), 4.49(1H, d, J=15.8 Hz), 4.61(1H, d, J=15.8 Hz), 5.09(1H, d, J=9.6 Hz), 5.91(2H, s), 6.51(1H, dd, J=2.4 Hz, 8.3 Hz), 6.53(1H, d, J=2.4 Hz), 6.67(1H, d, J=8.6 Hz), 6.74–6.77(3H, m), 7.19(1H, d, J=8.3 Hz), 7.31 (1H, d, J=8.6 Hz)

Rf Value: 0.53(E. Merck, Kieselgel 60F$_{254}$/chloroform:methanol=3:1)

Each compound in the following Examples 136 to 144 was prepared in the same manner as in Example 89 using corresponding aryl Grignard reagent or aryl lithium reagent.

EXAMPLE 136

(5RS,6SR,7SR)-6-Carboxy-5-(3,5-dimethoxyphenyl)-7-(4-methoxyphenyl)cyclopenteno[1,2-b]pyridine mp: 212°–214° C.

High Resolution FAB-MS(m/e, $(C_{24}H_{23}NO_5+H)^+$): Calcd: 406.1654 Found: 406.1658

$^1$H-NMR(300 MHz, CDCl$_3$, δ ppm): 3.35(1H, t, J=9.5 Hz), 3.76(3H, s), 3.77(6H, s), 4.61(1H, d, J=9.5 Hz), 4.70 (1H, d, J=9.5Hz), 6.40(3H, s), 6.87(2H, d, J=8.7 Hz), 7.14(1H, dd, J=4.9 Hz, 7.7 Hz), 7.16(2H, d, J=8.7 Hz), 7.35(1H, td, J=1.4 Hz, 7.7 Hz), 8.47(1H, td, J=1.4 Hz, 4.9 Hz)

Rf Value: 0.33(E. Merck, Kieselgel 60F$_{254}$/chloroform:methanol=15:1)

EXAMPLE 137

(5RS,6SR,7SR)-6-Carboxy-5-(3-propoxy-5-methoxyphenyl)-7-(4-methoxyphenyl)cyclopenteno[1,2-b]pyridine mp: 205°–206° C.

High Resolution FAB-MS(m/e, $(C_{26}H_{27}NO_5+H)^+$): Calcd: 434.1968 Found: 434.1953

¹H-NMR(300 MHz, CDCl₃, δ ppm): 1.02(3H, t, J=7.2 Hz), 1.79(2H, sixt, J=7.2 Hz), 3.37(1H, t, J=9.7 Hz), 3.77 (3H, s), 3.78(3H, s), 3.87(2H, t, J=7.2 Hz), 4.61(1H, d, J=9.7 Hz), 4.70(1H, d, J=9.7 Hz), 6.40(3H, s), 6.88(2H, d, J=8.4 Hz), 7.13(1H, dd, J=4.9 Hz, 7.7 Hz), 7.18(2H, d, J=8.4 Hz), 7.35(1H, d, J=7.7 Hz), 8.47(1H, d, J=4.9 Hz)

Rf Value: 0.42(E. Merck, Kieselgel 60F₂₅₄/chloroform:methanol=10:1)

EXAMPLE 138

(5RS,6SR,7SR)-6-Carboxy-5-(3,4-methylenedioxy-5-methoxyphenyl)-7-(4-methoxyphenyl)cyclopenteno[1,2-b]pyridine mp: 220° C. (dec.)

High Resolution FAB-MS(m/e, (C₂₄H₂₁NO₆+H)⁺): Calcd: 420.1447 Found: 420.1466

¹H-NMR(300 MHz, CDCl₃, δ ppm): 3.32(1H, t, J=9.6 Hz), 3.80(3H, s), 3.89(3H, s), 4.60(1H, d, J=9.6 Hz), 4.69 (1H, d, J=9.6 Hz), 5.98(2H, s), 6.42(1H, d, J=1.1 Hz), 6.46(1H, d, J=1.1 Hz), 6.90(2H, d, J=8.6 Hz), 7.14(1H, dd, J=4.5 Hz, 7.4 Hz), 7.19(2H, d, J=8.6 Hz), 7.33(1H, d, J=7.4 Hz), 8.48(1H, d, J=4.5 Hz)

Rf Value: 0.47(E. Merck, Kieselgel 60F₂₅₄/chloroform:methanol=10:1)

EXAMPLE 139

(5RS,6SR,7SR)-6-Carboxy-5-(3-benzyloxy-4-methoxyphenyl)-7-(4-methoxyphenyl)cyclopenteno[1,2-b]pyridine mp: 79°–80° C.

High Resolution FAB-MS(m/e, (C₃₀H₂₇NO₅+H)⁺): Calcd: 482.1967 Found: 482.1989

¹H-NMR(300 MHz, CDCl₃, δ ppm): 3.22(1H, t, J=9.3 Hz), 3.75(3H, s), 3.89(3H, s), 4.55(1H, d, J=9.3 Hz), 4.71 (1H, d, J=9.3 Hz), 5.07(1H, d, J=13.1 Hz), 5.12(1H, d, J=13.1 Hz), 6.68(1H, d, J=1.9 Hz), 6.77–6.88(2H, m), 7.10(2H, d, J=8.6 Hz), 7.12–7.37(9H, m), 8.47(1H, d, J=4.8 Hz)

Rf Value: 0.21(E. Merck, Kieselgel 60F₂₅₄/chloroform:methanol=20:1)

EXAMPLE 140

(5RS,6SR,7SR)-6-Carboxy-5-(3-hydroxy-4-methoxyphenyl)-7-(4-methoxypheny)cyclopenteno[1,2-b]pyridine mp: 127°–129° C.

High Resolution FAB-MS(m/e, (C₂₃H₂₁NO₅+H)⁺): Calcd: 392.1498 Found: 392.1520

¹H-NMR(300 MHz, CDCl₃, δ ppm): 3.31(1H, t, J=9.8 Hz), 3.77(3H, s), 3.89(3H, s), 4.57(1H, d, J=9.8 Hz), 4.70 (1H, d, J=9.8 Hz), 6.77(1H, dd, J=2.0 Hz, 8.1 Hz), 6.80(1H, d, J=2.0 Hz), 6.84(1H, d, J=8.1 Hz), 6.87(2H, d, J=8.8 Hz), 7.12(1H, dd, J=4.9 Hz, 7.0 Hz), 7.16(2H, d, J=8.8 Hz), 7.30(1H, td, J=1.3 Hz, 7.0 Hz), 8.45(1H, td, J=1.3 Hz, 4.9 Hz)

Rf Value: 0.30(E. Merck, Kieselgel 60F₂₅₄/chloroform:methanol=10:1)

EXAMPLE 141

(5RS,6SR,7SR)-5-(4-Indolyl)-6-carboxy-7-(4-methoxyphenyl)cyclopenteno[1,2-b]pyridine mp: 144°–148° C.

High Resolution FAB-MS(m/e, (C₂₄H₂₀N₂O₃+H)⁺): Calcd: 385.1552 Found: 385.1540

¹H-NMR(300 MHz, CD₃OD, δ ppm): 3.51(1H, t, J=10.1 Hz), 3.79(3H, s), 4.75(1H, d, J=10.1 Hz), 5.04(1H, d, J=10.1 Hz), 6.12–6.18(1H, m), 6.90–6.96(3H, m), 7.10(1H, dd, J=7.3 Hz, 8.1 Hz), 7.16–7.25(4H, m), 7.30–7.34(1H, m), 7.36(1H, dd, J=1.0 Hz, 8.1 Hz), 8.32–8.36(1H, m)

Rf Value: 0.42(E. Merck, Kieselgel 60F₂₅₄/chloroform:methanol=10:1)

EXAMPLE 142

(5RS,6SR,7SR)-5-(6-Indolyl)-6-carboxy-7-(4-methoxyphenyl)cyclopenteno[1,2-b]pyridine mp: 128°–134° C.

High Resolution FAB-MS(m/e, (C₂₄H₂₀N₂O₃+H)⁺): Calcd: 385.1552 Found: 385.1570

¹H-NMR(300 MHz, CD₃OD, δ ppm): 3.27–3.35(1H, m), 3.79(3H, s), 4.69(1H, d, J=9.8 Hz), 4.73(1H, d, J=9.6 Hz), 6.43(1H, dd, J=0.9 Hz, 3.2 Hz), 6.90(1H, dd, J=1.6 Hz, 8.1 Hz), 6.85–6.96(2H, m), 7.15–7.21(2H, m), 7.22–7.28(1H, m), 7.22(1H, d, J=3.2 Hz), 7.37–7.43(1H, m), 7.55(1H, d, J=8.1 Hz), 8.30–8.34(1H, m)

Rf Value: 0.29(E. Merck, Kieselgel 60F₂₅₄/chloroform:methanol=10:1)

EXAMPLE 143

(5RS,6SR,7SR)-7-(5-Indolyl)-6-carboxy-5-(3,4-methylenedioxyphenyl)cyclopenteno[1,2-b]pyridine mp: –250° C. (dec.)

High Resolution FAB-MS(m/e, (C₂₄H₁₈N₂O₄+H)⁺): Calcd: 399.1345 Found: 399.1330

¹H-NMR(300 MHz, methanol-d₄, δ ppm): 3.26(1H, t, J=9.9 Hz), 4.60(1H, d, J=9.9 Hz), 4.77(1H, d, J=9.9 Hz), 5.94(2H, s), 6.40(1H, dd, J=0.85 Hz, 3.1 Hz), 6.75(1H, brs), 6.79(1H, d, J=7.9 Hz), 6.83(1H, dd, J=0.8 Hz, 7.9 Hz), 6.92(1H, dd, J=1.7 Hz, 8.4 Hz), 7.21(1H, d, J=3.1 Hz), 7.27(1H, dd, J=4.9 Hz, 7.6 Hz), 7.36(1H, d, J=8.4 Hz), 7.42(1H, td, J=1.4 Hz, 7.6 Hz), 7.43(1H, brs), 8.30(1H, td, J=1.4 Hz, 4.9 Hz)

Rf Value: 0.42(E. Merck, Kieselgel 60F₂₅₄/chloroform:methanol=10:1)

EXAMPLE 144

(5RS,6SR,7SR)-7-(4-Ethoxyphenyl)-6-carboxy-5-(3,4-methylenedioxyphenyl)cyclopenteno[1,2-b]pyridine mp: 215°–217° C.

High Resolution FAB -MS(m/e, (C₂₄H₂₁NO₅+H)⁺): Calcd: 404.1497 Found: 404.1519

¹H-NMR(300 MHz, CDCl₃, δ ppm): 1.39(3H, t, J=7.0 Hz), 3.30(1H, t, J=10.0 Hz), 4.00(2H, q, J=7.0 Hz), 4.60(1H, d, J=10.0 Hz), 4.69(1H, d, J=10.0 Hz), 5.96(1H, d, J=1.4 Hz), 5.97(1H, d, J=1.4 Hz), 6.71(1H, d, J=1.2 Hz), 6.76(1H, dd, J=1.2 Hz, 8.2 Hz), 6.81(1H, d, J=8.2 Hz), 6.88(2H, d, J=8.8 Hz), 7.11–7.13(1H, m), 7.16(2H, d, J=8.8 Hz), 7.31 (1H, d, J=7.6 Hz), 8.48(1H, d, J=5.0 Hz)

Rf Value: 0.80(E. Merck, Kieselgel 60F₂₅₄/chloroform:methanol=10:1)

EXAMPLE 145

(5RS,6SR,7SR)-7-[2-(4-imidazolylmethoxy)-4-methoxyphenyl)-6-carboxy-5-(3,4-methylenedioxyphenyl)cyclopenteno[1,2-b]pyridine The ⁱᵐN-trityl-tert-butyl ester of (5RS,6SR,7SR)-7-[2-hydroxy-4-methoxyphenyl)-6-tert-butoxycarbonyl-5-(3,4- methylenedioxyphenyl)cyclopenteno[1,2-b]pyridine was prepared in the same manner as in Example 50-(6) using (5RS,6SR,7SR)-7-[2-hydroxy-4-methoxyphenyl]-6-tert-butoxycarbonyl-5-(3,4-methylenedioxyphenyl)cyclopenteno[1,2-b]pyridine which was prepared in Example 50-(5) and 4-chloromethyl-1-tritylimidazole. The $^{im}$N-trityl-tert-butyl ester was treated with 4N HCl-dioxane to give the di-HCl salt of the title compound.

mp: 172°–175° C.

High Resolution FAB -MS(m/e, $(C_{27}H_{23}N_3O_6+H)^+$): Calcd: 486.1665 Found: 486.1678

$^1$H-NMR(300 MHz, CD$_3$OD, δ ppm): 3.59(1H, t, J=10.3 Hz), 3.86(3H, s), 4.70(1H, d, J=10.3 Hz), 4.98(1H, d, J=11.9 Hz), 5.14(1H, d, J=10.3 Hz), 5.23(1H, d, J=11.9 Hz), 5.98–6.03(2H, m), 6.18(1H, brs), 6.65(1H, dd, J=1.6 Hz, 7.9 Hz), 6.73(1H, dd, J=2.3 Hz, 8.4 Hz), 6.84(1H, d, J=7.9 Hz), 6.85(1H, d, J=2.3 Hz), 7.35(1H, d, J=8.4 Hz), 7.50(1H, brs), 7.80(1H, dd, J=5.7 Hz, 7.6 Hz), 7.88(1H, d, J=7.6 Hz), 8.55(1H, d, J=5.7 Hz), 8.96(1H, brs)

Each compound in the following Examples 146 and 147 was prepared in the same manners as in Examples 55 and 56 using α-bromo-γ-butylolactone.

EXAMPLE 146

(5RS,6SR,7SR)-7-[2-(2-Oxo-4,5-dihydrofuryloxy)-4-methoxyphenyl]-6-carboxy-5-(3,4-methylenedioxyphenyl)cyclopenteno[1,2-b]pyridine
(one of diastereomers)

mp: 172°–175° C.

High Resolution FAB-MS(m/e, $(C_{27}H_{23}NO_8+H)^+$): Calcd: 490.1502 Found: 490.1499

$^1$H-NMR(300 MHz,Acetone-d$_6$, 67 ppm): 1.80–1.96(1H, m), 2.48–2.60(1H, m), 3.61(1H, t, J=10.2 Hz), 3.80(3H, s), 4.18–4.30(2H, m), 4.63(1H, d, J=10.2 Hz), 4.87(1H, d, J=10.2 Hz), 5.19(1H, t, J=8.3 Hz), 6.00(2H, s), 6.60(1H, dd, J=2.4 Hz, 8.4 Hz), 6.83(1H, d, J=8.0 Hz), 6.84(1H, d, J=2.4 Hz), 6.90(1H, dd, J=1.7 Hz, 8.0 Hz), 6.93(1H, d, J=1.7 Hz), 7.20(1H, d, J=8.4 Hz), 7.33(1H, dd, J=5.0 Hz, 7.6 Hz), 7.43(1H, td, J=1.4 Hz, 7.6 Hz), 8.42(1H, td, J=1.4 Hz, 5.0 Hz)

Rf Value: 0.34(E. Merck, Kieselgel 60F$_{254}$/chloroform:methanol=10:1)

EXAMPLE 147

(5RS,6SR,7SR)-7-[2-(2-Oxo-4,5-dihydrofuryloxy)-4-methoxyphenyl]-6-carboxy-5-(3,4-methylenedioxyphenyl)cyclopenteno[1,2-b]pyridine
(the other diastereomer)

mp: 170°–173° C.

High Resolution FAB-MS(m/e, $(C_{27}H_{23}NO_8+H)^+$): Calcd: 490.1502 Found: 490.1500

$^1$H-NMR(300 MHz, Acetone-d$_6$, δ ppm): 2.24–2.39(1H, m), 2.81–2.92(1H, m), 3.50(1H, t, J=10.2 Hz), 3.79(3H, s), 4.29–4.42(2H, m), 4.67(1H, d, J=10.2 Hz), 5.01(1H, d, J=10.2 Hz), 5.21(1H, t, J=7.9 Hz), 6.01(2H, s), 6.57(1H, dd, J=2.4 Hz, 8.4 Hz), 6.79– 6.87(4H, m), 7.18(1H, d, J=8.4 Hz), 7.39(1H, dd, J=5.2 Hz, 7.7 Hz), 7.54(1H, td, J=1.3 Hz, 7.7 Hz), 8.43(1H, td, J=1.3 Hz, 5.2 Hz)

Rf Value: 0.36(E. Merck, Kieselgel 60F$_{254}$/chloroform:methanol=10:1)

Each compound in the following Examples 148 and 149 was prepared by hydrolyzing the corresponding compounds of Examples 146 and 147 with base.

EXAMPLE 148

(5RS,6SR,7SR)-6-Carboxy-7-[2-(1-carboxy-3-hydroxypropoxy)-4-methoxyphenyl]-5-(3,4-methylenedioxyphenyl)cyclopenteno[1,2-b]pyridine
(one of diastereomers)

High Resolution FAB-MS(m/e, $(C_{27}H_{25}NO_9+H)^+$): Calcd: 508.1608 Found: 508.1613

Rf Value: 0.26(E. Merck, Kieselgel 60F$_{254}$/chloroform:methanol:acetic acid=10:1:1)

EXAMPLE 149

(5RS,6SR,7SR)-6-Carboxy-7-[2-(1-carboxy-3-hydroxypropoxy)-4-methoxyphenyl]-5-(3,4-methylenedioxyphenyl)cyclopenteno[1,2-b]pyridine
(the other diastereomer)

High Resolution FAB-MS(m/e, $(C_{27}H_{25}NO_9+H)^+$): Calcd: 508.1608 Found: 508.1602

Rf Value: 0.25(E. Merck, Kieselgel 60F$_{254}$/chloroform:methanol:acetic acid=10:1:1)

EXAMPLE 150

(5RS,6SR,7SR)-7-(2-Acetoxymethylcarbonylmethoxy-4-methoxyphenyl-6-carboxy-5-(3,4-methylenedioxyphenyl)cyclopenteno[1,2-b]pyridine (1) (5RS,6SR,7SR)-7-(2-Diazomethylcarbonylmethoxy-4-methoxyphenyl)-6-tert-butoxycarbonyl-5-(3,4-methylenedioxyphenyl)cyclopenteno[1,2-b]pyridine To a DMF suspension (2 ml) of CsCO$_3$(79.50 mg) and (5RS,6SR,7SR)-7-(2-hydroxy-4-methoxyphenyl)-6-tert-butoxycarbonyl-5-(3,4-methylenedioxyphenyl)cyclopenteno[1,2-b]pyridine(98.0 mg,0.212 mmol) which was prepared in Example 50-(5) was added a DMF(1 ml) solution of diazomethylbromomethylketone(43 mg) which was prepared by the method described in the literature [Biochemistry, 16, 1964–1970(1977)] at 0° C. The mixture was stirred at 0° C. to room temperature for 12 h, treated with 10% citric acid and extracted with AcOEt. The organic layer was washed brine, dried over Na$_2$SO$_4$ and concentrated under reduced pressure. The residue was purified by preparative TLC(E. Merck Kieselgel 60F$_{254}$/hexane:AcOEt=2:3) to give (5RS,6SR,7SR)-7-(2-diazomethylcarbonylmethoxy-4-methoxyphenyl)-6-tert-butoxycarbonyl-5-(3,4-methylenedioxyphenyl)cyclopenteno[1,2-b]pyridine(64.4 mg).

(2) An AcOH suspension(2.5 ml) of (5RS,6SR,7SR)-7-(2-diazomethylcarbonylmethoxy-4-methoxyphenyl)-6-tert-butoxycarbonyl- 5-(3,4-methylenedioxyphenyl)cyclopenteno[1,2-b]pyridine(13.5 mg,0.0249 mmol) which was prepared in (1) was heated at 110° C. for 30 min with stirring. The reaction solution was concentrated under reduced pressure and the residue was purified by preparative TLC(E. Merck Kieselgel 60F$_{254}$/hexane:AcOEt=1:2) to give (5RS,6SR,7SR)-7-(2-acetoxymethylcarbonylmethoxy-4-methoxyphenyl)-6-tert-butoxycarbonyl-5-(3,4-methylenedioxyphenyl)cyclopenteno[1,2-b]pyridine(8.6 mg). The title compound was prepared by treating the ester with 4N HCl-dioxane.

mp: 80°–84° C.

High Resolution FAB-MS(m/e, $(C_{28}H_{25}NO_9+H)^+$): Calcd: 520.1608 Found: 520.1640

$^1$H-NMR(300 MHz, Acetone-d$_6$, δ ppm): 2.08(3H, s), 3.46(1H, t, J=10.1 Hz), 3.79(3H, s), 4.64(1H, d, J=10.1 Hz), 4.65(1H, d, J=16.6 Hz), 4.80(1H, d, J=16.6 Hz), 4.84(2H, s), 4.97(1H, d, J=10.1 Hz), 5.99(1H, d, J=1.5 Hz), 6.00(1H, d, J=1.5 Hz), 6.56–6.59(2H, m), 6.81–6.87(3H, m), 7.14(1H, d, J=8.8 Hz), 7.17(1H, dd, J=4.9 Hz, 7.6 Hz), 7.30(1H, td, J=1.3 Hz, 7.6 Hz), 8.35(1H, td, J=1.3 Hz, 4.9 Hz)

Rf Value: 0.55(E. Merck, Kieselgel 60F$_{254}$/chloroform:methanol=10:1)

Each compound in the following Examples 151 and 152 was prepared in the same manner as in Example 83.

EXAMPLE 151

(5RS,6SR,7SR)-2-Isopropylamino-6-carboxy-5-(3,4-methylenedioxyphenyl)-7-(4-methoxyphenyl) cyclopenteno[1,2-b]pyridine mp: 100°–101° C.

High Resolution FAB-MS(m/e, (C$_{26}$H$_{26}$N$_{2}$O$_{5}$+H)$^{+}$): Calcd: 447.1919 Found: 447.1927

$^1$H-NMR(300 MHz, CDCl$_3$, δ ppm): 1.17(3H, d, J=6.3 Hz), 1.20(3H, d, J=6.3 Hz), 3.03(1H, t, J=8.6 Hz), 3.64(1H, sept, J=6.3 Hz), 3.70(3H, s), 4.40(1H, d, J=8.6 Hz), 4.59(1H, d, J=8.6 Hz), 4.62(1H, brs), 5.93(2H, ABq, J=1.4 Hz, Δv=2.3 Hz), 6.28(1H, d, J=8.4 Hz), 6.717(1H, d, J=6.1 Hz), 6.723(1H, d, J=6.1 Hz), 6.74(1H, s), 6.82(2H, d, J=8.6 Hz), 7.14(1H, d, J=8.4 Hz), 7.17(2H, d, J=8.6 Hz)

Rf Value: 0.30(E. Merck, Kieselgel 60F$_{254}$/chloroform:methanol=20:1)

EXAMPLE 152

6-Carboxy-5-(3,4-methylenedioxyphenyl)-7-(4-methoxyphenyl)cyclopent-[-1,2-dieno-[1,2-b] pyridine and 6-Carboxy-5-(3,4-methylenedioxyphenyl)-7-(4-methoxyphenyl) cyclopent-1,2-dieno[2,1-b]pyridine(1:2 mixture)

High Resolution FAB-MS(m/e, (C$_{26}$H$_{24}$N$_{2}$O$_{5}$+H)$^{+}$): Calcd: 445.1763 Found: 445.1746

$^1$H-NMR(300 MHz, CDCl$_3$, δ ppm): 1.17(3H, d, J=6.5 Hz), 1.19(3H, d, J=6.5 Hz), 3.72(1H, sept, J=6.5 Hz), 3.76+3.86(3H, s×2), 4.62+5.08(1H, brs×2), 4.79+5.90(1H, s×2), 6.02(2H, s), 6.22+6.26(1H, d×2, J=8.7 Hz, J=8.6 Hz), 6.79(2H, ddd, J=0.8 Hz, 2.1 Hz, 8.8 Hz), 6.91(1H, d, J=8.6 Hz), 6.98(1H, dd, J=2.0 Hz, 8.6 Hz), 6.99(1H, d, J=2.0 Hz), 7.09(2H, ddd, J=0.8 Hz, 2.1 Hz, 8.8 Hz), 7.35+7.70(1H, d×2, J=8.7 Hz, J=8.6 Hz)

Rf Value: 0.36, 0.33(E. Merck, Kieselgel 60 F$_{254}$/chloroform:methanol=20:1)

EXAMPLE 153

(5RS,6SR,7SR)-6-Carboxy-2,7-dimethyl-5-(3,4-methylenedioxyphenyl)-7-(4-methoxyphenyl) cyclopenteno[1,2-b]pyridine The title compound was prepared in the same manner as in Example 77 using an excess amount of methyl lithium ether solution.

mp: 226°–227° C.

High Resolution FAB-MS(m/e, (C$_{25}$H$_{23}$NO$_{5}$+H)$^{+}$): Calcd: 418.1654 Found: 418.1652

$^1$H-NMR(300 MHz, CDCl$_3$+CD$_3$OD, δ ppm): 1.66(3H, s), 2.49(3H, s), 3.40(1H, d, J=10.3 Hz), 3.81(3H, s), 4.73 (1H, d, J=10.3 Hz), 5.95(2H, s), 6.72(1H, s), 6.73–6.90(2H, m), 6.89(2H, d, J=8.4 Hz), 7.06(1H, d, J=6.3 Hz), 7.22(2H, d, J=8.4 Hz), 7.31(1H, d, J=6.3 Hz)

Rf Value: 0.54(E. Merck, Kieselgel 60F$_{254}$/chloroform:methanol=10:1)

EXAMPLE 154

(5RS,6SR,7SR)-6-Carboxy-2-pyrrolidino-5-(3,4-methylenedioxyphenyl)-7-(4-methoxyphenyl) cyclopenteno[1,2-b]pyridine The title compound was prepared in the same manner as in Example 83.

High Resolution FAB-MS(m/e, (C$_{27}$H$_{26}$N$_{2}$O$_{5}$+H)$^{+}$): Calcd: 459.1920 Found: 459.1910

$^1$H-NMR(300 MHz, CDCl$_3$, δ ppm): 1.84–2.03(4H, m), 3.15(1H, dd, J=8.6 Hz, 9.6 Hz), 3.28–3.44(4H, m), 3.80(3H, s), 4.49(1H, d, J=8.6 Hz), 4.62(1H, d, J=9.6 Hz), 5.95(2H, ABq, J=1.4 Hz, Δv=3.3 Hz), 6.20(1H, d, J=8.6 Hz), 6.72 (1H, s), 6.76(2H, s), 6.86(2H, d, J=8.7 Hz), 7.05(1H, d, J=8.6 Hz), 7.24(2H, d, J=8.7 Hz)

Rf Value: 0.40(E. Merck, Kieselgel 60F$_{254}$/chloroform:methanol=10:1)

EXAMPLE 155

(5RS,6SR,7SR)-6-Carboxy-7-(2,3-dihydro-5-benzofuranyl)-5-(3,4-methylenedioxyphenyl) cyclopenteno[1,2-b]pyridine The title compound was prepared in the same manner as in Example 114 using 2,3-dihydro-5-benzfuranyl magnesium bromide which was prepared by the method described in the literature[Synthesis, 950–953(1988)].

mp: 235°–237° C.

High Resolution FAB-MS(m/e, (C$_{24}$H$_{19}$NO$_{5}$+H)$^{+}$): Calcd: 402.1341 Found: 402.1325

$^1$H-NMR(300 MHz, DMSO-d$_6$, δ ppm): 3.08–3.21(3H, m), 4.42–4.56(4H, m), 6.01(2H, s), 6.65–7.25(8H, m), 8.33 (1H, d, J=3.6 Hz), 12.39(1H, brs)

Rf Value: 0.41(E. Merck, Kieselgel 60F$_{254}$/chloroform:methanol=10:1)

EXAMPLE 156

(5RS,6SR,7SR)-6-Carboxy-7-[2-(2-hydroxyethoxy)-4-methoxyphenyl]-2-(3-hydroxypropylamino)-5-(3,4-methylenedioxyphenyl)cyclopenteno[1,2-b] pyridine (1) (5RS,6SR,7SR)-6-Tert-butoxycarbonyl-7-[2-(2-benzyloxyethoxy)-4-methoxyphenyl]-5-(3,4-methylenedioxyphenyl)cyclopenteno[1,2-b]pyridine (5RS,6SR,7SR)-7-(2-Hydroxy-4-methoxyphenyl)-6-tert-butoxycarbonyl-5-(3,4-methylenedioxyphenyl) cyclopenteno[1,2-b]pyridine which was prepared in Example 50-(5) was allowed to react with 2-benzyloxyethyl bromide in DMF in the presence of CsCO$_3$ to give (5RS, 6SR,7SR)-6-tert-butoxycarbonyl-7-[2-(2-benzyloxyethoxy)-4-methoxyphenyl]-5-(3,4-methylenedioxyphenyl) cyclopenteno[1,2-b]pyridine (2) The title compound was prepared in the same manner as in Example 124-(1),(2) and (4) using (5RS,6SR,7SR)-6-tert-butoxycarbonyl- 7-[2-(2-benzyloxyethoxy)-4-methoxyphenyl]-5-(3,4-methylenedioxyphenyl) cyclopenteno[1,2-b]pyridine and N-(3-benzyloxypropyl) benzimidoyl chloride.

mp: 168°–173° C.

High Resolution FAB-MS(m/e, (C$_{28}$H$_{30}$N$_{2}$O$_{8}$+H)$^{+}$): Calcd: 523.2080 Found: 523.2084

¹H-NMR(300 MHz, CD₃OD, δ ppm): 1.70(2H, quint, J=6.2 Hz), 3.07(1H, t, J=8.7 Hz), 3.20–3.37(2H, m), 3.55 (2H, t, J=5.0 Hz), 3.65–3.80(2H, m), 3.76(3H, s), 3.91(1H, td, J=5.0 Hz, 10.0 Hz), 4.06(1H, td, J=5.0 Hz, 10.0 Hz), 4.40(1H, d, J=8.7 Hz), 4.83(1H, d, J=8.7 Hz), 5.88(2H, s), 6.37(1H, dd, J=0.9 Hz, 8.5 Hz), 6.48(1H, dd, J=2.4 Hz, 8.3 Hz), 6.53(1H, d, J=2.4 Hz), 6.70–6.78(3H, m), 6.98(1H, d, J=8.3 Hz), 7.05(1H, d, J=8.5 Hz)

Rf Value: 0.32(E. Merck, Kieselgel 60F$_{254}$/chloroform:methanol=10:1)

EXAMPLE 157

(5RS,6SR,7SR)-6-Carboxy-7-[2-(2-hydroxyethoxy)-4-methoxyphenyl]-2-(N-methyl-3-hydroxypropylamino)-5-(3,4-methylenedioxyphenyl)cyclopenteno[1,2-b]pyridine The intermediate of Example 156 was N-methylated in the same manner as in Example 127-(2) and then subjected to the same reaction as in Example 156-(2) to give the title compound.

mp: 92°–95° C.

High Resolution FAB-MS(m/e, (C₂₉H₃₂N₂O₈+H)⁺): Calcd: 537.2237 Found: 537.2223

¹H-NMR(300 MHz, CD₃OD, δ ppm): 1.55–1.78(2H, m), 2.95(3H, s), 3.13(1H, t, J=9.2 Hz), 3.33–3.47(3H, m), 3.60–3.72(1H, m), 3.67(2H, t, J=5.1 Hz), 3.78(3H, s), 3.86 (1H, td, J=5.1 Hz, 10.1 Hz), 4.08(1H, td, J=5.1 Hz, 10.1 Hz), 4.40(1H, d, J=9.2 Hz), 4.78(1H, d, J=9.2 Hz), 5.91(2H, s), 6.49(1H, dd, J=1.0 Hz, 8.7 Hz), 6.50(1H, dd, J=2.4 Hz, 8.4 Hz), 6.55(1H, d, J=2.4 Hz), 6.72–6.77(3H, m), 7.01(1H, d, J=8.4 Hz), 7.10(1H, dd, J=0.9 Hz, 8.7 Hz)

Rf Value: 0.40(E. Merck, Kieselgel 60F$_{254}$/chloroform:methanol=10:1)

EXAMPLE 158

(5RS,6SR,7SR)-6-Carboxy-2-cyclopropylamino-5-(3,4-methylenedioxyphenyl)-7-(4-methoxyphenyl)cyclopenteno[1,2-b]pyridine The title compound was prepared in the same manner as in Example 83.

mp: 136°–138.5° C.

High Resolution FAB-MS(m/e, (C₂₆H₂₄N₂O₅+H)⁺): Calcd: 445.1763 Found: 445.1754

¹H-NMR(300 MHz, CDCl₃, δ ppm): 0.48–0.56(2H, m), 0.68–0.76(2H, m), 2.37–2.46(1H, m), 2.95(1H, t, J=8.3 Hz), 3.63(3H, s), 4.32(1H, d, J=8.3 Hz), 4.59(1H, d, J=8.3 Hz), 5.93(2H, ABq, J=1.5 Hz, Δν=2.1 Hz), 6.65–6.82(4H, m), 6.77(2H, d, J=8.7 Hz), 7.12(2H, d, J=8.7 Hz), 7.22(1H, dd, J=0.9 Hz, 8.5 Hz)

Rf Value: 0.22(E. Merck, Kieselgel 60F$_{254}$/chloroform:methanol=30:1)

EXAMPLE 159

(5RS,6SR,7SR)-6-Carboxy-2-(N-methylisopropylamino)-5-(3,4-methylenedioxyphenyl)-7-(4-methoxyphenyl)cyclopenteno[1,2-b]pyridine The precursor of the compound of Example 151, tert-butyl ester, was N-methylated by heating at 100° C. in a mixture of formic acid and formaline. The tert-butyl ester was cleaved to give the title compound.

mp: 94°–96° C.

High Resolution FAB-MS(m/e, (C₂₇H₂₈N₂O₅+H)⁺): Calcd: 461.2078 Found: 461.2078

¹H-NMR(300 MHz, CDCl₃, δ ppm): 1.05(3H, d, J=6.7 Hz), 1.11(3H, d, J=6.7 Hz), 2.77(3H, s), 3.14(1H, t, J=9.2 Hz), 3.81(3H, s), 4.48(1H, d, J=9.2 Hz), 4.60(1H, d, J=9.2 Hz), 4.69(1H, sept, J=6.7 Hz), 5.94(1H, d, J=1.4 Hz), 5.95(1H, d, J=1.4 Hz), 6.34(1H, d, J=8.6 Hz), 6.71–6.76(3H, m), 6.86(2H, d, J=8.8 Hz), 7.06(1H, d, J=8.6 Hz), 7.23(2H, d, J=8.8 Hz)

Rf Value: 0.14(E. Merck, Kieselgel 60F$_{254}$/chloroform:methanol=30:1)

EXAMPLE 160

(5RS,6SR,7SR)-6-Carboxy-2-(N-methylcyclopropylamino)-5-(3,4-methylenedioxyphenyl)-7-(4-methoxyphenyl)cyclopenteno[1,2-b]pyridine The title compound was prepared in the same manner as in Example 159.

mp: 94°–98° C.

High Resolution FAB-MS(m/e, (C₂₇H₂₆N₂O₅+H)⁺): Calcd: 459.1920 Found: 459.1934

¹H-NMR(300 MHz, CDCl₃, δ ppm): 0.53–0.70(2H, m), 0.70–0.90(2H, m), 2.38–2.47(1H, m), 2.99(3H, s), 3.17(1H, dd, J=8.9 Hz, 9.5 Hz), 3.80(3H, s), 4.49(1H, d, J=8.9 Hz), 4.61(1H, d, J=9.5 Hz), 5.94(2H, ABq, J=1.5 Hz, Δν=2.6 Hz), 6.72(1H, d, J=1.1 Hz), 6.764(1H, d, J=1.1 Hz), 6.766(1H, s), 6.83(1H, dd, J=0.9 Hz, 8.6 Hz), 6.86(2H, d, J=8.7 Hz), 7.09(1H, dd, J=0.9 Hz, 8.6 Hz), 7.22(2H, d, J=8.7 Hz)

Rf Value: 0.32(E. Merck, Kieselgel 60F$_{254}$/chloroform:methanol=30:1)

EXAMPLE 161

(5RS,6SR,7SR)-2-Ethylamino-6-carboxy-7-[2-(2-carboxyethyl-4-methoxyphenyl)-5-(3,4-methylenedioxyphenyl)cyclopenteno[1,2-b]pyridine The title compound was prepared in the same manner as in Example 124-(1),(2) and (4) using (5RS,6SR,7SR)-tert-butoxycarbonyl-5-(3,4-methylenedioxyphenyl)-7-[2-(2-methoxycarbonylethyl)-4-methoxyphenyl]cyclopenteno[1,2-b]pyridine.

mp: 225°–228° C.

High Resolution FAB-MS(m/e, (C₂₈H₂₈N₂O₇+H)⁺): Calcd: 505.1975 Found: 505.1985

¹H-NMR(300 MHz, DMSO-d₆, δ ppm): 0.99(3H, t, J=7.2 Hz), 2.35–3.43(6H, m), 2.99(1H, t, J=8.9 Hz), 3.71(3H, s), 4.32(1H, d, J=8.9 Hz), 4.61(1H, d, J=8.9 Hz), 6.00(2H, s), 6.22(1H, d, J=8.3 Hz), 6.35(1H, t, J=5.6 Hz), 6.68–7.02(7H, m), 12.22(2H, brs)

Rf Value: 0.50(E. Merck, Kieselgel 60F$_{254}$/chloroform:methanol:acetic acid=10:1:1)

EXAMPLE 162

(5RS,6SR,7SR)-6-Carboxy-7-[2-(2-carboxy-2-propenyl)-4-methoxyphenyl]-2-propylamino-5-(3,4-methylenedioxyphenyl)cyclopenteno[1,2-b]pyridine The title compound was prepared in the same manner as in Example 124-(1),(2) and (3) using 2-propenyl compound of (5RS,6SR,7SR)-6-tert-butoxycarbonyl-5-(3,4-methylenedioxyphenyl)-7-[2-(2-methoxycarbonylpropenyl)-4-methoxyphenyl]cyclopenteno[1,2-b]pyridine.

mp: 144°–148° C.

High Resolution FAB-MS(m/e, $(C_{30}H_{30}N_2O_7+H)^+$): Calcd: 531.2131 Found: 531.2112

$^1$H-NMR(300 MHz, CD$_3$OD, δ ppm): 0.91(3H, t, J=7.3 Hz), 1.56(2H, sext, J=7.3 Hz), 3.06–3.19(3H, m), 3.44–3.94 (2H, m), 3.74(3H, s), 4.42(1H, d, J=8.6 Hz), 4.85(1H, m), 5.44(1H, brs), 5.92(2H, s), 6.14(1H, brs), 6.46(1H, d, J=8.4 Hz), 6.73–6.80(5H, m), 6.99(1H, d, J=7.9 Hz), 7.16(1H, d, J=8.6 Hz)

Rf Value: 0.28(E. Merck, Kieselgel 60F$_{254}$/ chloroform:methanol:acetic acid=20:1:1)

Each compound in the following Examples 163 and 164 was prepared by hydrogenation of (5RS,6SR,7SR)-6-carboxy-7-[2-(2-carboxy-2-propenyl)-4-methoxyphenyl]-2-propylamino-5-(3,4-methylendioxyphenyl)cyclopenteno[1,2-b]pyridine which was prepared in Example 162 using palladium black as a catalyst.

EXAMPLE 163

(5RS,6SR,7SR)-6-Carboxy-7-[2-(2-carboxypropyl)-4-methoxyphenyl]-2-propylamino-5-(3,4-methylenedioxyphenyl)cyclopenteno[1,2-b]pyridine (one of diastereomer)

mp: 138°–140° C.

High Resolution FAB-MS(m/e, $(C_{30}H_{32}N_2O_7+H)^+$): Calcd: 533.2288 Found: 533.2281

$^1$H-NMR(300 MHz, CD$_3$OD, δ ppm): 0.91(3H, t, J=7.3 Hz), 1.22(3H, d, J=6.0 Hz), 1.55(2H, sext, J=7.3 Hz), 2.77–2.92(2H, m), 3.05–3.11(1H, m), 3.13(2H, t, J=7.3 Hz), 3.15(1H, t, J=9.1 Hz), 3.75(3H, s), 4.44(1H, d, J=9.1 Hz), 4.86(1H, t, J=9.1 Hz), 5.93(2H, s), 6.48(1H, d, J=8.6 Hz), 6.73–6.80(5H, m), 6.96(1H, d, J=8.5 Hz), 7.18(1H, d, J=8.6 Hz)

Rf Value: 0.50(E. Merck, Kieselgel 60F$_{254}$/ chloroform:methanol:acetic acid=20:1:1)

EXAMPLE 164

(5RS,6SR,7SR)-6-Carboxy-7-[2-(2-carboxypropyl)-4-methoxyphenyl]-2-propylamino-5-(3,4-methylenedioxyphenyl)cyclopenteno[1,2-b]pyridine (the other diastereomer)

mp: 93°–96° C.

High Resolution FAB-MS(m/e, $(C_{30}H_{32}N_2O_7+H)^+$): Calcd: 533.2288 Found: 533.2314

$^1$NMR(300 MHz, CD$_3$OD, δ ppm): 0.91(3H, t, J=7.3 Hz), 1.33(3H, d, J=8.6 Hz), 1.48(2H, sext, J=7.3 Hz), 2.56–2.70 (1H, m), 2.74–2.90(1H, m), 3.05–3.20(4H, m), 3.75(3H, s), 4.44(1H, d, J=8.9 Hz), 4.75–4.95(1H, m), 5.92(2H, s), 6.46(1H, d, J=8.9 Hz), 6.74–6.78(5H, m), 6.93(1H, d, J=7.6 Hz), 7.16(1H, d, J=8.6 Hz)

Rf Value: 0.35(E. Merck, Kieselgel 60F$_{254}$/ chloroform:methanol:acetic acid=20:1:1)

EXAMPLE 165

(5RS,6SR,7SR)-6-Carboxy-7-[2-(2-carboxypropyl)-4-methoxyphenyl]-5-(3,4-methylenedioxyphenyl) cyclopenteno[1,2-b]pyridine(the other diastereomer)

The title compound was prepared in the same manner as in Example 102-(3) and 103 using (5RS,6SR,7SR)-6-tert-butoxycarbonyl-5-(3,4-methylenedioxyphenyl)-7-[2-(2-methoxycarbonylpropyl)-4-methoxyphenyl]cyclopenteno[1,2-b]pyridine(the other diastereomer) which was prepared in Example 102-(2).

mp: 125°–127° C.

High Resolution FAB-MS(m/e, $(C_{27}H_{25}NO_7+H)^+$): Calcd: 476.1709 Found: 476.1719

$^1$H-NMR(300 MHz, CDCl$_3$, δ ppm): 1.14(3H, d, J=6.9 Hz), 2.60(1H, dd, J=9.3 Hz, 12.7 Hz), 2.75–2.90(1H, m), 3.18–3.26(2H, m), 3.76(3H, s), 4.64(1H, d, J=9.5 Hz), 5.03(1H, d, J=9.5 Hz), 5.95(1H, d, J=1.4 Hz), 5.96(1H, d, J=1.4 Hz), 6.69–6.88(6H, m), 7.15(1H, dd, J=4.9 Hz, 7.8 Hz), 7.35(1H, d, J=7.8 Hz), 8.44(1H, d, J=4.9 Hz)

Rf Value: 0.40(E. Merck, Kieselgel 60F$_{254}$/ chloroform:methanol:acetic acid=10:1:1)

EXAMPLE 166

(5RS,6SR,7SR)-6-Carboxy-5-(3,4-methylenedioxyphenyl)-7-[2-(3-methoxypropyl)-4-methoxyphenyl]cyclopenteno[1,2-b]pyridine The title compound was prepared in the same manner as in Example 113 using 3-methoxypropen-1-yltributyltin.

mp: 78°–82° C.

High Resolution FAB-MS(m/e, $(C_{27}H_{27}NO_6+H)^+$): Calcd: 462.1917 Found: 462.1924

$^1$H-NMR(300 MHz, CDCl$_3$, δ ppm): 1.80–2.00(2H, m), 2.20–3.00(2H, m), 3.20(3H, s), 3.29–3.48(3H, m), 3.79(3H, s), 4.63(1H, d, J=9.9 Hz), 4.97(1H, d, J=9.9 Hz), 5.97(1H, d, J=1.4 Hz), 5.98(1H, d, J=1.4 Hz), 6.74(1H, brs), 6.75(1H, d, J=8.1 Hz), 6.76(1H, brs), 6.78(1H, dd, J=1.6 Hz, 7.9 Hz), 6.80(1H, d, J=7.9 Hz), 6.89–6.95(1H, m), 7.11(1H, dd, J=4.9 Hz, 7.6 Hz), 7.30(1H, d, J=7.6 Hz), 8.44(1H, d, J=4.9 Hz)

Rf Value: 0.40(E. Merck, Kieselgel 60F$_{254}$/ chloroform:methanol=15:1)

EXAMPLE 167

(5RS,6SR,7SR)-7-[2-(2-Acetoxymethylcarbonylethyl)-4-methoxyphenyl]-6-carboxy-5-(3,4-methylenedioxyphenyl)cyclopenteno[1,2-b]pyridine (1) (5RS,6SR,7SR)-7-[2-(2-Carboxylethyl)-4-methoxyphenyl]-6-tert-butoxycarbonyl-5-(3,4-methylenedioxyphenyl)cyclopenteno[1,2-b]pyridine (5RS,6SR,7SR)-7-[2-(2-Carboxyethyl)-4-methoxyphenyl]-6-tert-butoxycarbonyl-5-(3,4-methylenedioxyphenyl)cyclopenteno[1,2-b]pyridine was prepared in the same manner as in Example 2 using (5RS,6SR,7SR)-6-tert-butoxycarbonyl-5-(3,4-methylenedioxyphenyl)-7-[2-(2-methoxycarbonylethyl)-4-methoxyphenyl]cyclopenteno[1,2-b]pyridine which was prepared in Example 100-(1).

(2) (5RS,6SR,7SR)-7-[2-(2-Diazomethylcarbonylethyl)-4-methoxyphenyl]-6-tert-butoxycarbonyl-5-(3,4-methylenedioxyphenyl)cyclopenteno[1,2-b]pyridine To a THF solution(1.5 ml) of (5RS,6SR,7SR)-7-[2-(2-carboxyethyl)-4-methoxyphenyl]-6-tert-butoxycarbonyl-5-(3,4-methylenedioxyphenyl)cyclopenteno[1,2-b]pyridine (151 mg,0.292 mmol) which was prepared in (1) were added a THF solution(1 ml) of TEA(45 µl) at −10° C. and then a THF(1 ml) solution of propyl chloroformate(39 µl). The mixture was stirred at 0° C. for 1 h, treated with 2% diazomethane-ether solution(4 ml) and stirred for 10 h. Acetic acid(0.5 ml) was added to the reaction solution. After removal of the solvent under reduced pressure the residue was purified by dry column flash chromatography(E. Merck Kieselgel 60/hexane:AcOEt=2:1 to 1:1) to give (5RS,6SR,7SR)-7-[2-(2-diazomethylcarbonylethyl)-4-methoxyphenyl]-6-tert-butoxycarbonyl-5-(3,4-methylenedioxyphenyl)cyclopenteno[1,2-b]pyridine(78.3 mg).

(3) The title compound was prepared in the same manner as in Example 150-(2) using (5RS,6SR,7SR)-7-[2-(2-diazomethylcarbonylethyl)-4-methoxyphenyl]-6-tert-butoxycarbonyl-5-(3,4-methylenedioxyphenyl)cyclopenteno[1,2-b]pyridine which was prepared in (2).

mp: 94°–100° C.

High Resolution FAB-MS(m/e, $(C_{29}H_{27}NO_8+H)^+$): Calcd: 518.1815 Found: 518.1837

$^1$H-NMR(300 MHz, Acetone-$d_6$, δ ppm): 2.06(3H, s), 2.65–3.25(4H, m), 3.42(1H, t, J=9.8 Hz), 3.77(3H, s), 4.63 (1H, d, J=9.8 Hz), 4.69(2H, s), 4.95(1H, d, J=9.8 Hz), 6.01(2H, s), 6.75(1H, dd, J=2.6 Hz, 8.5 Hz), 6.83(1H, d, J=2.6 Hz), 6.84–6.90(3H, m), 7.05(1H, d, J=8.5 Hz), 7.18 (1H, dd, J=4.8 Hz, 7.5 Hz), 7.31(1H, td, J=1.6 Hz, 7.5 Hz), 8.35(1H, td, J=1.6 Hz, 4.8 Hz)

Rf Value: 0.55(E. Merck, Kieselgel 60$F_{254}$/chloroform:methanol=10:1)

EXAMPLE 168

(5RS,6SR,7SR)-6-Carboxy-7-[2-(2-hydroxymethylcarbonylethyl)-4-methoxyphenyl]-5-(3,4-methylenedioxyphenyl)cyclopenteno[1,2-b]pyridine The title compound was prepared by treating (5RS,6SR,7SR)-7-[2-(2-acetoxymethylcarbonylethyl)-4-methoxyphenyl]-6-carboxy-5-(3,4-methylenedioxyphenyl)cyclopenteno[1,2-b]pyridine with 4N $K_2CO_3$ in dioxane.

mp: 116°–125° C.

High Resolution FAB-MS(m/e, $(C_{27}H_{25}NO_7+H)^+$): Calcd: 476.1709 Found: 476.1701

$^1$H-NMR(300 MHz, Acetone-$d_6$, δ ppm): 2.65–3.00(3H, m), 3.05–3.25(1H, m), 3.41(1H, t, J=9.9 Hz), 3.77(3H, s), 4.10(1H, d, J=8.6 Hz), 4.13(1H, d, J=8.6 Hz), 4.63(1H, d, J=9.9 Hz), 4.96(1H, d, J=9.9 Hz), 6.02(2H, s), 6.75(1H, dd, J=2.8 Hz, 8.5 Hz), 6.82(1H, d, J=2.8 Hz), 6.84–6.90(3H, m), 7.05(1H, d, J=8.5 Hz), 7.20(1H, dd, J=4.7 Hz, 7.7 Hz), 7.32(1H, td, J=1.4 Hz, 7.7 Hz), 8.35(1H, td, J=1.4 Hz, 4.7 Hz)

Rf Value: 0.33(E. Merck, Kieselgel 60$F_{254}$/chloroform:methanol=10:1)

EXAMPLE 169

(5RS,6SR,7SR)-6-Carboxy-7-[2-(3-carboxypropyl)-4-methoxyphenyl]-5-(3,4-methylenedioxyphenyl)cyclopenteno[1,2-b]pyridine To a methanol solution of (5RS,6SR,7SR)-7-[2-(2-diazomethylcarbonylethyl)-4-methoxyphenyl]-6-tert-butoxycarbonyl-5-(3,4-methylenedioxyphenyl)cyclopenteno[1,2-b]pyridine which was prepared in Example 167-(2) was added a triethylamine solution of benzoic acid silver salt at 100° C. The product was treated with TFA and hydrolized with base to give the title compound.

mp: 110°–113° C.

High Resolution FAB-MS(m/e, $(C_{27}H_{27}NO_7+H)^+$): Calcd: 490.1866 Found: 490.1895

$^1$H-NMR(300 MHz, CDCl$_3$, δ ppm): 0.96(3H, d, J=6.3 Hz), 2.12(1H, dd, J=9.4 Hz, 13.8 Hz), 2.37–2.42(1H, m), 2.49(1H, dd, J=10.2 Hz, 13.8 Hz), 2.56(1H, dd, J=9.2 Hz, 13.6 Hz), 2.88(1H, dd, J=5.8 Hz, 13.6 Hz), 3.44(1H, d, J=9.8 Hz), 3.77(3H, s), 4.66(1H, d, J=9.8 Hz), 5.01(1H, d, J=9.8 Hz), 5.98(1H, d, J=1.3 Hz), 5.994(1H, d, J=1.3 Hz), 6.69–6.96(6H, m), 7.13(1H, dd, J=4.9 Hz, 7.8 Hz), 7.34(1H, d, J=7.8 Hz), 8.42(1H, d, J=4.9 Hz)

Rf Value: 0.47(E. Merck, Kieselgel 60$F_{254}$/chloroform:methanol:acetic acid=10:1:1)

EXAMPLE 170

(5RS,6SR,7SR)-6-Carboxy-7-[2-(3-carboxy-2-propylmethyl)-4-methoxyphenyl]-5-(3,4-methylenedioxyphenyl)cyclopenteno[1,2-b]pyridine Title compound was prepared in the same manner as in Example 167-(1),(2) and Example 169 using (5RS,6SR,7SR)-6-tert-butoxycarbonyl-5-(3,4-methylenedioxyphenyl)-7-[2-(2-methoxycarbonylpropyl)-4-methoxyphenyl]cyclopenteno[1,2-b]pyridine.

mp: 98°–101° C.

High Resolution FAB-MS(m/e, $(C_{27}H_{25}NO_7+H)^+$): Calcd: 476.1709 Found: 476.1707

$^1$H-NMR(300 MHz, CDCl$_3$, δ ppm): 1.84–2.10(2H, m), 2.35–2.48(2H, m), 270–2.91(2H, m), 3.34(1H, dd, J=7.9 Hz, 9.6 Hz), 3.77(3H, s), 4.64(1H, d, J=9.6 Hz), 5.06(1H, d, J=9.9 Hz), 5.97(2H, s), 6.71–6.89(6H, m), 7.13(1H, dd, J=4.9 Hz, 7.7 Hz), 7.33(1H, d, J=7.7 Hz), 8.45(1H, d, J=4.9 Hz)

Rf Value: 0.40(E. Merck, Kieselgel 60$F_{254}$/chloroform:methanol:acetic acid=10:1:1)

Each compound in the following Examples 171–175 was prepared in the same manner as in Example 161.

EXAMPLE 171

(5RS,6SR,7SR)-6-Carboxy-7-[2-(2-carboxypropyl)-4-methoxyphenyl]-2-isopropylamino-5-(3,4-methylenedioxyphenyl)cyclopenteno[1,2-b]pyridine mp: 149°–152° C.

$^1$H-NMR(300 MHz, acetone-$d_6$, δ ppm): 1.10(3H, d, J=6.3 Hz), 1.13(3H, d, J=6.3 Hz), 1.22(3H, d, J=6.5 Hz), 2.80–3.00(2H, m), 3.10–3.17(1H, m), 3.29(1H, dd, J=8.9 Hz, 9.5 Hz), 3.75(3H, s), 3.75–3.87(1H, m), 4.47(1H, d, J=8.9 Hz), 4.90(1H, d, J=9.5 Hz), 5.20(1H, brs), 6.00(2H, s), 6.38(1H, d, J=8.5 Hz ), 6.72–6.88(5H, m), 7.05(1H, d, J=8.3 Hz), 7.08(1H, d, J=8.5 Hz)

Rf Value: 0.40(E. Merck, Kieselgel 60$F_{254}$/chloroform:methanol=10:1)

EXAMPLE 172

(5RS,6SR,7SR)-6-Carboxy-7-[2-(2-carboxy-3-hydroxypropyl)-4-methoxyphenyl]-2-propylamino-5-(3,4-methylenedioxyphenyl)cyclopenteno[1,2-b]pyridine(one of diastereomers)

mp: 176° C. (dec.)

High Resolution FAB-MS(m/e, $(C_{30}H_{32}N_2O_8+H)^+$): Calcd: 549.2237 Found: 549.2217

$^1$H-NMR(300 MHz, CD$_3$OD, δ ppm): 0.92(3H, t, J=7.2 Hz), 1.57(2H, sext, J=7.2 Hz), 2.58–3.38(4H, m), 3.14(2H, t, J=7.2 Hz), 3.74(3H, s), 3.66–3.88(2H, m), 4.40–4.50(1H, m), 4.91–5.04(1H, m), 5.91(2H, s), 6.52(1H, d, J=7.8 Hz), 6.68–6.83(5H, m), 6.98(1H, d, J=8.4 Hz), 7.25(1H, d, J=8.6 Hz )

EXAMPLE 173

(5RS,6SR,7SR)-2-Ethylamino-6-Carboxy-7-[2-(2-carboxy-4-methoxyphenyl]-5-(3,4-methylenedioxyphenyl)cyclopenteno[1,2-b]pyridine (one of diastereomers)

EXAMPLE 174

(5RS,6SR,7SR)-2-Isobutylamino-6-carboxy-7-[2-(2-carboxypropyl)-4-methoxyphenyl]-5-(3,4-methylenedioxyphenyl)cyclopenteno[1,2-b]pyridine (one of diastereomers)

$^1$H-NMR(300 MHz, CDCl$_3$, δ ppm): 0.91(6H, d, J=6.6 Hz), 1.31(3H, d, J=6.3 Hz), 1.72–1.88(1H, m), 2.62(1H, t, J=12.5 Hz), 2.87(2H, d, J=6.6 Hz), 2.88–3.02(1H, m), 3.29–3.40(1H, m), 3.49(1H, t, J=9.2 Hz), 3.75(3H, s), 4.49 (1H, d, J=9.2 Hz), 4.86(1H, d, J=9.2 Hz), 5.99(2H, s), 6.28(1H, d, J=8.8 Hz), 6.68(1H, d, J=2.5 Hz), 6.75–6.87(4H, m), 6.99(1H, d, J=8.8 Hz), 7.18(1H, d, J=8.8 Hz)

Rf Value: 0.67(E. Merck, Kieselgel 60F$_{254}$/chloroform:methanol:acetic acid=10:1:1)

EXAMPLE 175

(5RS,6SR,7SR)-6-Carboxy-7-[2-(2-carboxypropyl)-4-methoxyphenyl]-2-cyclopentylamino-5-(3,4-methylenedioxyphenyl)cyclopenteno[1,2-b]pyridine (one of diastereomers)

mp: 154°–156° C.

$^1$H-NMR(300 MHz, CDCl$_3$, δ ppm): 1.30(3H, d, J=6.3 Hz), 1.35–2.03(8H, m), 2.55–2.70(1H, m), 2.85–3.01(1H, m), 3.21–3.35(1H, m), 3.47(1H, t, J=9.2 Hz), 3.63–3.75(1H, m), 3.75(3H, s), 4.48(1H, d, J=9.2 Hz), 4.85(1H, d, J=9.2 Hz), 5.98(2H, s), 6.32(1H, d, J=8.6 Hz), 6.67(1H, d, J=2.4 Hz), 6.75–6.85(4H, m), 6.98(1H, d, J=8.6 Hz), 7.18(1H, d, J=8.6 Hz)

Rf Value: 0.48(E. Merck, Kieselgel 60F$_{254}$/chloroform:methanol:acetic acid=10:1:1)

EXAMPLE 176

(5RS,6SR,7SR)-6-Carboxy-7-[2-(2-carboxypropyl)-4-methoxyphenyl]-2-[N-(methyl)propylamino]-5-(3,4-methylenedioxyphenyl)cyclopenteno[1,2-b]pyridine(one of diastereomers)

(5RS,6SR,7SR)-6-Carboxy-7-[2-(2-carboxypropyl)-4-methoxyphenyl]-2-propylamino-5-(3,4-methylenedioxyphenyl)cyclopenteno[1,2-b]pyridine was treated with diazomethane in methanol to give the dimethyl ester, which was subjected to the same reaction as in Example 160 to give the title compound. Each compound in the following Examples 177–179 was prepared in the same manner as in Example 176.

mp: 90°–95° C.

$^1$H-NMR(300 MHz, CDCl$_3$, δ ppm): 0.77(3H, t, J=7.4 Hz), 1.22(3H, d, J=6.6 Hz), 1.47(2H, sext, J=7.4 Hz), 2.80–3.13(3H, m), 2.90(3H, s), 3.18(1H, t, J=8.7 Hz), 3.30 (2H, t, J=7.4 Hz), 3.76(3H, s), 4.53(1H, d, J=8.7 Hz), 4.97(1H, d, J=8.7 Hz), 5.94(2H, s), 6.29(1H, d, J=8.6 Hz), 6.69–6.80(5H, m), 6.92(1H, d, J=9.2 Hz), 7.06(1H, d, J=8.6 Hz)

Rf Value: 0.54(E. Merck, Kieselgel 60F$_{254}$/chloroform:methanol:acetic acid=20:1:1)

EXAMPLE 177

(5RS,6SR,7SR)-6-Carboxy-7-[2-(2-carboxypropyl)-4-methoxyphenyl]-2-[N-(methyl)isopropylamino]-5-(3,4-methylenedioxyphenyl)cyclopenteno[1,2-b]pyridine(one of diastereomers)

EXAMPLE 178

(5RS,6SR,7SR)-6-Carboxy-7-[2-(2-carboxypropyl)-4-methoxyphenyl]-2-[N-(methyl)ethylamino]-5-(3,4-methylenedioxyphenyl)cyclopenteno[1,2-b]pyridine (one of diastereomers)

EXAMPLE 179

(5RS,6SR,7SR)-6-Carboxy-7-[2-(2-carboxy-2-hydroxypropyl)- 4-methoxyphenyl]-2-[N-(methyl)propylamino]-5-(3,4-methylenedioxyphenyl)cyclopenteno[1,2-b]pyridine(one of diastereomers)

mp: 158°–162° C.

$^1$H-NMR(300 MHz, CD$_3$OD, δ ppm): 0.76(3H, t, J=7.4 Hz), 1.46(2H, sext, J=7.4 Hz), 2.90(3H, s), 2.80–3.80(8H, m), 3.75(3H, s), 4.45(1H, d, J=8.0 Hz), 4.68–5.02(1H,m), 5.90(2H, s), 6.38(1H, d, J=8.6 Hz), 6.68–6.86(5H, m), 6.90(1H, d, J=8.6 Hz), 7.05(1H, d, J=8.5 Hz)

Rf Value: 0.49(E. Merck, Kieselgel 60F$_{254}$/chloroform:methanol=5:1)

EXAMPLE 180

(5RS,6SR,7SR)-6-Carboxy-7-[2-(2-carboxyethyl)-4-methoxyphenyl]-2-(N,N-diethylamino)-5-(3,4-methylenedioxyphenyl)cyclopenteno[1,2-b]pyridine (5RS,6SR,7SR)-2-Ethylamino-6-carboxy-7-[2-(2-carboxyethyl)-4-methoxyphenyl]-5-(3,4-methylenedioxyphenyl)cyclopenteno[1,2-b]pyridine which was prepared in Example 161 was treated with diazomethane-ether solution in methanol to give the dimethy ester compound, which was treated with acetoaldehyde and sodium cyanoborohydride in acetonitrile to give the title compound.

High Resolution FAB-MS(m/e, (C$_{30}$H$_{32}$N$_2$O$_7$+H)$^+$): Calcd: 533.2288 Found: 533.2281

$^1$H-NMR(300 MHz, CDCl$_3$, δ ppm): 1.05(6H, t, J=6.9 Hz), 2.58–2.85(2H, m), 3.06–3.22(2H, m), 3.17(1H, t, J=8.3 Hz), 3.29–3.48(4B, m), 3.78(3H, s), 4.53(1H, d, J=8.3 Hz), 4.96(1H, d, J=8.3 Hz), 5.94(2H, s), 6.31(1H, d, J=8.6 Hz), 6.68–6.81(5H, m), 6.93(1H, d, J=8.5 Hz), 7.07(1H, d, J=8.6 Hz)

Rf Value: 0.61(E. Merck, Kieselgel 60F$_{254}$/chloroform:methanol:acetic acid=10:1:1)

Each compound in the following Examples 181–183 was prepared in the same manner as in Example 180.

EXAMPLE 181

(5RS,6SR,7SR)-6-Carboxy-7-[2-(2-carboxyethyl)-4-methoxyphenyl]-2-(N-(ethyl)propylamino)-5-(3,4-methylenedioxyphenyl)cyclopenteno[1,2-b]pyridine High Resolution FAB-MS(m/e, (C$_{31}$H$_{34}$N$_2$O$_7$+H)$^+$): Calcd: 547.2444 Found: 547.2463

¹H-NMR(300 MHz, CDCl₃, δ ppm): 0.78(3H, t, J=7.4 Hz), 1.02(3H, t, J=6.9 Hz), 1.48(2H, sext, J=7.4 Hz), 2.57–2.86(2H, m), 3.07–3.47(7H, m), 3.77(3H, s), 4.53(1H, d, J=8.6 Hz), 4.94(1H, d, J=8.6 Hz), 5.94(2H, s), 6.27(1H, d, J=8.6 Hz), 6.67–6.82(5H, m), 6.93(1H, d, J=8.3 Hz), 7.05(1H, d, J=8.6 Hz)

Rf Value: 0.66(E. Merck, Kieselgel 60F₂₅₄/chloroform:methanol:acetic acid=10:1:1)

EXAMPLE 182

(5RS,6SR,7SR)-6-Carboxy-7-[2-(2-carboxyethyl)-4-methoxyphenyl]-2-(N,N-diethylamino)-5-(3,4-methylenedioxyphenyl)cyclopenteno[1,2-b]pyridine
(one of diastereomers)

EXAMPLE 183

(5RS,6SR,7SR)-6-Carboxy-7-[2-(2-carboxypropyl)-4-methoxyphenyl]-2-[N-(ethyl)propylamino]-5-(3,4-methylenedioxyphenyl)cyclopenteno[1,2-b]pyridine
(one of diastereomers)

EXAMPLE 184

(5RS,6SR,7SR)-6-Carboxy-7-[2-(2-carboxypropyl)-4-methoxyphenyl]-2-pyrrolidino-5-(3,4-methylenedioxyphenyl)cyclopenteno[1,2-b]pyridine
(one of diastereomers)

(1) (5RS,6SR,7SR)-2-(4-Hydroxybutylamino)-5-(3,4-methylenedioxyphenyl)-6-methoxycarbonyl-7-[2-(2-methoxycarbonylpropyl-4-methoxyphenyl]cyclopenteno[1,2-b]pyridine (5RS,6SR,7SR)-6-Tert-butoxycarbonyl-5-(3,4-methylenedioxyphenyl)-7-[2-(2-methoxycarbonylpropyl-4-methoxyphenyl]cyclopenteno[1,2-b]pyridine which was prepared in Example 102-(2) was reacted with N-(4-benzoyloxybutyl)bezimidoyl chloride in the same manner as in Example 133 and subjected to the same reaction as in Example 134 to give the corresponding dibasic acid. The dibasic acid was treated with diazomethane to give (5RS, 6SR,7SR)-2-(4-hydroxybutylamino)-5-(3,4-methylenedioxyphenyl)-6-methoxycarbonyl-7-[2-(2-methoxycarbonylpropyl)- 4-methoxyphenyl]cyclopenteno[1,2-b]pyridine.

(2) (5RS,6SR,7SR)-2-(4-Hydroxybutylamino)-5-(3,4-methylenedioxyphenyl)-6-methoxycarbonyl-7-[2-(2-methoxycarbonylpropyl-4-methoxyphenyl]cyclopenteno[1,2-b]pyridine which was prepared in (1) was reacted with ruthenium(II) chloride tristriphenylphosphine complex in dioxane at 150°–200° C. in a sealed tube to give 2-pyrrolidino compound. The pyrrolidino compound was hydrolized with base to give the title compound.

mp: 121°–133° C.

¹H-NMR(300 MHz, CDCl₃, δ ppm): 1.20–1.30(3H, m), 1.82–1.96(4H, m), 2.65(1H, dd, J=9.4 Hz, 13.5 Hz), 2.92–2.99(1H, m), 3.25(1H, t, J=9.1 Hz), 3.24–3.37(4H, m), 3.43(1H, dd, J=6.3 Hz, 13.5 Hz), 3.75(3H, s), 4.48(1H, d, J=9.1 Hz), 4.98(1H, d, J=9.1 Hz), 5.96(2H, s), 6.29(1H, d, J=8.6 Hz), 6.67(1H, d, J=2.6 Hz), 6.73–6.80(4H, m), 6.94 (1H, d, J=8.6 Hz), 7.12(1B, d, J=8.6 Hz)

Rf Value: 0.44(E. Merck, Kieselgel 60F₂₅₄/chloroform:methanol=10:1)

EXAMPLE 185

(5RS,6SR,7SR)-2-Isobutyl-6-carboxy-7-[2-(2-carboxypropyl)-4-methoxyphenyl]-5-(3,4-methylenedioxyphenyl)cyclopenteno[1,2-b]pyridine
(one of diastereomers)

The title compound was prepared in the same manner as in Example 102 and 103 using 2-isobutyl-6-ethoxycarbonyl-7-(2-benzyloxy-4-methoxyphenyl)-5-(3,4-methylenedioxyphenyl)cyclopenteno[1,2-b]pyridine which was prepared in example 85.

¹H-NMR(300 MHz, CDCl₃, δ ppm): 0.80(3H, d, J=6.6 Hz), 0.81(3H, d, J=6.6 Hz), 1.31(3H, d, J=6.3 Hz), 1.70–1.85(1H, m), 2.55(2H, d, J=7.3 Hz), 2.62(1H, dd, J=12.5 Hz, 13.3 Hz), 2.88–3.03(1H, m), 3.37(1H, dd, J=5.7 Hz, 13.3 Hz), 3.61(1H, t, J=9.7 Hz), 3.76(3H, s), 4.59(1H, d, J=9.7 Hz), 4.99(1H, d, J=9.7 Hz), 6.00(2H, s), 6.71(1H, d, J=2.7 Hz), 6.76–6.87(4H, m), 6.93(1H, d, J=8.6 Hz), 7.03(1H, d, J=7.9 Hz), 7.33(1H, dd, J=1.1 Hz, 7.9 Hz)

Rf Value: 0.50(E. Merck, Kieselgel 60F₂₅₄/chloroform:methanol=10:1)

Each compound in the following Examples 186 and 187 was prepared in the same manner as in Example 185.

EXAMPLE 186

(5RS,6SR,7SR)-2-Butyl-6-carboxy-7-[2-(2-carboxypropyl)-4-methoxyphenyl]-5-(3,4-methylenedioxyphenyl)cyclopenteno[1,2-b]pyridine
(one of diastereomers)

mp: 107°–110° C.

¹H-NMR(300 MHz, CDCl₃, δ ppm): 0.84(3H, t, J=7.3 Hz), 1.18–1.35(2H, m), 1.31(3H, d, J=6.3 Hz), 1.40–1.56 (2H, m), 2.55–2.72(3H, m), 2.88–3.02(1H, m), 3.36(1H, dd, J=5.6 Hz, 13.1 Hz), 3.60(1H, t, J=9.7 Hz), 3.75(3H, s), 4.58(1H, d, J=9.7 Hz), 4.99(1H, d, J=9.7 Hz), 6.00(2H, brs), 6.70(1H, d, J=2.7 Hz), 6.775(1H, d, J=1.4 Hz), 6.785(1H, dd, J=2.7 Hz, 8.6 Hz), 6.81(1H, dd, J=1.4 Hz, 7.9 Hz), 6.84(1H, d, J=7.9 Hz), 6.94(1H, d, J=8.6 Hz), 7.06(1H, d, J=7.9 Hz), 7.33(1H, d, J=7.9 Hz)

Rf Value: 0.40(E. Merck, Kieselgel 60F₂₅₄/chloroform:methanol=10:1)

EXAMPLE 187

(5RS,6SR,7SR)-6-Carboxy-7-[2-(2-carboxypropyl)-4-methoxyphenyl]-2-cyclopentyl-5-(3,4-methylenedioxyphenyl)cyclopenteno[1,2-b]pyridine
(one of diastereomers)

EXAMPLE 188

(5RS,6SR,7SR)-6-Carboxy-7-[2-(2-carboxypropyl)-4-methoxyphenyl]-2-[N-(methyl)isopropylamino]-5-(3,4-methylenedioxyphenyl)cyclopenteno[1,2-b]pyridine(one of diastereomers)

The title compound was prepared in the same manner as in Example 176.

EXAMPLE 189

(5RS,6SR,7SR)-6-Carboxy-7-[2-(2-carboxypropyl)-4-methoxyphenyl]-2-[N-(ethyl)isopropylamino]-5-(3,4-methylenedioxyphenyl)cyclopenteno[1,2-b]pyridine(one of diastereomers)

The title compound was prepared in the same manner as in Example 180.

EXAMPLE 190

(5RS,6SR,7SR)-7-[2-(2-Carboxypropyl)-4-methoxyphenyl]-5-(3,4-methylenedioxyphenyl)-6-methoxycarbonylcyclopenteno[1,2-b]pyridine(one of diastereomers)

The methoxycarbonyl group of (5RS,6SR,7SR)-6-tert-butoxycarbonyl-5-(3,4-methylenedioxyphenyl)-7-[2-(2- methoxycarbonylpropyl)-4-methoxyphenyl]cyclopenteno[1,2-b]pyridine which was prepared in Example 120-(2) was hydrolyzed with base and benzylated to convert it to the benzyloxycarbonyl group. The tert-butoxycarbonyl group was cleaved with TFA and treated with $CsCO_3$ and methyl iodide to convert it to the methoxycarbonyl group. And the product was subjected to catalytic hydrogenation to give the title compound.

mp: 85°–87° C.

$^1$H-NMR(300 MHz, $CDCl_3$, δ ppm): 1.32(3H, d, J=6.4 Hz), 2.66(1H, t, J=12.9 Hz), 2.89–3.01(1H, m), 3.32(1H, dd, J=5.5 Hz, 12.9 Hz), 3.62(1H, t, J=9.8 Hz), 3.65(3H, s), 3.77(3H, s), 4.63(1H, d, J=9.8 Hz), 5.03(1H, d, J=9.8 Hz), 6.01(2H, s), 6.73–6.96(6H, m), 7.23(1H, dd, J=5.0 Hz, 7.7 Hz), 7.44(1H, td, J=1.3 Hz, 7.7 Hz), 8.28(1H, d, J=5.0 Hz)

Rf Value: 0.72(E. Merck, Kieselgel $60F_{254}$/chloroform:methanol=10:1)

EXAMPLE 191

(5RS,6SR,7SR)-6-Carboxy-7-[2-(2-carboxy-3-hydroxypropyl)-4-methoxyphenyl]-2-propylamino-5-(3,4-methylenedioxyphenyl)cyclopenteno[1,2-b]pyridine(the other diastereomer)

The title compound was prepared in the same manner as in Example 172.

mp: 192° C. (dec.)

High Resolution FAB-MS(m/e, $(C_{30}H_{32}N_2O_8+H)^+$): Calcd: 549.2237 Found: 549.2252

$^1$H-NMR(300 MHz, $CD_3OD$, δ ppm): 0.92(3H, t, J=7.2 Hz), 1.56(2H, sext, J=7.2 Hz), 2.68–3.38(4H, m), 3.06–3.19 (2H, m), 3.74(3H, s), 3.51–3.90(2H, m), 4.40–4.52(1H, m), 4.69–5.05(1H, m), 5.90(2H, s), 6.36–6.51(1H, m), 6.66–7.00(6H, m), 7.12–7.23(1H, m)

Rf Value: 0.42(E. Merck, Kieselgel $60F_{254}$/chloroform:methanol=5:1)

EXAMPLE 192

(5RS,6SR,7SR)-6-Carboxy-7-[2-(2-carboxy-3-hydroxypropyl)-4-methoxyphenyl]-2-[N-(methyl)propylamino]-5-(3,4-methylenedioxyphenyl)cyclopenteno[1,2-b]pyridine(the other diastereomer)

The title compound was prepared in the same manner as in Example 179.

EXAMPLE 193

(5RS,6SR,7SR)-6-Carboxy-7-[2-(2-carboxyethyl)-4-methoxyphenyl]-2-[N-(methyl)ethylamino]-5-(3,4-methylenedioxyphenyl)cyclopenteno[1,2-b]pyridine The title compound was prepared in the same manner as in Example 176.

mp: 119°–124° C.

High Resolution FAB-MS(m/e, $(C_{29}H_{30}N_2O_7+H)^+$): Calcd: 519.2131 Found: 519.2122

$^1$H-NMR(300 MHz, $CDCl_3$, δ ppm): 1.01(3H, t, J=7.0 Hz), 2.58–2.87(2H, m), 2.91(3H, s), 3.01–3.24(2H, m), 3.17(1H, t, J=8.6 Hz), 3.42(2H, q, J=7.0 Hz), 3.77(3H, s), 4.53(1H, d, J=8.6 Hz), 4.96(1H, d, J=8.6 Hz), 5.94(2H, s), 6.32(1H, d, J=8.6 Hz), 6.68–6.80(5H, m), 6.91(1H, d, J=8.6 Hz), 7.09(1H, d, J=8.6 Hz)

Rf Value: 0.23(E. Merck, Kieselgel $60F_{254}$/chloroform:methanol:acetic acid=20:1:1)

EXAMPLE 194

(5RS,6SR,7SR)-2-Sec-butylamino-6-carboxy-7-[2-(2-carboxypropyl)-4-methoxyphenyl]-5-(3,4-methylenedioxyphenyl)cyclopenteno[1,2-b]pyridine(one of diastereomers derived from the carboxypropyl group)

The title compound was prepared in the same manner as in Example 161 using corresponding racemate of sec-butylamine compound.

mp: 147°–153° C.

$^1$H-NMR(300 MHz, acetone-$d_6$, δ ppm): 0.82+0.87(3H, t×2, J=7.5 Hz), 1.06+1.10(3H, d×2, J=7.4 Hz), 1.21(3H, d, J=6.3 Hz), 1.13–1.61(2H, m), 2.82–3.01(2H, m), 3.08–3.16 (1H, m), 3.275+3.284(1H, t×2, J=9.2 Hz), 3.58– 3.70(1H, m), 3.75(3H, s), 4.47(1H, d, J=9.2 Hz), 4.89(1H, d, J=9.2 Hz), 5.23(1H, brs), 6.00(2H, s), 6.40(1H, d, J=8.2 Hz), 6.73–6.89(5H, m), 7.05(1H, d, J=7.5 Hz), 7.08(1H, d, J=8.2 Hz)

Rf Value: 0.45(E. Merck, Kieselgel $60F_{254}$/chloroform:methanol=10:1)

EXAMPLE 195

(5RS,6SR,7SR)-6-Carboxy-7-[2-(3-carboxy-2-methylpropyl)-4-methoxyphenyl]-2-propylamino-5-(3,4-methylenedioxyphenyl)cyclopenteno[1,2-b]pyridine(one of diastereomers)

(1) (5RS,6SR,7SR)-7-[2-(3-Carboxypropyl)-4-methoxyphenyl]-2-[N-(benzoyl)propylamino]-6-tert-butoxycarbonyl-5-(3,4-methylenedioxyphenyl)cyclopenteno[1,2-b]pyridine (5RS,6SR,7SR)-6-tert-Butoxycarbonyl-5-(3,4-methylenedioxyphenyl)-7-[2-(2-methoxycarbonylpropyl)-4-methoxyphenyl]cyclopenteno[1,2-b]pyridine which was prepared in Example 102-(2) was subjected to the same reaction as in Example 124-(1) and (2) to give the corresponding N-benzoyl diester compound. The N-benzoyl diester compound was reacted with 4N NaOH in dioxane at room temperature to give (5RS,6SR,7SR)-7-[2-(3-carboxypropyl)-4-methoxyphenyl]-2-[N-(benzoyl)propylamino]-6-tert-butoxycarbonyl-5-(3,4-methylenedioxyphenyl)cyclopenteno[1,2-b]pyridine (2) The title compound was prepared in the same manner as in Example 169 using (5RS,6SR,7SR)-7-[2-(3-carboxypropyl)-4-methoxyphenyl]-2-[N-(benzoyl)propylamino]-6-tert-butoxycarbonylcyclopenteno[1,2-b]pyridine.

EXAMPLE 196

(5RS,6SR,7SR)-6-Tert-butoxycarbonyl-7-[2-(2-methoxycarbonyl-2-propenyl)-4-methoxyphenyl]-5-(3,4-methylenedioxyphenyl)-5-(3,4-methylenedioxyphenyl)cyclopenteno[1,2-b]pyridine (5RS,6SR,7SR)-7-(2-Trifluoromethanesulfonyloxy-4-methoxyphenyl)-6-tert-butoxycarbonyl-5-(3,4-methylenedioxyphenyl)cyclopenteno[1,2-b]pyridine(100 mg,0.169 mmol) which was prepared in Example 99-(1) and LiCl(21 mg) were added in a Schlenk reactor under nitrogen atmosphere. To the mixture were added a DMF solution(1.5 ml) of (2-methoxycarbonyl-2-propenyl)tributyltin(131 mg) which was prepared by the method described in the literature [J. Chem. Soc. Chem. Commun., 1339–1340(1986), Tetrahedron, 47, 5901(1991)], palladium(II) chloride bis-triphenylphosphine complex(6 mg) and the mixture was heated at 100° C. for 15 h. To the reaction solution were added AcOEt(3 ml) and a 40% aqueous KF solution(1 ml) and the mixture was stirred vigorously for 10 min. The resulting precipitate was removed by Celite-filtration and the filtrate and washings were combined and washed with water dried over MgSO$_4$. After removal of the solvent the residue was purified by silica gel column chromatography(E. Merck Kieselgel 60/hexane:AcOEt=2:1) to give the title compound (85.7 mg)

EXAMPLE 197

(5RS,6SR,7SR)-2-(1-Ethylpropylamino)-6-carboxy-7-[2-(2-carboxypropyl)-4-methoxyphenyl]-5-(3,4-methylenedioxyphenyl)cyclopenteno[1,2-b]pyridine (one of diastereomers)

The title compound was prepared in the same manner as in Example 171.

Each compound in the following Examples 198–200 was prepared in the same manners as in Examples 162 and 163.

EXAMPLE 198

(5RS,6SR,7SR)-6-Carboxy-7-[2-(2-carboxypropyl)-4-methoxyphenyl]-2-tert-butylamino-5-(3,4-methylenedioxyphenyl)cyclopenteno[1,2-b]pyridine (one of diastereomers)

EXAMPLE 199

(5RS,6SR,7SR)-6-Carboxy-7-[2-(2-carboxy-2-propenyl)-4-methoxyphenyl]-2-isopropylamino-5-(3,4-methylenedioxyphenyl)cyclopenteno[1,2-b]pyridine(one of diastereomers).

EXAMPLE 200

(5RS,6SR,7SR)-6-Carboxy-7-[2-(2-carboxypropyl)-4-methoxyphenyl]-2-cyclohexylamino-5-(3,4-methylenedioxyphenyl)cyclopenteno[1,2-b]pyridine (one of diastereomers)

Utilizability in Industry

The heteroaromatic ring fused compounds of the present invention possess high antagonistic activity to endotheline, endogenious biologically active peptide, so that they are useful as drugs which possess high antagonistic activity to endotheline related vasoconstriction and bronchoconstriction. The compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

We claim:
1. A heteroaromatic ring-fused cyclopentene derivative of the formula:

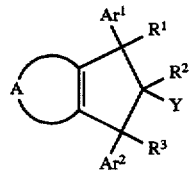

(I)

wherein
each of Ar$^1$ and Ar$^2$ is independently a phenyl group, a thienyl group, a pyridyl group, an indolyl group, a benzofuranyl group or a dihydrobenzofuranyl group wherein an optional hydrogen atom(s) on the aromatic ring may be replaced with 1 to 4 groups selected from the group consisting of a halogen atom, a hydroxyl group, an amino group, a carboxyl group, a C$_1$–C$_6$ alkoxycarbonyl group, a mono- or di- C$_1$–C$_6$ alkylaminocarbonyl group, a carbamoyl group, a tetrazol-5-yl group, a methylenedioxy group, a C$_1$–C$_6$ alkoxy group, a C$_2$–C$_6$ alkenyloxy group, a mono- or di- C$_1$–C$_6$ alkylamino group, a C$_1$–C$_6$ alkyl group, a C$_2$–C$_6$ alkenyl group and a C$_2$–C$_6$ alkynyl group (provided that the C$_1$–C$_6$ alkoxy group, C$_2$–C$_6$ alkenyloxy group, mono- or di- C$_1$–C$_6$ alkylamino group, C$_1$–C$_6$ alkyl group, C$_2$–C$_6$ alkenyl group and C$_2$–C$_6$ alkynyl group may be substituted by 1 to 3 groups selected from the group consisting of a phenyl group, a pyridyl group, an imidazolyl group, a hydroxyl group, a C$_1$–C$_6$ alkoxy group, an amino group, a mono- or di- C$_1$–C$_6$ alkylamino group, a hydroxy C$_1$–C$_6$ alkylcarbonyl group, a C$_1$–C$_6$ acyloxy C$_1$–C$_6$ alkylcarbonyl group, a carboxy C$_1$–C$_6$ alkoxycarbonyl group, a carboxy C$_1$–C$_6$ alkoxycarbonyl C$_1$–C$_6$ alkoxycarbonyl group, a C$_1$–C$_6$ alkoxycarbonyl group, a mono- or di- C$_1$–C$_6$ alkylaminocarbonyl group, a carbamoyl group, a C$_1$–C$_6$ alkylsulfonylaminocarbonyl group, a tetrazol-5-yl-aminocarbonyl group, a carboxyl group, SO$_3$H, PO$_3$H$_2$, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as substituents, they may together form a lactone ring));

each of R$^1$, R$^2$ and R$^3$ is independently a hydrogen atom, a hydroxyl group or a C$_1$–C$_6$ alkyl group, or R$^1$ and R$^2$, or R$^2$ and R$^3$ together form a single bond;

Y is a group of —CO—R$^4$ (wherein R$^4$ is a hydroxyl group, an amino group, a C$_1$–C$_6$ alkoxy group, a mono- or di- C$_1$–C$_6$ alkylamino group, a C$_1$–C$_6$ alkylsulfonylamino group, an arylsulfonylamino group or an aryl C$_1$–C$_6$ alkylsulfonylamino group wherein an optional hydrogen atom(s) on the aryl ring may be replaced with a C$_1$–C$_6$ alkyl group), SO$_3$H, PO$_3$H$_2$, a tetrazol-5-yl group, a 2-oxo-3H-1,2,3,5-oxathiadiazol-4-yl group or a 5-oxo-4H-1,2,4-oxadiazol-3-yl-group; and A is a group which forms together with the adjacent carbon-carbon double bond a pyridine, pyrimidine, pyridazine, pyrazine or thiazole ring; provided that optional 1 or 2 hydrogen atoms on the heteroaromatic ring may be replaced with a hydroxyl group, an amino group, a C$_1$–C$_6$ alkoxy group, a C$_1$–C$_6$ alkylthio group, a halogen atom, a cyano group, a nitro group, a mono- or di- C$_1$–C$_6$ alkylamino group which may be substituted by a hydroxyl group at the alkyl moiety; a C$_3$–C$_8$ cycloalkylamino group which may be substituted by a hydroxyl group at the alkyl or alkylene moiety, a C$_3$–C$_8$ cycloalkyl C$_1$–C$_6$ alkylamino group which may be substituted by a hydroxyl group at the alkyl or alkylene moiety an N-(C$_1$–C$_6$ alkyl)-N-(C$_3$–C$_8$ cycloalkyl) amino group which may be substituted by a hydroxyl group at the alkyl or alkylene moiety, an N-($C_1$-$C_6$ alkyl)-N-(aroyl)amino group which may be substituted by a hydroxyl group at the alkyl moiety, a $C_4$-$C_7$ cyclic imino group which may be substituted by a hydroxyl group at the alkylene moiety, a carboxyl group, a $C_1$-$C_6$ alkoxycarbonyl group, a formyl group, a $C_2$-$C_6$ alkanoyl group, an aroyl group, or a $C_1$-$C_6$ alkyl group, $C_3$-$C_8$ cycloalkyl group, $C_3$-$C_8$ cycloalkyl $C_1$-$C_6$ alkyl group, $C_2$-$C_6$ alkenyl group or $C_2$-$C_6$ alkynyl group which may be substituted by 1 to 3 substituents selected from the group consisting of a hydroxyl group, an amino group, a $C_1$-$C_6$ alkoxy group and a mono- or di- $C_1$-$C_6$ alkylamino group, and when the heteroaromatic ring includes one or more nitrogen atoms, the nitrogen atom(s) may be oxidized to form an N-oxide group; or a pharmaceutically acceptable salt thereof.

2. A heteroaromatic ring-fused cyclopentene derivative of claim 1, wherein A is a group which forms together with the adjacent carbon-carbon double bond a substituted or unsubstituted pyridine, pyrimidine, pyridazine, pyrazine or thiazole ring; each of $Ar^1$ and $Ar^2$ is independently a phenyl group, a thienyl group or a dihydrobenzofuranyl group wherein an optional hydrogen atom(s) on the aromatic ring may be replaced with 1 to 4 groups selected from the group consisting of a halogen atom, a hydroxyl group, an amino group, a methylenedioxy group, a $C_1$-$C_6$ alkoxy group, a $C_2$-$C_6$ alkenyloxy group, a mono- or di- $C_1$-$C_6$ alkylamino group, a $C_1$-$C_6$ alkyl group, a $C_2$-$C_6$ alkenyl group and a $C_2$-$C_6$ alkynyl group (provided that the said $C_1$-$C_6$ alkoxy group, $C_2$-$C_6$ alkenyloxy group, mono- or di- $C_1$-$C_6$ alkylamino group, $C_1$-$C_6$ alkyl group, $C_2$-$C_6$ alkenyl group and $C_2$-$C_6$ alkynyl group may be substituted by 1 to 3 groups selected from the group consisting of a phenyl group, a pyridyl group, an imidazolyl group, a hydroxyl group, a $C_1$-$C_6$ alkoxy group, an amino group, a mono- or di- $C_1$-$C_6$ alkylamino group, a hydroxy $C_1$-$C_6$ alkylcarbonyl group, a $C_1$-$C_6$ acyloxy $C_1$-$C_6$ alkylcarbonyl group, a carboxy $C_1$-$C_6$ alkoxycarbonyl group, a carboxy $C_1$-$C_6$ alkoxycarbonyl $C_1$-$C_6$ alkoxycarbonyl group, a $C_1$-$C_6$ alkoxycarbonyl group, a mono- or di- $C_1$-$C_6$ alkylaminocarbonyl group, a carbamoyl group, a $C_1$-$C_6$ alkylsulfonylaminocarbonyl group, a tetrazol-5-ylaminocarbonyl group, a carboxyl group, a tetrazol-5-yl group, a 2-oxo-3H-1,2,3,5-oxathiadiazol-4-yl group and a 5-oxo-4H-1,2,4-oxadiazol-3-yl group (provided that when a hydroxyl group and a carboxyl group are selected as the substituents, they may together form a lactone ring)); or a pharmaceutically acceptable salt thereof.

3. A heteroaromatic ring-fused cyclopentene derivative of claim 1, wherein A is a group which forms together with the adjacent carbon-carbon double bond a substituted or unsubstituted pyridine ring; or a pharmaceutically acceptable salt thereof.

4. A heteroaromatic ring-fused cyclopentene derivative of claim 2, wherein A is a group which forms together with the adjacent carbon-carbon double bond, a pyridine ring; or a pharmaceutically acceptable salt thereof.

5. A heteroaromatic ring-fused cyclopentene derivative of claim 1, wherein A is a group which forms together with the adjacent carbon-carbon double bond a substituted or unsubstituted pyrimidine ring; or a pharmaceutically acceptable salt thereof.

6. A heteroaromatic ring-fused cyclopentene derivative of claim 1, wherein A is a group which forms together with the adjacent carbon-carbon double bond a substituted or unsubstituted pyridazine ring; or a pharmaceutically acceptable salt thereof.

7. A heteroaromatic ring-fused cyclopentene derivative of claim 1, wherein A is a group which forms together with the adjacent carbon-carbon double bond a substituted or unsubstituted pyrazine ring; or a pharmaceutically acceptable salt thereof.

8. A heteroaromatic ring-fused cyclopentene derivative of claim 1, wherein A is a group which forms together with the adjacent carbon-carbon double bond a substituted or unsubstituted thiazole ring; or a pharmaceutically acceptable salt thereof.

9. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 1, or a pharmaceutically acceptable salt thereof and a pharmaceutically acceptable carrier.

10. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 2 or a pharmaceutically acceptable salt thereof and a pharmaceutically acceptable carrier.

11. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 3 or a pharmaceutically acceptable salt thereof and a pharmaceutically acceptable carrier.

12. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 5 or a pharmaceutically acceptable salt thereof and a pharmaceutically acceptable carrier.

13. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 6 or a pharmaceutically acceptable salt thereof and a pharmaceutically acceptable carrier.

14. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/ or cyclosporin-induced renal failure or hypertension, which contains a heteroaromatic ring-fused cyclopentene derivative of claim 7 or a pharmaceutically acceptable salt thereof and a pharmaceutically acceptable carrier.

15. A drug composition for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe, endotoxin shock, endotoxin-induced multiple organ failure or disseminated intravascular coagulation, and/or cyclosporin-induced renal failure or hypertension, which contains a heteroaromatic ring-fused cyclopentene derivative of claim 8 or a pharmaceutically acceptable salt thereof and a pharmaceutically acceptable carrier.

16. A method for inducing vasodilation or bronchodilation in a patient in need thereof, comprising administering an effective amount of the heteroatomic ring-fused cyclopentene of claim 1.

17. A method for inducing vasodilation or bronchodilation in a patient in need thereof, comprising ad A method for inducing vasodilation or bronchodilation in a patient in need thereof, comprising administering an effective amount of the heteroaromatic ring-fused cyclopentene of claim 2.

18. A method for inducing vasodilation or bronchodilation in a patient in need thereof, comprising administering an effective amount of the heteroaromatic ring-fused cyclopentene of claim 3.

19. A method for inducing vasodilation or bronchodilation in a patient in need thereof, comprising administering an effective amount of the heteroaromatic ring-fused cyclopentene of claim 5.

20. A method for inducing vasodilation or bronchodilation in a patient in need thereof, comprising administering an effective amount of the heteroaromatic ring-fused cyclopentene of claim 6.

21. A method for inducing vasodilation or bronchodilation in a patient in need thereof, comprising administering an effective amount of the heteroaromatic ring-fused cyclopentene of claim 7.

22. A method for inducing vasodilation or bronchodilation in a patient in need thereof, comprising administering an effective amount of the heteroaromatic ring-fused cyclopentene of claim 8.

* * * * *